(12) United States Patent
Lim et al.

(10) Patent No.: US 8,431,251 B2
(45) Date of Patent: Apr. 30, 2013

(54) HETEROCYCLIC COMPOUND AND ORGANIC LIGHT-EMITTING DEVICE COMPRISING THE SAME

(75) Inventors: Jin-O Lim, Yongin (KR); Seok-Hwan Hwang, Yongin (KR); Young-Kook Kim, Yongin (KR); Hye-Jin Jung, Yongin (KR); Sang-Hyun Han, Yongin (KR); Chang-Ho Lee, Yongin (KR); Jong-Hyuk Lee, Yongin (KR); Hee-Joo Ko, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 0 days.

(21) Appl. No.: 13/314,312

(22) Filed: Dec. 8, 2011

(65) Prior Publication Data

US 2013/0001524 A1 Jan. 3, 2013

(30) Foreign Application Priority Data

Jun. 29, 2011 (KR) ......................... 10-2011-0064076

(51) Int. Cl.
*H01L 51/54* (2006.01)
(52) U.S. Cl.
USPC ........... 428/690; 428/917; 313/504; 313/505; 313/506; 564/26; 564/426; 564/434; 546/18; 546/79; 546/81; 546/101; 548/440
(58) Field of Classification Search .................. 428/690, 428/917; 313/504, 505, 506; 564/26, 426, 564/434; 546/18, 79, 81, 101; 548/440
See application file for complete search history.

(56) References Cited

U.S. PATENT DOCUMENTS 5,635,308 A 6/1997 Inoue et al.
(Continued)

FOREIGN PATENT DOCUMENTS

JP 08012600 1/1996
(Continued)

OTHER PUBLICATIONS

Sakamoto et al., Synthesis, Characterization, and Electron-Transport Property of Perfluorinated Phenylene Dendrimers, J. Am. Chem. Soc. (2000) 122, pp. 1832-1833.

(Continued)

*Primary Examiner* — Jennifer A Chriss
*Assistant Examiner* — Gregory Clark
(74) *Attorney, Agent, or Firm* — Robert E. Bushnell, Esq.

(57) ABSTRACT

A heterocyclic compound represented by Formula 1 below and an organic light-emitting device including an organic layer that includes the following heterocyclic compound:

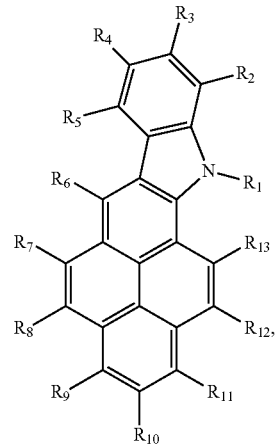

wherein $R_1$ to $R_{13}$ are each independently a hydrogen atom, a heavy hydrogen atom, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C1-C60 alkoxy group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, a substituted or unsubstituted C6-C60 condensed polycyclic group, a halogen atom, a cyano group, a nitro group, a hydroxy group, or a carboxy group.

20 Claims, 2 Drawing Sheets

U.S. PATENT DOCUMENTS

| | | | |
|---|---|---|---|
| 5,645,948 | A | 7/1997 | Shi et al. |
| 5,972,247 | A | 10/1999 | Shi et al. |
| 6,465,115 | B2 | 10/2002 | Shi et al. |
| 6,596,415 | B2 | 7/2003 | Shi et al. |
| 2008/0203905 | A1 | 8/2008 | Je et al. |

FOREIGN PATENT DOCUMENTS

| | | |
|---|---|---|
| JP | 2000003782 | 1/2000 |
| JP | 2008078362 | 4/2008 |
| KR | 1020090072152 | 7/2009 |
| KR | 1020110039108 | 4/2011 |

OTHER PUBLICATIONS

Adachi et al., Confinement of charge carriers and molecular excitons within 5-nm-thick emitter layer in organic electroluminescent devices with a double heterostructure, Appl. Phys. Lett. (1990) 57, pp. 531-533.

Tang et al., Organic elcectroluminescent diodes, Appl. Phys. Lett. (1987) 51, pp. 913-915.

Chemistry Letters 2001: Diphenylamino-Substituted 2,5-Diarysiloles for Single-Layer Organic Electroluminescent Device by Shigehiro Yamaguchi et al.

HETEROCYCLIC COMPOUND AND ORGANIC LIGHT-EMITTING DEVICE COMPRISING THE SAME

CLAIM OF PRIORITY

This application claims the benefit of Korean Patent Application No. 10-2011-0064076, filed on 29 Jun. 2011 in the Korean intellectual Property Office, the disclosure of which is incorporated herein in its entirety by reference.

BACKGROUND OF THE INVENTION

1. Field of the Invention

The present invention relates to a heterocyclic compound represented by Formula 1 below and an organic light-emitting device including the heterocyclic compound.

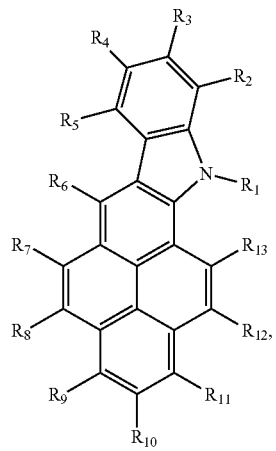

Formula 1

2. Description of the Related Art

Light-emitting devices are self-emission type display devices and have a wide viewing angle, a high contrast ratio, and a short response time. Due to these characteristics, light-emitting devices are drawing more attention.

Such light-emitting devices can be roughly classified into inorganic light-emitting devices that include emission layers containing inorganic compounds, and organic light-emitting devices that include emission layers containing organic compounds.

Specifically, organic light-emitting devices have higher luminance, lower driving voltages, and shorter response times than inorganic light-emitting devices, and can render multi-colored displays. Thus, much research into such organic light-emitting devices has been conducted.

Typically, an organic light-emitting device has a stack structure including an anode, a cathode and an organic emission layer between the anode and the cathode. However, a hole injection layer, a hole transport layer, an electron transport layer, or an electron injection layer may further be stacked between the anode and the organic emission layer, or between the organic emission layer and the cathode. In other words, an organic light-emitting device may have an anode/hole transport layer/organic emission layer/cathode structure or an anode/hole transport layer/organic emission layer/electron transport layer/cathode structure.

As a material for the organic emission layer, an anthracene derivative has been used. However, organic light-emitting devices including such a known organic emission material do not have satisfactory life span, efficiency, and power consumption characteristics. Therefore improvement in these properties is still necessary.

SUMMARY OF THE INVENTION

The present invention provides a heterocyclic compound having excellent electrical stability, high charge transporting capability, excellent light-emitting ability, high glass transition temperature, and excellent anti-crystallization properties.

The present invention also provides an organic light-emitting device including the heterocyclic compound.

The present invention also provides a flat panel display device including the organic light-emitting device.

According to an aspect of the present invention, there is provided a heterocyclic compound represented by Formula 1 below:

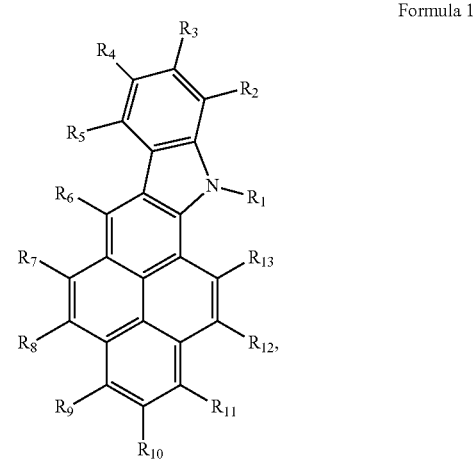

Formula 1 wherein $R_1$ to $R_{13}$ are each independently a hydrogen atom, a heavy hydrogen atom, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C1-C60 alkoxy group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, a substituted or unsubstituted C6-C60 condensed polycyclic group, a halogen atom, a cyano group, a nitro group, a hydroxy group, or a carboxy group.

In Formula 1, $R_1$ to $R_5$ are each independently a hydrogen atom, a heavy hydrogen atom, a halogen atom, a cyano group, a substituted or unsubstituted C1-C20 alkyl group, or one of Formulae 2a to 2i below:

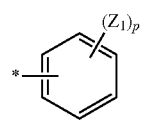

2a

-continued

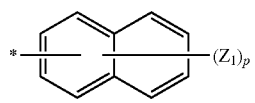
2b

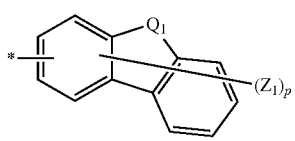
2c

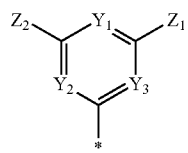
2d

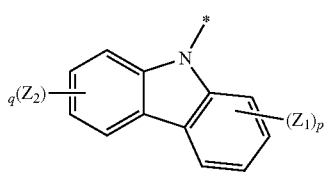
2e

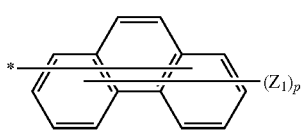
2f

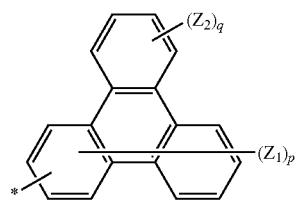
2g

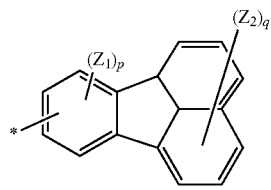
2h

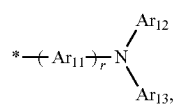
2i wherein $Q_1$ is a linking group represented by —C($R_{14}$)($R_{15}$)—, —N($R_{16}$)—, —S—, or —O—;

$Y_1$, $Y_2$ and $Y_3$ are each independently a linking group represented by —N= or —C($R_{17}$)=;

$Z_1$, $Z_2$, $Ar_{12}$, $Ar_{13}$, $R_{14}$, $R_{15}$, $R_{16}$, and $R_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

$Ar_{11}$ is a substituted or unsubstituted C1-C20 alkylene group, a substituted or unsubstituted C5-C20 arylene group, or a substituted or unsubstituted C3-C20 heteroarylene group;

p is an integer from 1 to 12;
q is an integer from 1 to 12;
r is an integer from 0 to 5; and
* is a binding site.

In Formula 1, $R_1$ to $R_5$ are each independently a hydrogen atom, a heavy hydrogen atom, a halogen atom, a cyano group, a methyl group, an ethyl group, a propyl group, a butyl group, a t-butyl group, a pentyl group, or one of Formulae 3a to 3m below:

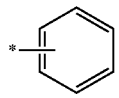
3a

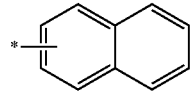
3b

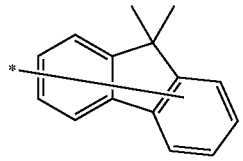
3c

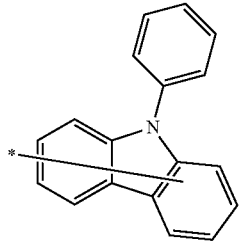
3d

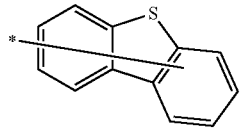
3e

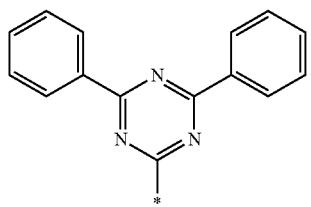
3f

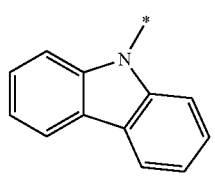
3g

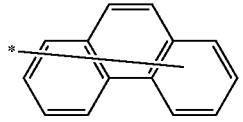
3h

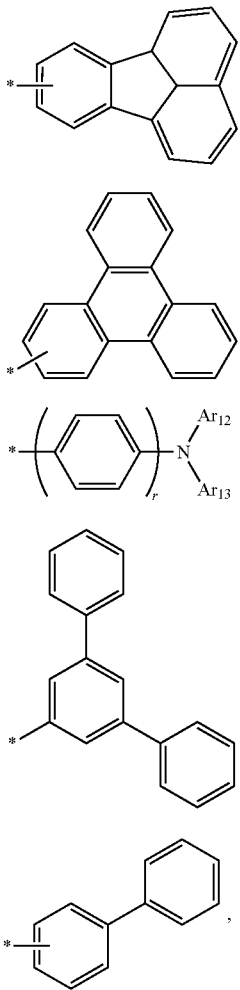

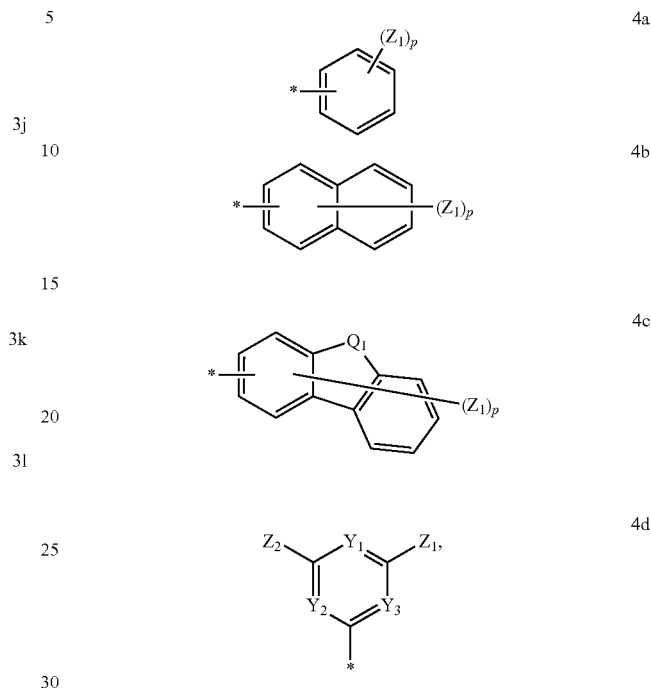

wherein Ar$_{12}$ and Ar$_{13}$ are each independently a substituted or unsubstituted C5-C20 aryl group, a substituted or unsubstituted C3-C20 heteroaryl group, or a substituted or unsubstituted C6-C20 condensed polycyclic group;

r is an integer from 0 to 2; and

* is a binding site.

In Formula 1, R$_6$ to R$_8$ and R$_{10}$ to R$_{13}$ are each independently a hydrogen atom or a heavy hydrogen atom, and R$_9$ is —X$_1$—N(Ar$_1$Ar$_2$) that is a substituted C5-C60 aryl group, a substituted C3-C60 heteroaryl group, or a substituted C6-C60 condensed polycyclic group; or R$_6$ to R$_{10}$, R$_{12}$ and R$_{13}$ are each independently a hydrogen atom or a heavy hydrogen atom, and R$_{11}$ is —X$_1$—N(Ar$_1$Ar$_2$) that is a substituted C5-C60 aryl group, a substituted C3-C60 heteroaryl group or a substituted C6-C60 condensed polycyclic group, wherein X$_1$ is a divalent linking group represented by —(Ar$_3$)$_n$—, wherein Ar$_3$ is a substituted or unsubstituted C5-C60 arylene group, a substituted or unsubstituted C3-C60 heteroarylene group, or a substituted or unsubstituted C6-C60 condensed polycyclic group, and n is an integer from 1 to 10;

the Ar$_3$'s are the same or different;

at least two adjacent Ar$_3$'s are fused or linked to each other via a single bond; and Ar$_1$ and Ar$_2$ are each independently one of Formulae 4a to 4d below:

wherein Q$_1$ is a linking group represented by —C(R$_{14}$)(R$_{15}$)—, —N(R$_{16}$)—, —S—, or —O—;

Y$_1$, Y$_2$ and Y$_3$ are each independently a linking group represented by —N= or —C(R$_{17}$)=;

Z$_1$, Z$_2$, R$_{14}$, R$_{15}$, R$_{16}$, and R$_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

p is an integer from 1 to 8; and

* is a binding site.

In Formula 1, R$_6$ to R$_8$ and R$_{10}$ to R$_{13}$ are each independently a hydrogen atom or a heavy hydrogen atom, and R$_9$ is —X$_1$—N(Ar$_1$Ar$_2$) that is a substituted C5-C60 aryl group, a substituted C3-C60 heteroaryl group, or a substituted C6-C60 condensed polycyclic group; or R$_6$ to R$_{10}$, R$_{12}$ and R$_{13}$ are each independently a hydrogen atom or a heavy hydrogen atom, and R$_{11}$ is —X$_1$—N(Ar$_1$Ar$_2$) that is a substituted C5-C60 aryl group, a substituted C3-C60 heteroaryl group or a substituted C6-C60 condensed polycyclic group, wherein X$_1$ is a divalent linking group represented by —(Ar$_3$)$_n$—, wherein Ar$_3$ is a substituted or unsubstituted C5-C60 arylene group, a substituted or unsubstituted C3-C60 heteroarylene group, or a substituted or unsubstituted C6-C60 condensed polycyclic group, and n is an integer from 1 to 10;

the Ar$_3$'s are the same or different;

at least two adjacent Ar$_3$'s are fused or linked to each other via a single bond; and $Ar_1$ and $Ar_2$ are each independently represented by one of Formulae 5a to 5i below:

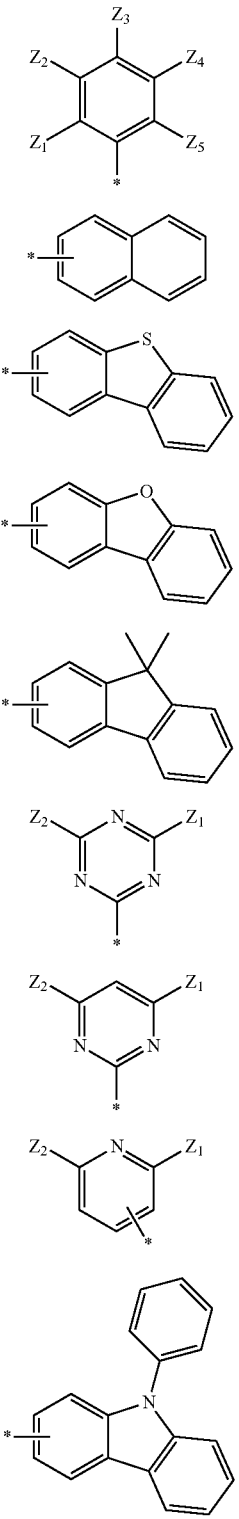

wherein $Z_1$ to $Z_5$ are each independently a hydrogen atom, a heavy hydrogen atom, a halogen atom, a cyano group, a substituted or unsubstituted C1-C20 alkyl group, a substituted or unsubstituted C1-C20 alkoxy group, a substituted or unsubstituted C5-C20 aryl group, a substituted or unsubstituted C3-C20 heteroaryl group, or a substituted or unsubstituted C6-C20 condensed polycyclic group; and

* is a binding site.

In Formula 1, $R_9$ or $R_{11}$ are each independently $X_1$—N($Ar_1Ar_2$) that is a substituted C5-C60 aryl group, a substituted C3-C60 heteroaryl group, or a substituted C6-C60 condensed polycyclic group, wherein $Ar_1$ and $Ar_2$ are each independently a substituted or unsubstituted C3-C50 cycloalkyl group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, or a substituted or unsubstituted C6-C60 condensed polycyclic group; and $X_1$ is a divalent linking group represented by —$(Ar_3)_n$—, wherein $Ar_3$ is one of Formulae 6a to 6e, and the $Ar_3$'s are the same or different; and at least two adjacent $Ar_3$'s are fused or linked to each other via a single bond:

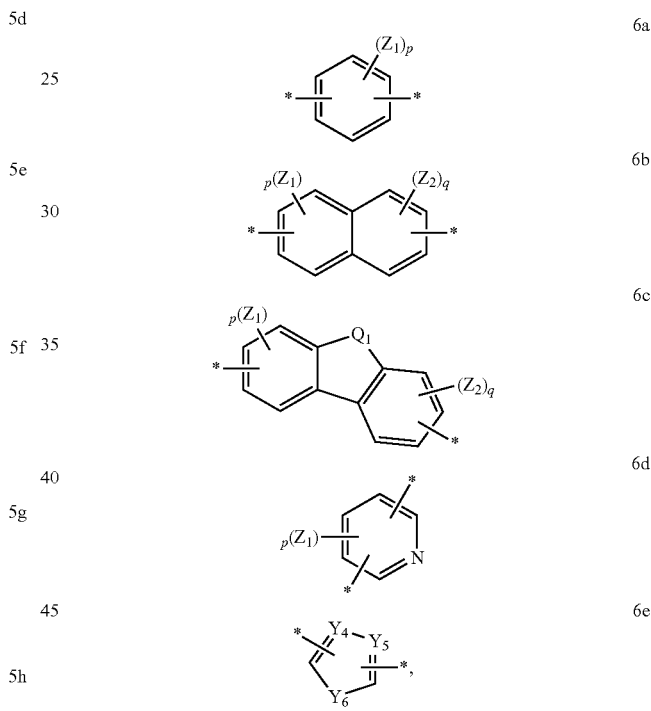

wherein $Q_1$ is a linking group represented by —$C(R_{14})(R_{15})$—, —$N(R_{16})$—, —S—, or —O—;

$Y_4$, $Y_5$ and $Y_6$ are each independently a linking group represented by —O—, —S—, —N= or —$C(R_{17})$=;

$Z_1$, $Z_2$, $R_{14}$, $R_{15}$, $R_{16}$, and $R_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

p is an integer from 1 to 4;

q is an integer from 1 to 4; and

* is a binding site.

In Formula 1, $R_9$ or $R_{11}$ are each independently $X_1$—N($Ar_1Ar_2$) that is a substituted C5-C60 aryl group, a substituted C3-C60 heteroaryl group, or a substituted C6-C60 condensed polycyclic group, wherein $Ar_1$ and $Ar_2$ are each independently a substituted or unsubstituted C3-C50 cycloalkyl group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, or a substituted or unsubstituted C6-C60 condensed polycyclic group; and $X_1$ is one of Formulae 7a to 7k below:

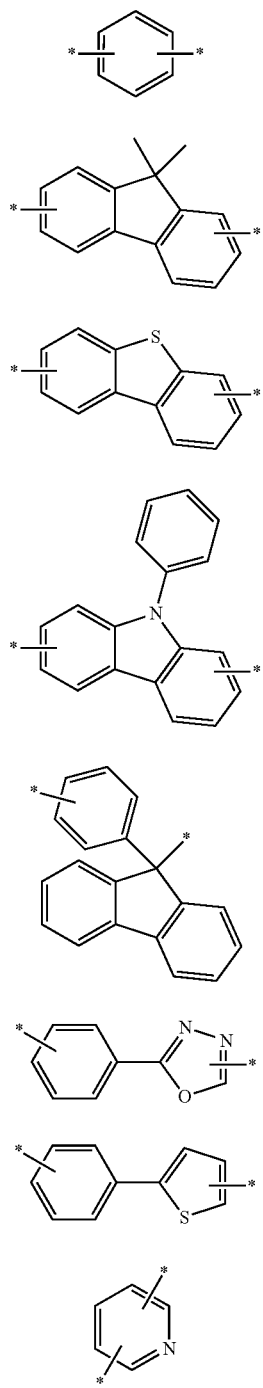

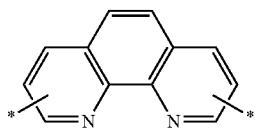

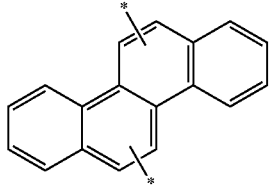

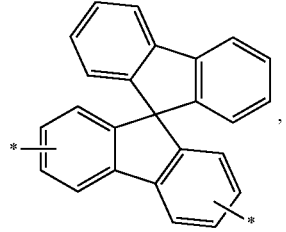

wherein * is a binding site.

The heterocyclic compound of Formula 1 may be represented by Formula 2 or Formula 3 below:

<Formula 2>

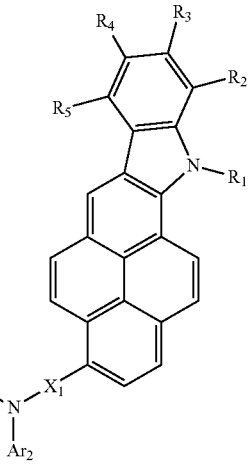

<Formula 3>

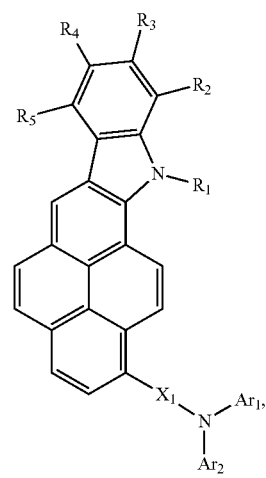

wherein R₁ to R₅ are each independently a hydrogen atom, a heavy hydrogen atom, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C1-C60 alkoxy group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, a substituted or unsubstituted C6-C60 condensed polycyclic group, a halogen atom, a cyano group, a nitro group, a hydroxy group, or a carboxy group;

Ar₁ and Ar₂ are each independently a substituted or unsubstituted C3-C50 cycloalkyl group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, or a substituted or unsubstituted C6-C60 condensed polycyclic group;

X₁ is a divalent linking group represented by —(Ar₃)ₙ—, wherein Ar₃ may be a substituted or unsubstituted C5-C60 arylene group, a substituted or unsubstituted C3-C60 heteroarylene group, or a substituted or unsubstituted C6-C60 condensed polycyclic group, and n is an integer from 1 to 10;

the Ar₃'s are the same or different; and at least two adjacent Ar₃'s are fused or linked to each other via a single bond.

In Formulae 2 and 3, R₁ to R₅ are each independently a hydrogen atom, a heavy hydrogen atom, a halogen atom, a cyano group, a substituted or unsubstituted C1-C20 alkyl group, or one of Formulae 2a to 2i below:

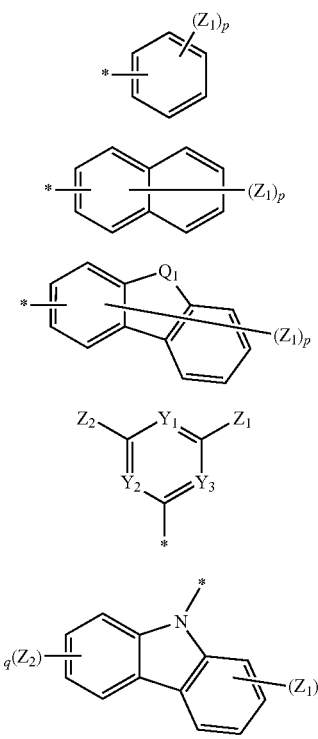

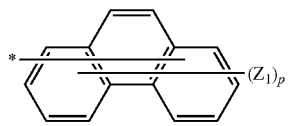

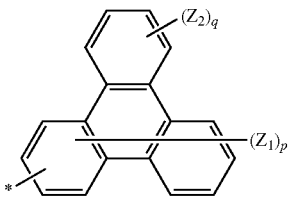

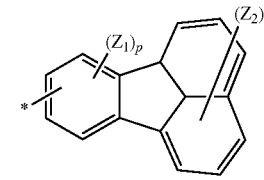

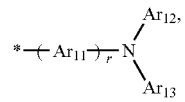

wherein Q₁ is a linking group represented by —C(R₁₄)(R₁₅)—, —N(R₁₆)—, —S—, or —O—;

Y₁, Y₂ and Y₃ are each independently a linking group represented by —N= or —C(R₁₇)=;

Z₁, Z₂, Ar₁₂, Ar₁₃, R₁₄, R₁₅, R₁₆, and R₁₇ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

Ar₁₁ is a substituted or unsubstituted C1-C20 alkylene group, a substituted or unsubstituted C5-C20 arylene group, or a substituted or unsubstituted C3-C20 heteroarylene group;

p is an integer from 1 to 12;

q is an integer from 1 to 12;

r is an integer from 0 to 5; and

* is a binding site.

In Formulae 2 and 3, R₁ to R₅ are each independently a hydrogen atom, a heavy hydrogen atom, a halogen atom, a cyano group, a methyl group, an ethyl group, a propyl group, a butyl group, a t-butyl group, a pentyl group, or one of Formulae 3a to 3m below:

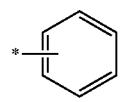

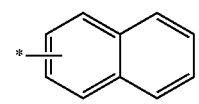

-continued

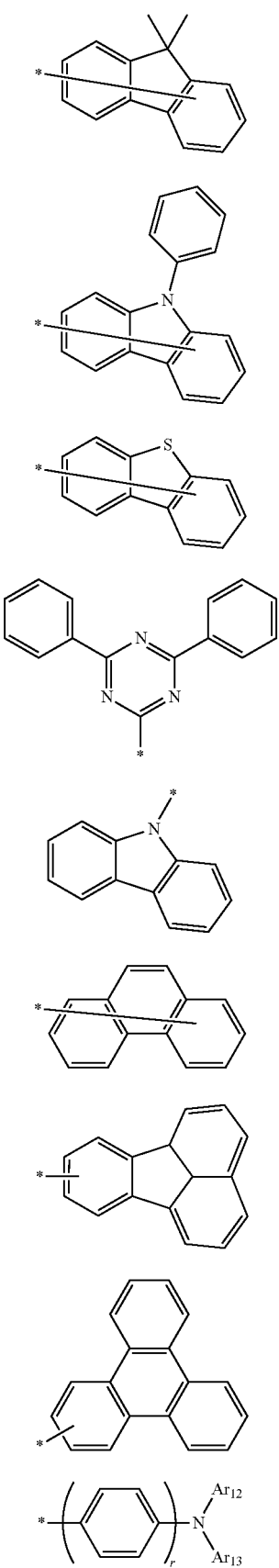

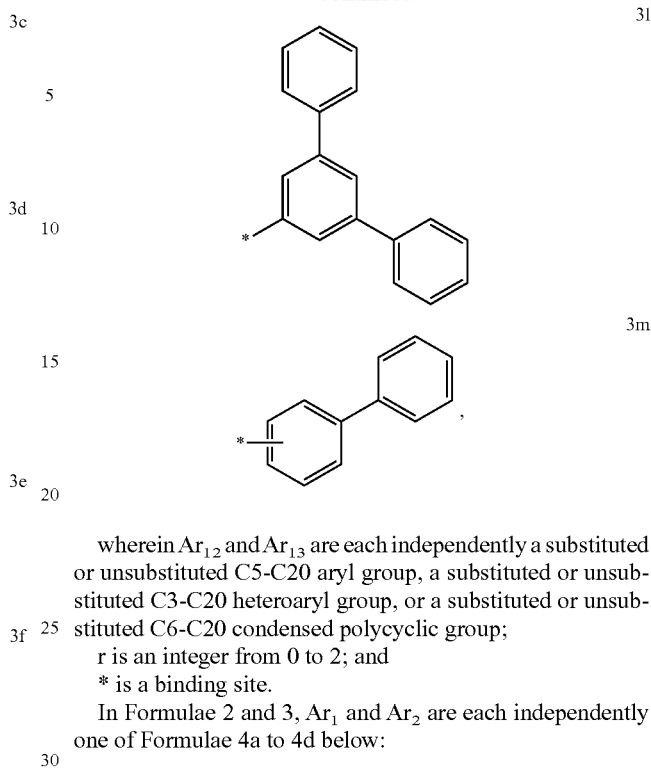

wherein Ar₁₂ and Ar₁₃ are each independently a substituted or unsubstituted C5-C20 aryl group, a substituted or unsubstituted C3-C20 heteroaryl group, or a substituted or unsubstituted C6-C20 condensed polycyclic group;

r is an integer from 0 to 2; and

* is a binding site.

In Formulae 2 and 3, Ar₁ and Ar₂ are each independently one of Formulae 4a to 4d below:

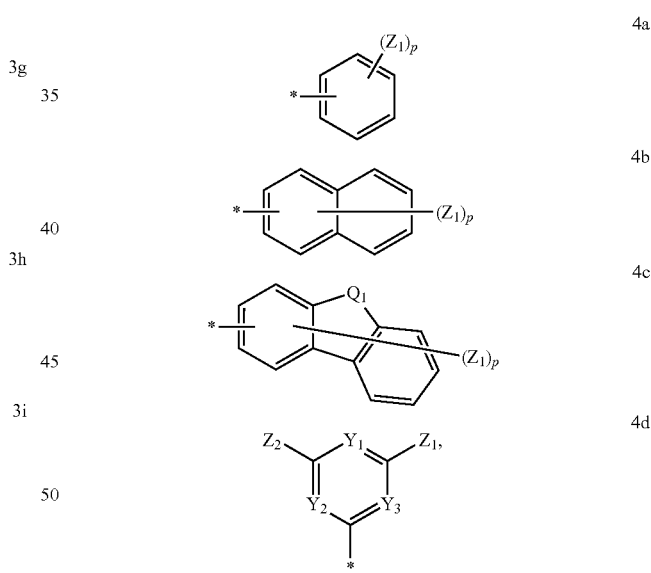

wherein $Q_1$ is a linking group represented by —C($R_{14}$)($R_{15}$)—, —N($R_{16}$)—, —S—, or —O—;

$Y_1$, $Y_2$ and $Y_3$ are each independently a linking group represented by —N= or —C($R_{17}$)=;

$Z_1$, $Z_2$, $R_{14}$, $R_{15}$, $R_{16}$, and $R_{17}$, are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

p is an integer from 1 to 8; and

* is a binding site.

In Formulae 2 and 3, $Ar_1$ and $Ar_2$ are each independently one of Formulae 5a to 5i below:

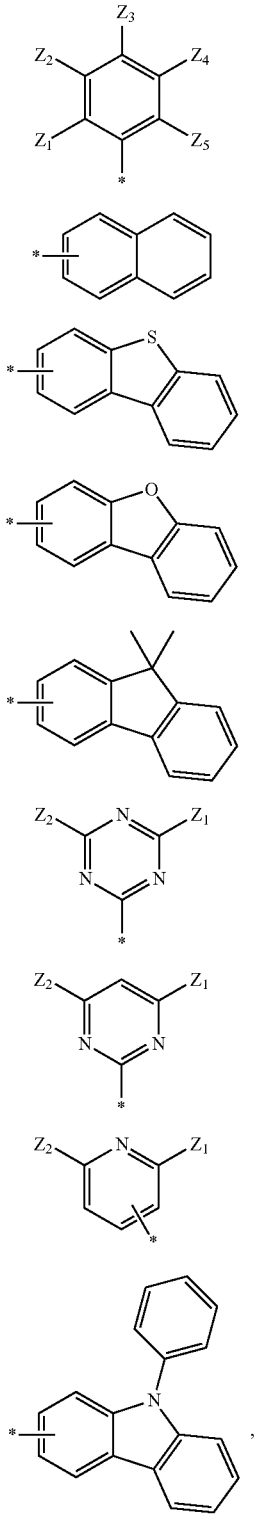

wherein $Z_1$ to $Z_5$ are each independently a hydrogen atom, a heavy hydrogen atom, a halogen atom, a cyano group, a substituted or unsubstituted C1-C20 alkyl group, a substituted or unsubstituted C1-C20 alkoxy group, a substituted or unsubstituted C5-C20 aryl group, a substituted or unsubstituted C3-C20 heteroaryl group, or a substituted or unsubstituted C6-C20 condensed polycyclic group; and

* is a binding site.

In Formulae 2 and 3, $Ar_3$ is one of Formulae 6a to 6e below:

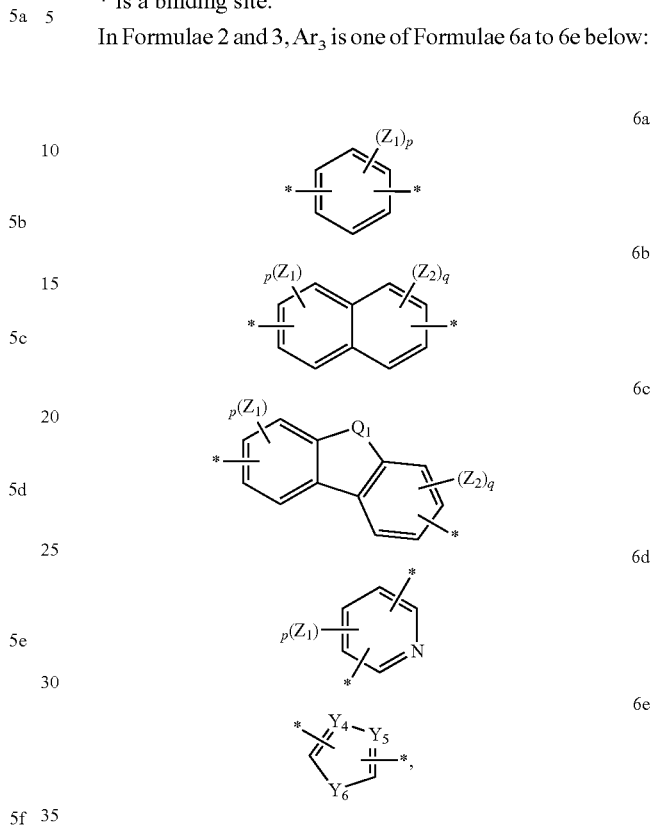

wherein $Q_1$ is a linking group represented by $-C(R_{14})(R_{15})-$, $-N(R_{16})-$, $-S-$, or $-O-$;

$Y_4$, $Y_5$ and $Y_6$ are each independently a linking group represented by $-O-$, $-S-$, $-N=$ or $-C(R_{17})=$;

$Z_1$, $Z_2$, $R_{14}$, $R_{15}$, $R_{16}$, and $R_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

p is an integer from 1 to 4;

q is an integer from 1 to 4; and

* is a binding site.

In Formulae 2 and 3, $X_1$ is one of Formulae 7a to 7k below:

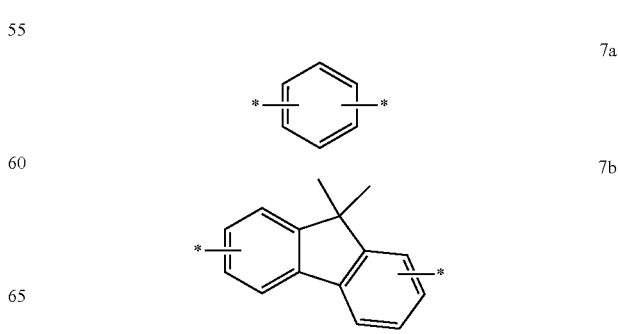

-continued
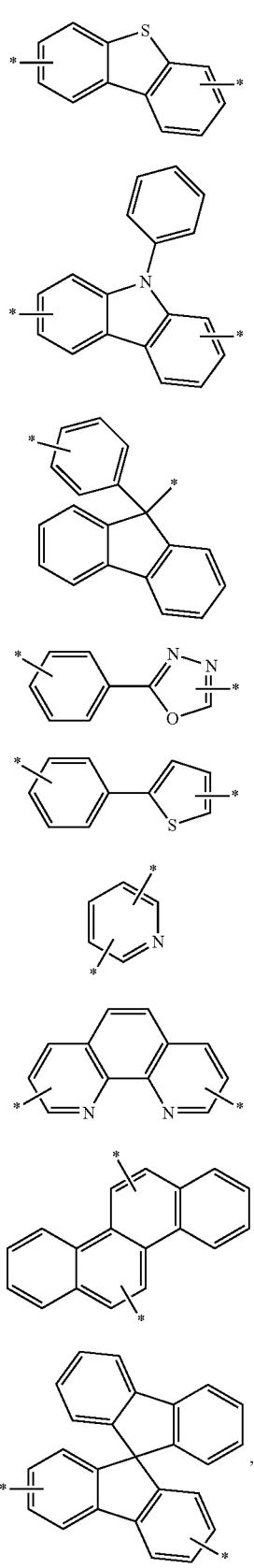
wherein * is a binding site.
The heterocyclic compound of Formula 1 may be one of the compounds below:
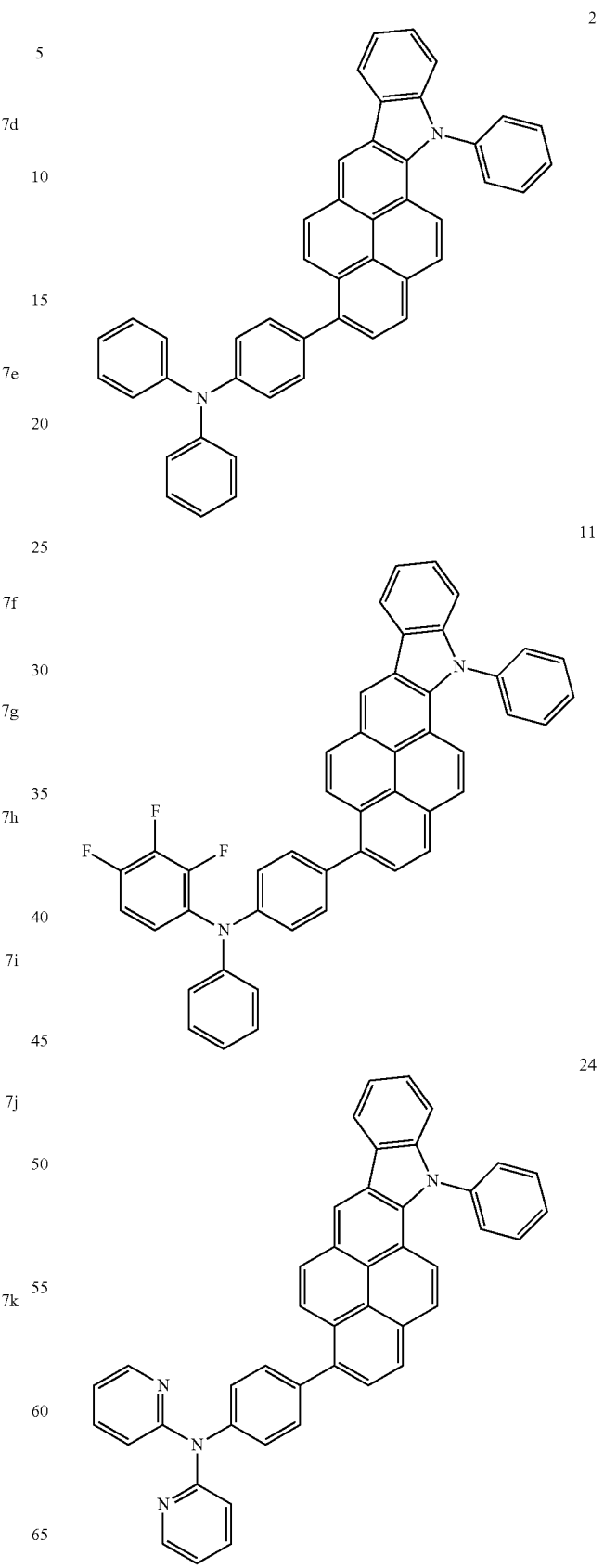

-continued
34
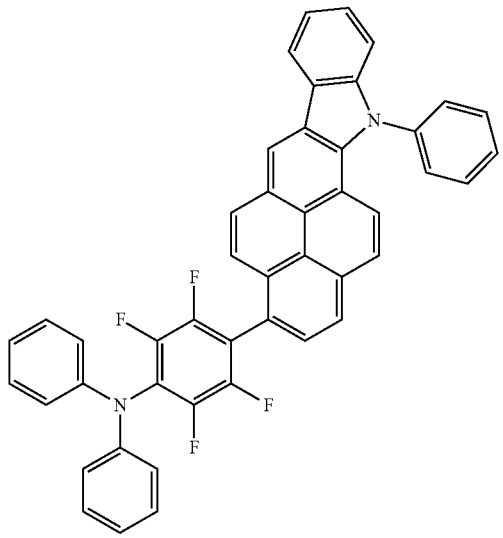
45
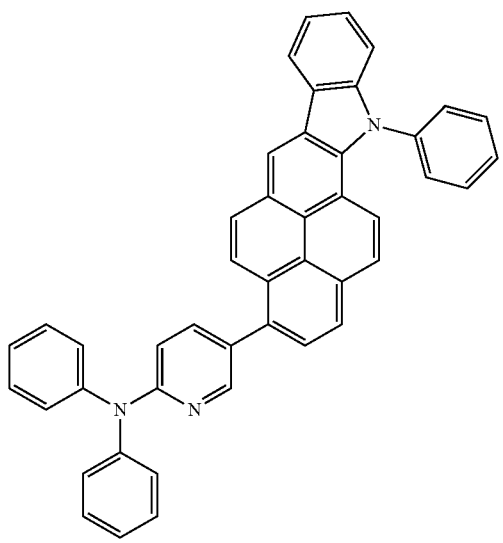
48
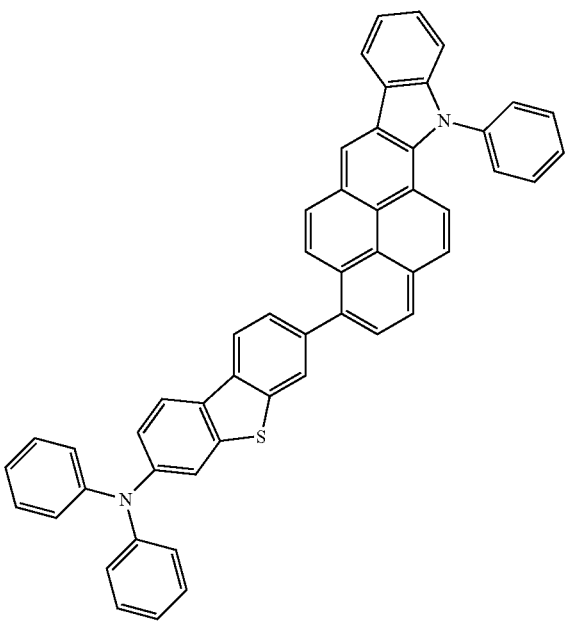
55
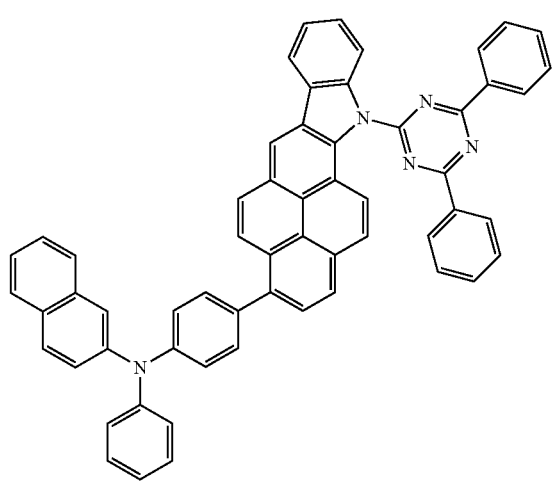

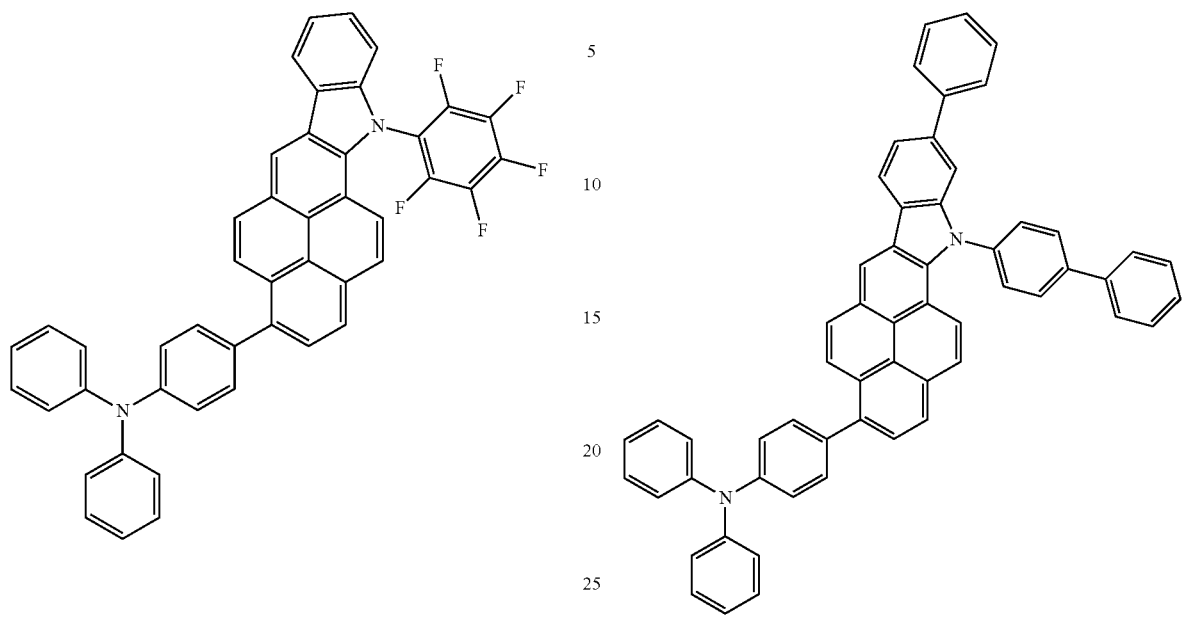
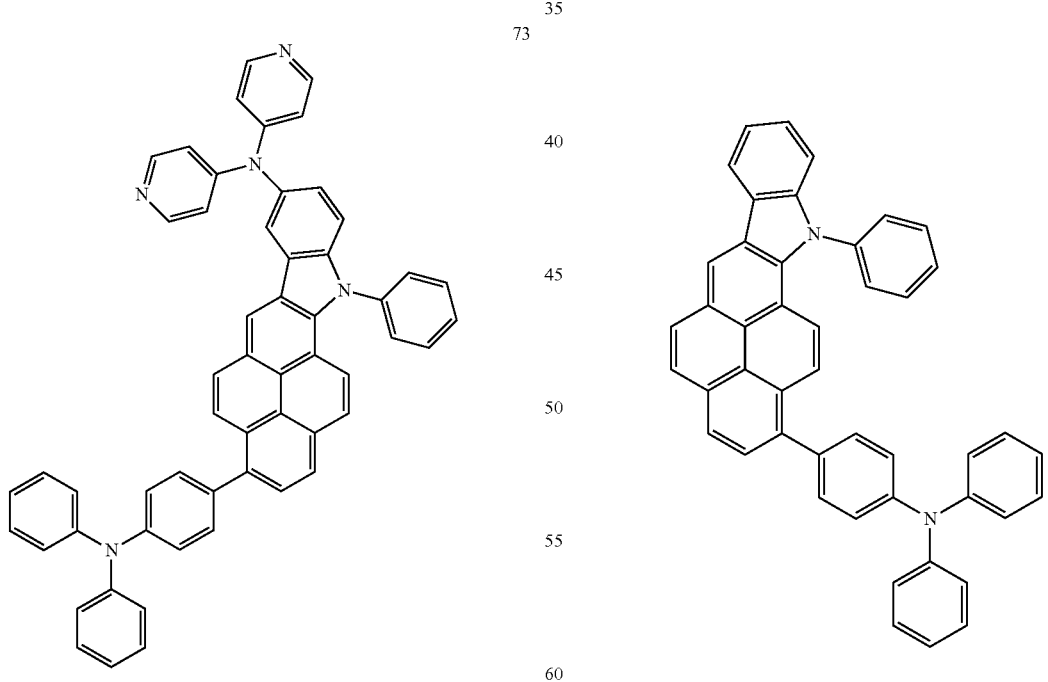

-continued
89
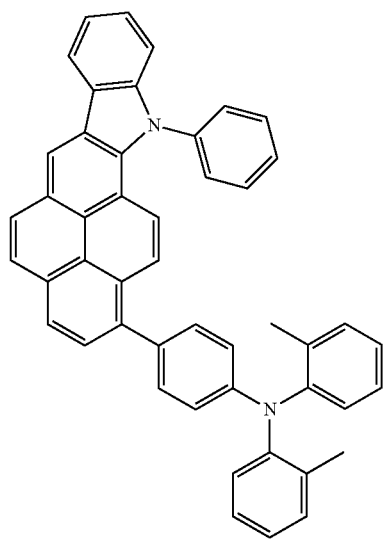
95
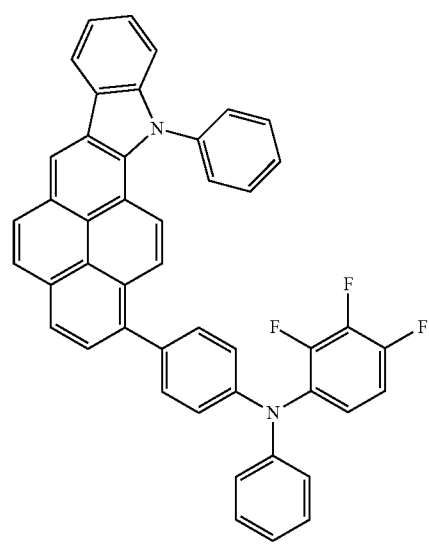
105
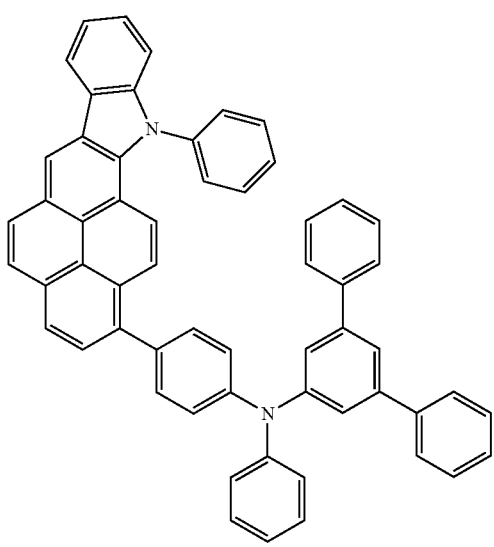
-continued
108
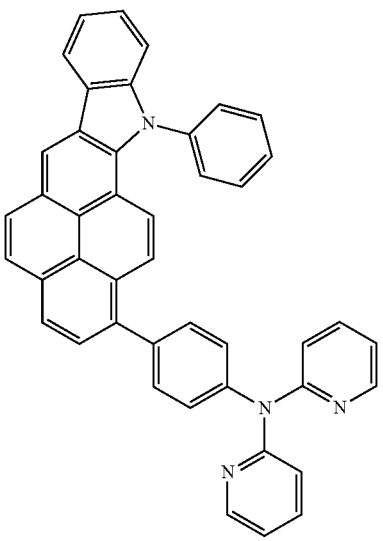
124
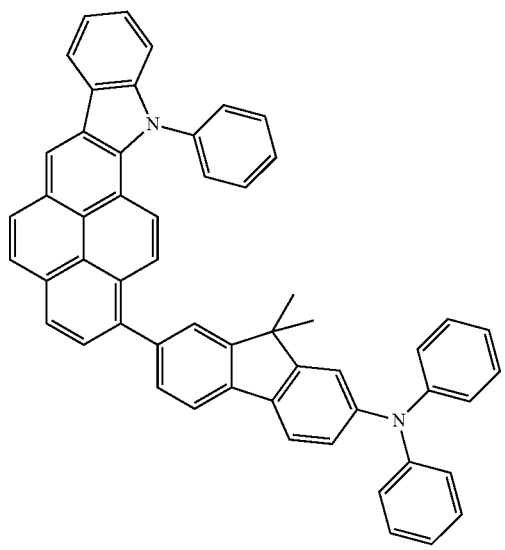
141
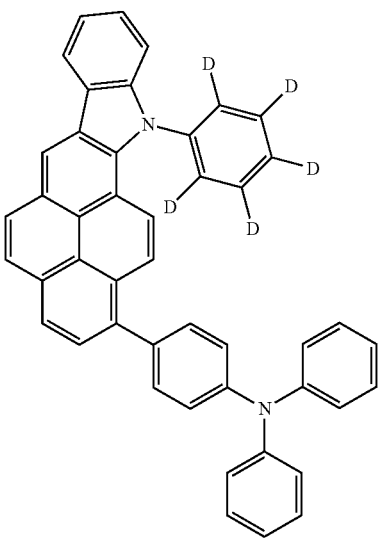

25
-continued

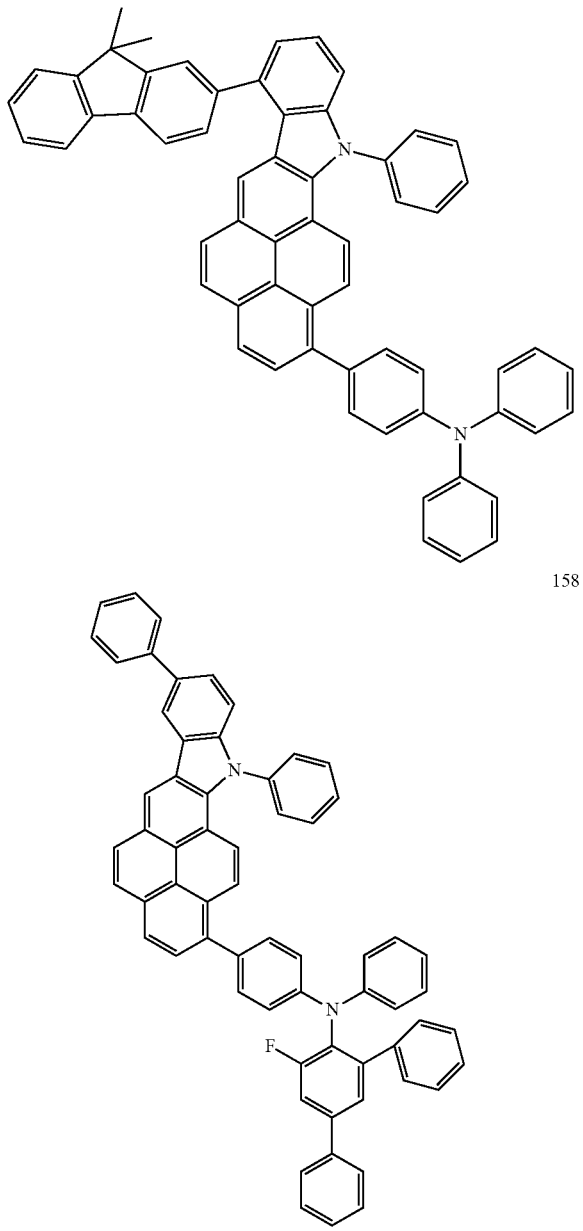

146

158

According to another aspect of the present invention, there is provided an organic light-emitting device including:
a first electrode;
a second electrode; and
an organic layer interposed between the first electrode and the second electrode,
wherein the organic layer includes a first layer including the heterocyclic compound.

The first layer may include a hole injection layer, a hole transport layer, a layer having both hole injecting and hole transporting capabilities, an emission layer, an electron injection layer, an electron transport layer, or a layer having both electron injecting and electron transporting capabilities.

The first layer may include a hole injection layer, a hole transport layer, a layer having both hole injecting and hole transporting capabilities, an emission layer, an electron injection layer, an electron transport layer, or a layer having both electron injecting and electron transporting capabilities, wherein the first layer further includes a charge-generating material.

The first layer may be formed of the heterocyclic compound by using a wet process.

According to another aspect of the present invention, there is provided a flat panel display device including the organic light-emitting device, wherein a first electrode of the organic light-emitting device is electrically connected to a source electrode or a drain electrode of a thin film transistor.

BRIEF DESCRIPTION OF THE DRAWINGS

The above and other features and advantages of the present invention will become more apparent by describing in detail exemplary embodiments thereof with reference to the attached drawing in which.

DETAILED DESCRIPTION OF THE INVENTION

Figure 1:
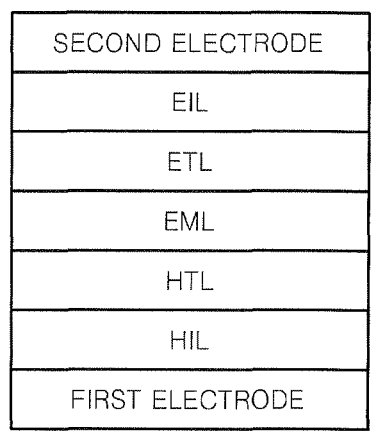
FIG. 1 illustrates an organic light-emitting device according to an embodiment of the present invention.
Figure 2:
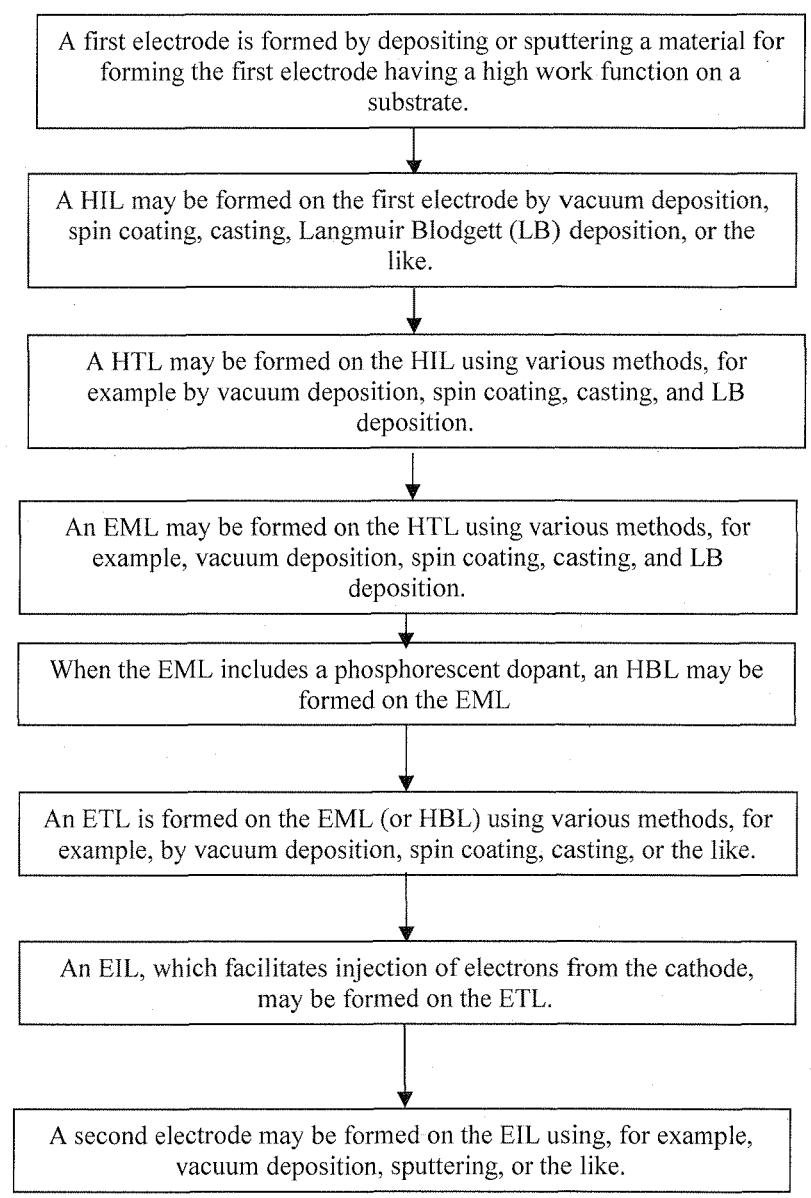
FIG. 2 shows a method of manufacturing an organic light-emitting device according to an embodiment of the present invention.

Hereinafter, the present invention will now be described more fully with reference to the accompanying drawing, in which an exemplary embodiment of the invention is shown.

For example, an organic light-emitting device manufactured using a compound of phenylanthracene dimer or trimer, as a material for forming an emission layer, is widely known. However, such organic light-emitting devices have a narrow energy gap and lower blue-light color purity since two or three oligomeric species of anthracene are linked by conjugation. In addition, such compounds are highly vulnerable to oxidation and thus are liable to produce impurities, necessitating purification. In order to overcome these drawbacks, organic light-emitting devices manufactured using an anthracene compound including naphthalene substituted for anthracene at 1,9 position or using a diphenylanthracene compound including an aryl group substituted for a phenyl group at m-position have been introduced. However, these organic light-emitting devices have a lower light-emission efficiency.

In addition, organic light-emitting devices manufactured using a naphthalene-substituted monoanthracene derivative have been introduced. However, the compound has a low light-emission efficiency of about 1 cd/A, and thus such organic light-emitting devices are not suitable for practical use.

Organic light-emitting devices manufactured using compounds having a phenylanthracene structure have also been introduced. However, these compounds are substituted with an aryl group at m-position, and thereby having a low light-emission efficiency of about 2 cd/A in spite of excellent thermal resistance.

The present invention will now be described in more detail.

According to an embodiment of the present invention, a heterocyclic compound represented by Formula 1 below is provided.

<Formula 1>

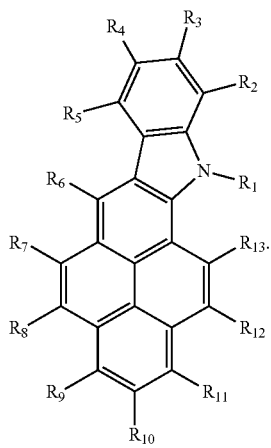

In Formula 1, $R_1$ to $R_{13}$ may be each independently a hydrogen atom, a heavy hydrogen atom, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C1-C60 alkoxy group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, a substituted or unsubstituted C6-C60 condensed polycyclic group, a halogen atom, a cyano group, a nitro group, a hydroxy group, or a carboxy group.

The heterocyclic compounds of Formula 1 according to an embodiment of the present invention may be suitable as a material for forming an emission layer, an electron transport layer, or an electron injection layer of an organic light-emitting device. The heterocyclic compound of Formula 1 having a heterocyclic group in the molecule thereof has a high glass transition temperature (Tg) or a high melting point due to an introduction of the heterocyclic group. Thus, the heterocyclic compound has high thermal resistance against Joule's heat generated in an organic layer, between organic layers, or between an organic layer and a metallic electrode when light emission occurs, and has high durability in a high-temperature environment.

An organic light-emitting device manufactured using the heterocyclic compound of Formula 1 has high durability when stored or operated. In addition, due to the inclusion of a substituent such as an aryl group or heteroaryl group, molecular layers formed as thin films may be maintained in good condition, thereby improving the characteristics of the organic light-emitting device.

In the heterocyclic compound according to the current embodiment, a nitrogen atom (N) is directly bonded to carbon at position 1 of pyrene. When an electric field that is applied to a device and excites the molecule of the heterocyclic compound into an excited state such as a radial anion or radical cation, the heterocyclic compound is stabilized by resonance of the nitrogen atom, so that the lifespan of the heterocyclic compound is increased in the device. In addition, unshared electron pair of the nitrogen are added to π-electrons of the pyrene backbone. As a result, light-emitting efficiency may be increased due to not only π→π* transition but also π→π* transition.

Substituents of the compound of Formula 1 will now be described in more detail.

According to an embodiment of the present invention, in Formula 1, $R_1$ to $R_5$ may be each independently a hydrogen atom, a heavy hydrogen atom, a halogen atom, a cyano group, a substituted or unsubstituted C1-C20 alkyl group, or one of Formulae 2a to 2i below:

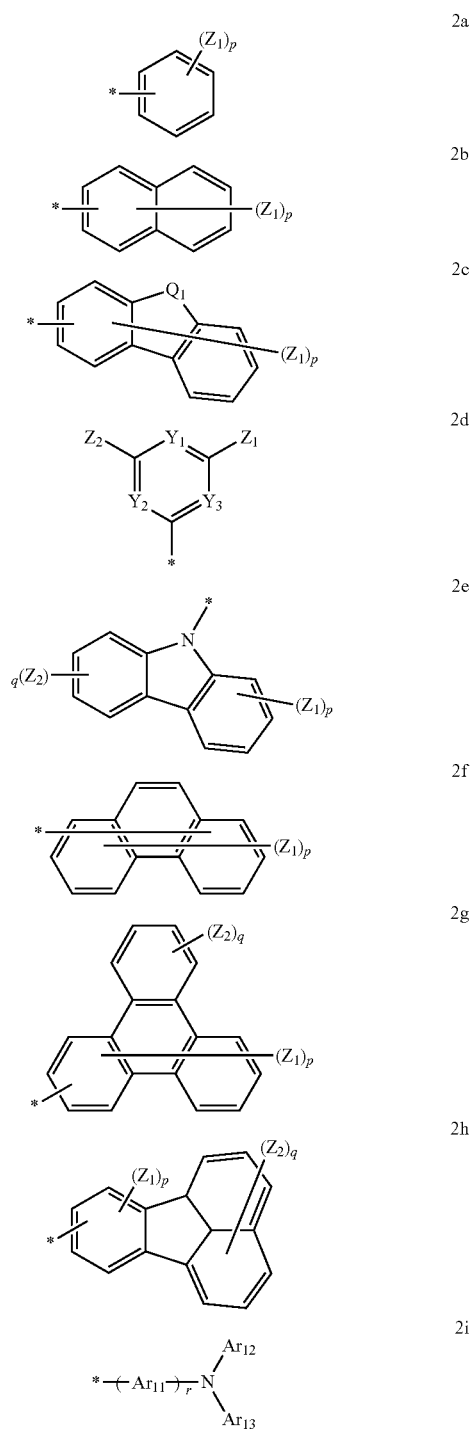

In Formulae 2a to 2i, $Q_1$ is a linking group represented by —$C(R_{14})(R_{15})$—, —$N(R_{16})$—, —S—, or —O—;

$Y_1$, $Y_2$ and $Y_3$ are each independently a linking group represented by —N= or —C($R_{17}$)=;

$Z_1$, $Z_2$, $Ar_{12}$, $Ar_{13}$, $R_{14}$, $R_{15}$, and $R_{16}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

$Ar_{11}$ is a substituted or unsubstituted C1-C20 alkylene group, a substituted or unsubstituted C5-C20 arylene group, or a substituted or unsubstituted C3-C20 heteroarylene group;

p is an integer from 1 to 12;

q is an integer from 1 to 12;

r is an integer from 0 to 5; and

* is a binding site.

According to an embodiment of the present invention, in Formula 1, $R_1$ to $R_5$ may be each independently a hydrogen atom, a heavy hydrogen atom, a halogen atom, a cyano group, a methyl group, an ethyl group, a propyl group, a butyl group, a t-butyl group, a pentyl group, or one of Formulae 3a to 3m below:

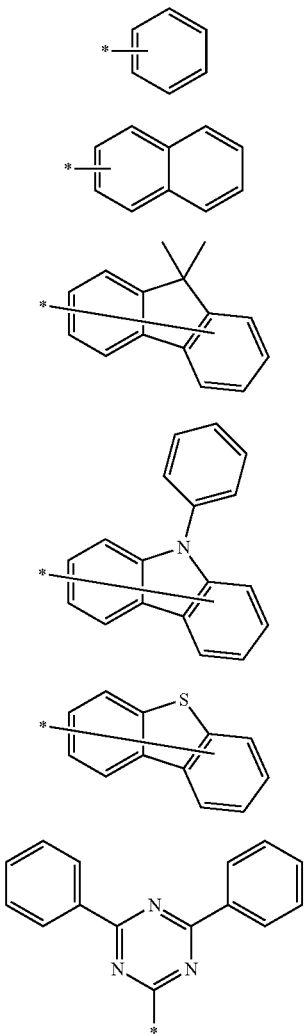

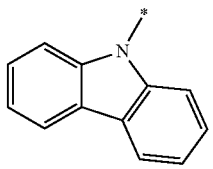

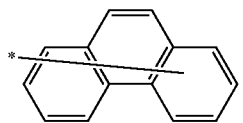

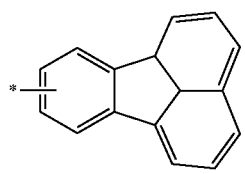

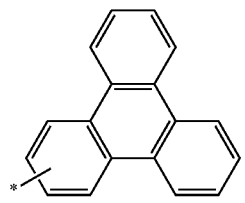

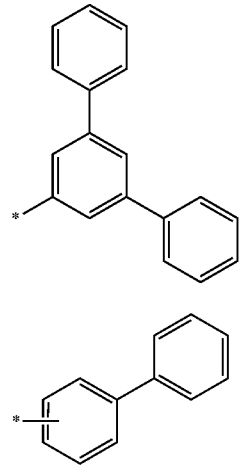

Formulae 3a to 3m, $Ar_{12}$ and $Ar_{13}$ are each independently a substituted or unsubstituted C5-C20 aryl group, a substituted or unsubstituted C3-C20 heteroaryl group, or a substituted or unsubstituted C6-C20 condensed polycyclic group;

r is an integer from 0 to 2; and

* is a binding site.

According to an embodiment of the present invention, in Formula 1, $R_6$ to $R_8$ and $R_{10}$ to $R_{13}$ may be each independently a hydrogen atom or a heavy hydrogen atom, and $R_9$ may be —$X_1$—N($Ar_1Ar_2$) that is a substituted C5-C60 aryl group, a substituted C3-C60 heteroaryl group, or a substituted C6-C60 condensed polycyclic group.

Alternatively, $R_6$ to $R_{10}$, $R_{12}$ and $R_{13}$ may be each independently a hydrogen atom or a heavy hydrogen atom, and $R_{11}$ may be —X₁—N(Ar₁Ar₂) that is a substituted C5-C60 aryl group, a substituted C3-C60 heteroaryl group, or a substituted C6-C60 condensed polycyclic group.

In this regard, X₁ may be a divalent linking group represented by —(Ar₃)ₙ—, wherein Ar₃ may be a substituted or unsubstituted C5-C60 arylene group, a substituted or unsubstituted C3-C60 heteroarylene group, or a substituted or unsubstituted C6-C60 condensed polycyclic group, and n is an integer from 1 to 10.

The Ar₃'s may be the same or different.

At least two adjacent Ar₃'s may be fused or linked to each other via a single bond.

Ar₁ and Ar₂ are each independently one of Formulae 4a to 4d below:

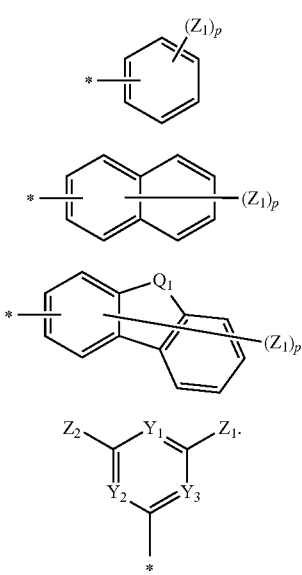

In Formulae 4a to 4d, Q₁ is a linking group represented by —C(R₁₄)(R₁₅)—, —N(R₁₆)—, —S—, or —O—;

Y₁, Y₂ and Y₃ are each independently a linking group represented by —N= or —C(R₁₇)=;

Z₁, Z₂, R₁₄, R₁₅, R₁₆, and R₁₇ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

p is an integer from 1 to 8; and

* is a binding site.

According to an embodiment of the present invention, in Formula 1, R₆ to R₈ and R₁₀ to R₁₃ may be each independently a hydrogen atom or a heavy hydrogen atom, and R₉ may be —X₁—N(Ar₁Ar₂) that is a substituted C5-C60 aryl group, a substituted C3-C60 heteroaryl group, or a substituted C6-C60 condensed polycyclic group.

Alternatively, R₆ to R₁₀, R₁₂, and R₁₃ may be each independently a hydrogen atom or a heavy hydrogen atom, and R₁₁ may be —X₁—N(Ar₁Ar₂) that is a substituted C5-C60 aryl group, a substituted C3-C60 heteroaryl group, or a substituted C6-C60 condensed polycyclic group.

In this regard, X₁ may be a divalent linking group represented by —(Ar₃)ₙ—, wherein Ar₃ may be a substituted or unsubstituted C5-C60 arylene group, a substituted or unsubstituted C3-C60 heteroarylene group, or a substituted or unsubstituted C6-C60 condensed polycyclic group, and n is an integer from 1 to 10.

The Ar₃'s may be the same or different.

At least two adjacent Ar₃'s may be fused or linked to each other via a single bond.

Ar₁ and Ar₂ are each independently one of Formulae 5a to 5i below:

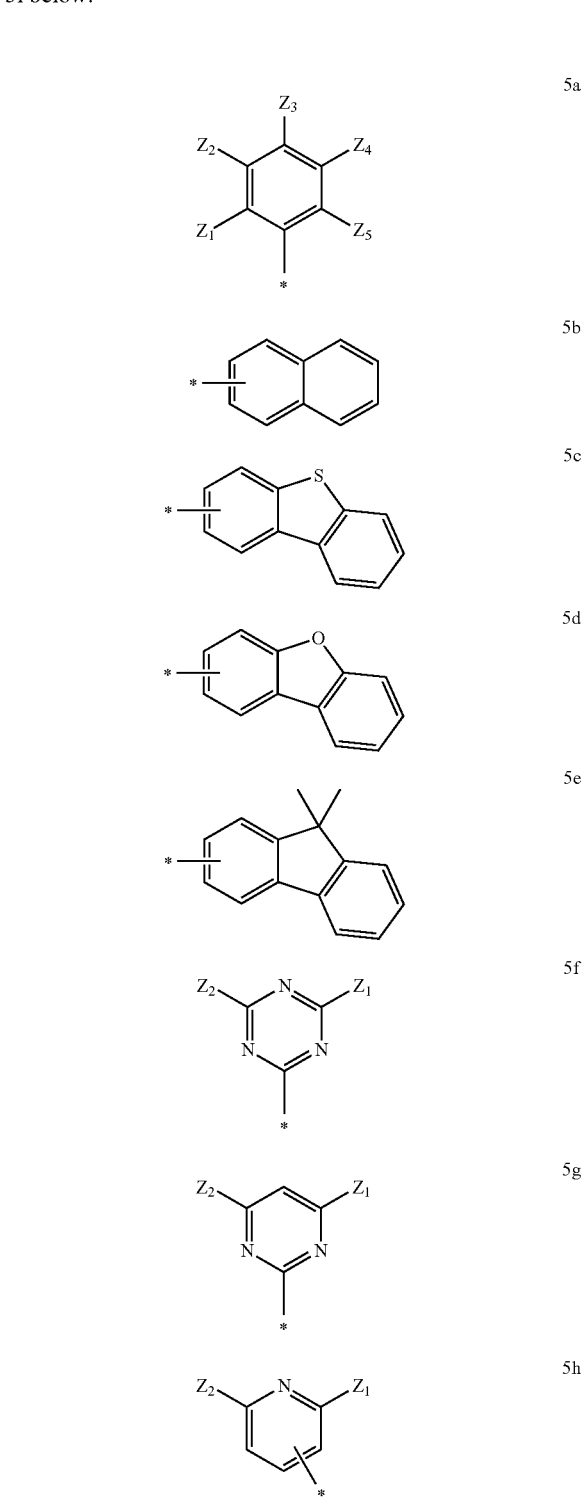

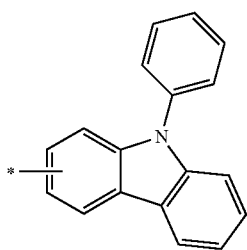

5i

In Formulae 5a to 5i, $Z_1$ to $Z_5$ are each independently a hydrogen atom, a heavy hydrogen atom, a halogen atom, a cyano group, a substituted or unsubstituted C1-C20 alkyl group, a substituted or unsubstituted C1-C20 alkoxy group, a substituted or unsubstituted C5-C20 aryl group, a substituted or unsubstituted C3-C20 heteroaryl group, or a substituted or unsubstituted C6-C20 condensed polycyclic group; and

* is a binding site.

According to an embodiment of the present invention, in Formula 1, $R_9$ or $R_{11}$ may be each independently —$X_1$—N($Ar_1Ar_2$) that is a substituted C5-C60 aryl group, a substituted C3-C60 heteroaryl group, or a substituted C6-C60 condensed polycyclic group.

In this regard, $Ar_1$ and $Ar_2$ are each independently a substituted or unsubstituted C3-C50 cycloalkyl group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, or a substituted or unsubstituted C6-C60 condensed polycyclic group;

$X_1$ may be a divalent linking group represented by —$(Ar_3)_n$—, wherein $Ar_3$ is one of Formulae 6a to 6e, the $Ar_3$'s may be the same or different, and at least two adjacent $Ar_3$'s may be fused or linked to each other via a single bond.

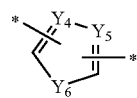

6e

In Formulae 6a to 6e, $Q_1$ is a linking group represented by —C($R_{14}$)($R_{15}$)—, —N($R_{16}$)—, —S—, or —O—;

$Y_4$, $Y_5$ and $Y_6$ are each independently a linking group represented by —O—, —S—, —N= or —C($R_{17}$)=;

$Z_1$, $Z_2$, $R_{14}$, $R_{15}$, $R_{16}$, and $R_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

p is an integer from 1 to 4;

q is an integer from I to 4; and

* is a binding site.

According to an embodiment of the present invention, in Formula 1, $R_9$ or $R_{11}$ may be each independently —$X_1$—N($Ar_1Ar_2$) that is a substituted C5-C60 aryl group, a substituted C3-C60 heteroaryl group, or a substituted C6-C60 condensed polycyclic group.

In this regard, $Ar_1$ and $Ar_3$ are each independently a substituted or unsubstituted C3-C50 cycloalkyl group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, or a substituted or unsubstituted C6-C60 condensed polycyclic group; and $X_1$ is one of Formulae 7a to 7k below:

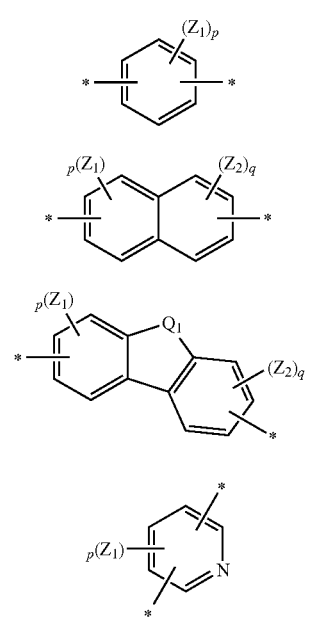

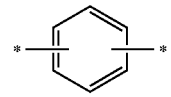

7a

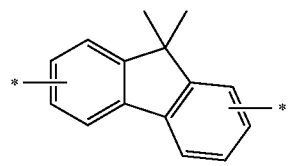

7b

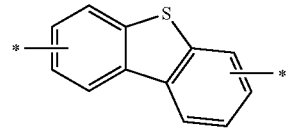

7c

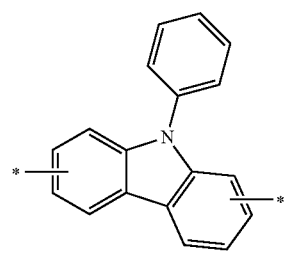

7d

-continued

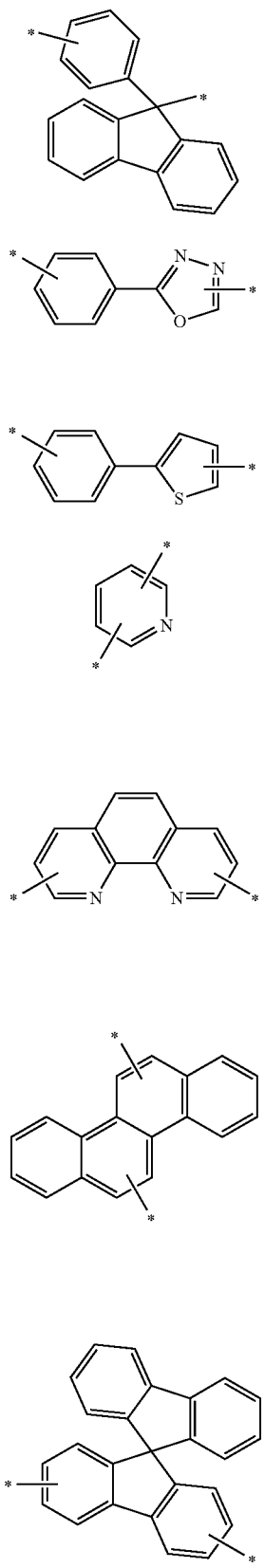

In Formulae 7a to 7k, * is a binding site.

According to an embodiment of the present invention, the heterocyclic compound of Formula 1 may be represented by Formula 2 or Formula 3 below:

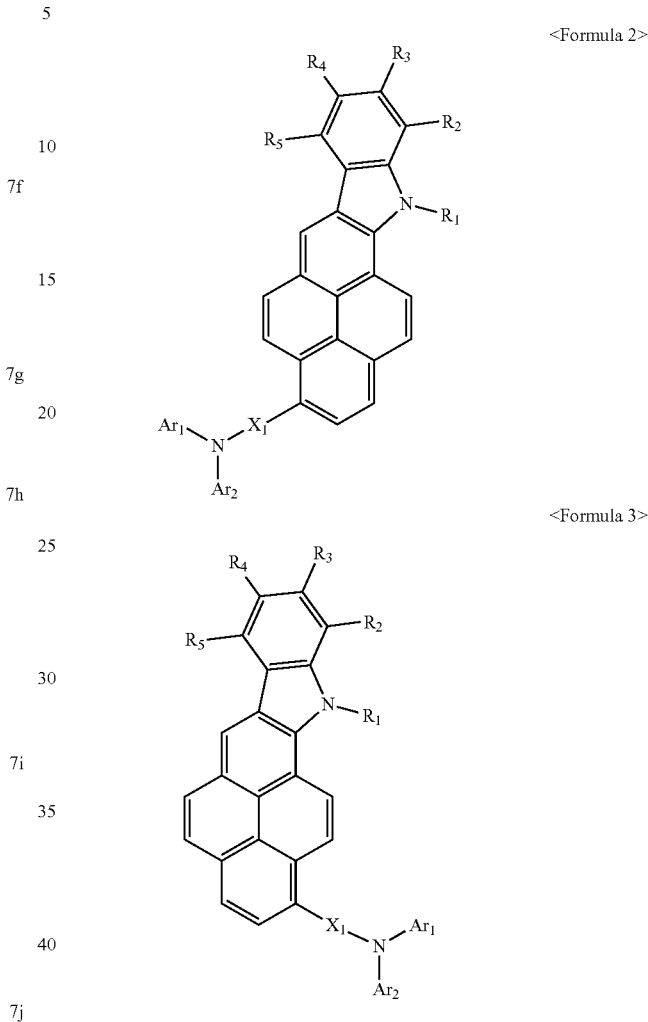

<Formula 2>

<Formula 3>

In Formulae 2 and 3, $R_1$ to $R_5$ are each independently a hydrogen atom, a heavy hydrogen atom, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C1-C60 alkoxy group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, a substituted or unsubstituted C6-C60 condensed polycyclic group, a halogen atom, a cyano group, a nitro group, a hydroxy group, or a carboxy group;

$Ar_1$ and $Ar_2$ are each independently a substituted or unsubstituted C3-C50 cycloalkyl group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, or a substituted or unsubstituted C6-C60 condensed polycyclic group;

$X_1$ is a divalent linking group represented by $—(Ar_3)_n—$, wherein $Ar_3$ is a substituted or unsubstituted C5-C60 arylene group, a substituted or unsubstituted C3-C60 heteroarylene group, or a substituted or unsubstituted C6-C60 condensed polycyclic group, and n is an integer from 1 to 10;

the $Ar_3$'s may be the same or different; and at least two adjacent $Ar_3$'s may be fused or linked to each other via a single bond.

According to an embodiment of the present invention, in Formulae 2 and 3, $R_1$ to $R_5$ may be each independently a hydrogen atom, a heavy hydrogen atom, a halogen atom, a cyano group, a substituted or unsubstituted C1-C20 alkyl group, or one of Formulae 2a to 2i below:

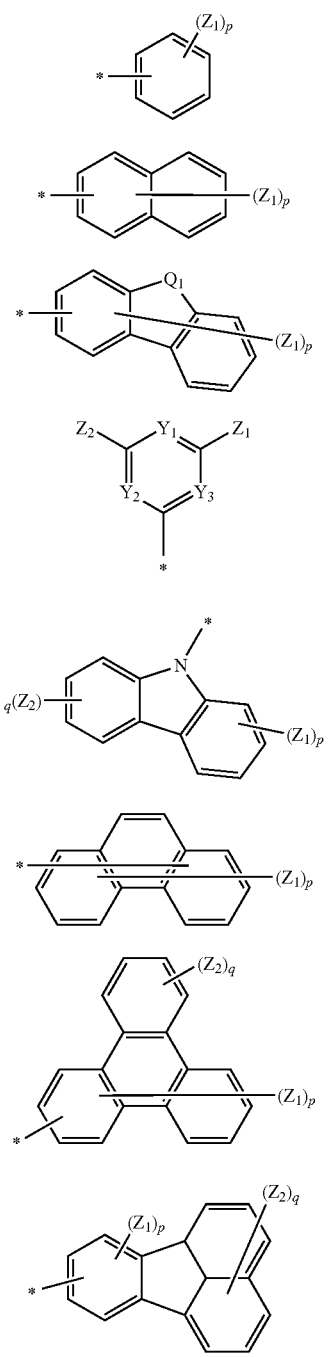

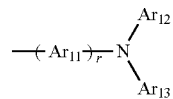

In Formulae 2a to 2i, $Q_1$ is a linking group represented by —$C(R_{14})(R_{15})$—, —$N(R_{16})$—, —S—, or —O—;

$Y_1$, $Y_2$ and $Y_3$ are each independently a linking group represented by —N= or —$C(R_{17})$=;

$Z_1$, $Z_2$, $Ar_{12}$, $Ar_{13}$, $R_{14}$, $R_{15}$, $R_{16}$, and $R_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

$Ar_{11}$ is a substituted or unsubstituted C1-C20 alkylene group, a substituted or unsubstituted C5-C20 arylene group, or a substituted or unsubstituted C3-C20 heteroarylene group;

p is an integer from 1 to 12;
q is an integer from 1 to 12;
r is an integer from 0 to 5; and
* is a binding site.

According to an embodiment of the present invention, in Formulae 2 and 3, $R_1$ to $R_5$ may be each independently a hydrogen atom, a heavy hydrogen atom, a halogen atom, a cyano group, a methyl group, an ethyl group, a propyl group, a butyl group, a t-butyl group, a pentyl group, or one of Formulae 3a to 3m below:

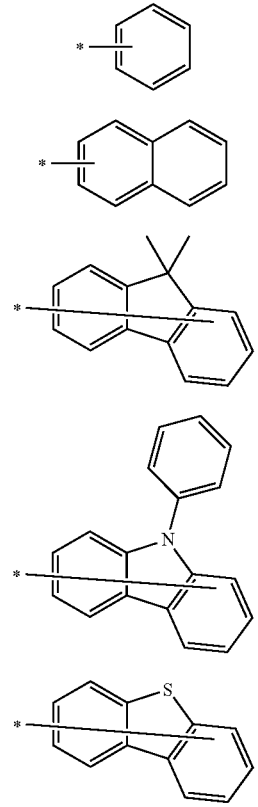

-continued

3f
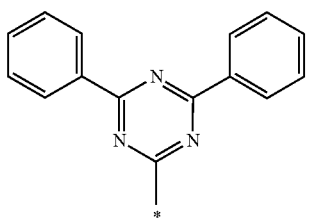

3g
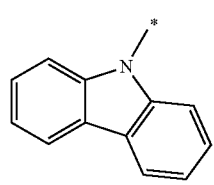

3h
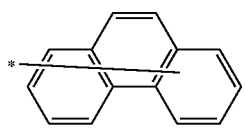

3i
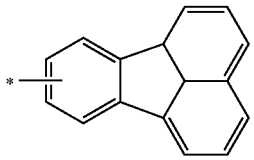

3j
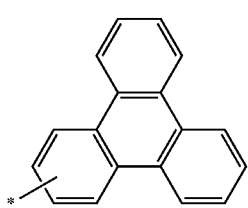

3k
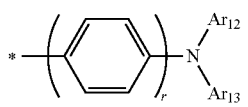

3l
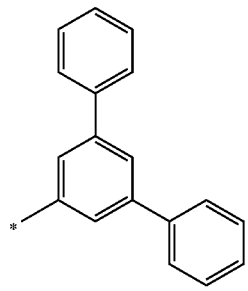

3m
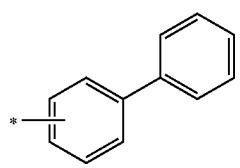

In Formula 3a to 3m, $Ar_{12}$ and $Ar_{13}$ are each independently a substituted or unsubstituted C5-C20 aryl group, a substituted or unsubstituted C3-C20 heteroaryl group, or a substituted or unsubstituted C6-C20 condensed polycyclic group;

r is an integer from 0 to 2; and

* is a binding site.

According to an embodiment of the present invention, in Formulae 2 and 3, $Ar_1$ and $Ar_2$ may be each independently one of Formulae 4a to 4d below:

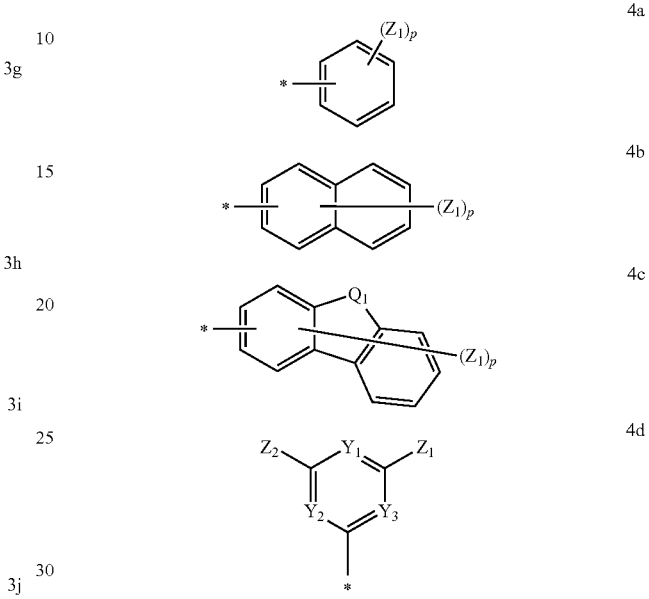

In Formulae 4a to 4d, $Q_1$ is a linking group represented by —$C(R_{14})(R_{15})$—, —$N(R_{16})$—, —S—, or —O—;

$Y_1$, $Y_2$ and $Y_3$ are each independently a linking group represented by —N= or —$C(R_{17})$=;

$Z_1$, $Z_2$, $R_{14}$, $R_{15}$, $R_{16}$, and $R_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

p is an integer from 1 to 8; and

* is a binding site.

According to an embodiment of the present invention, in Formulae 2 and 3, $Ar_1$ and $Ar_2$ may be each independently one of Formulae 5a to 5i.

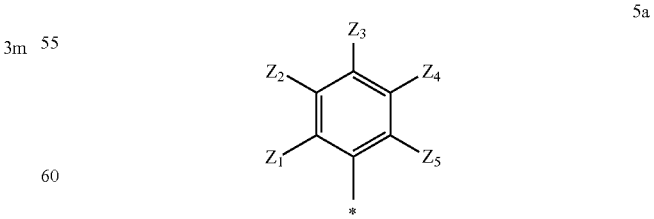

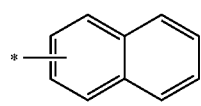

-continued

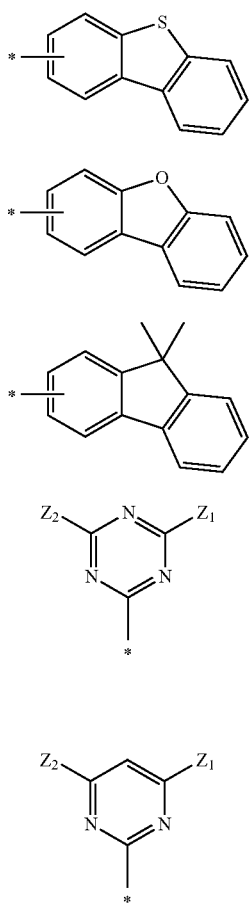

5c

5d

5e

5f

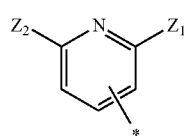

5g

5h

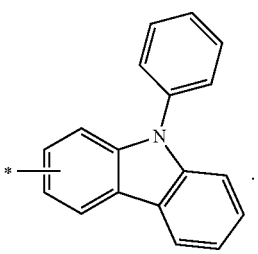

5i

In Formulae 5a to 5i, $Z_1$ to $Z_5$ are each independently a hydrogen atom, a heavy hydrogen atom, a halogen atom, a cyano group, a substituted or unsubstituted C1-C20 alkyl group, a substituted or unsubstituted C1-C20 alkoxy group, a substituted or unsubstituted C5-C20 aryl group, a substituted or unsubstituted C3-C20 heteroaryl group, or a substituted or unsubstituted C6-C20 condensed polycyclic group; and

* is a binding site.

According to an embodiment of the present invention, in Formulae 2 and 3, $Ar_3$ is one of Formulae 6a to 6e.

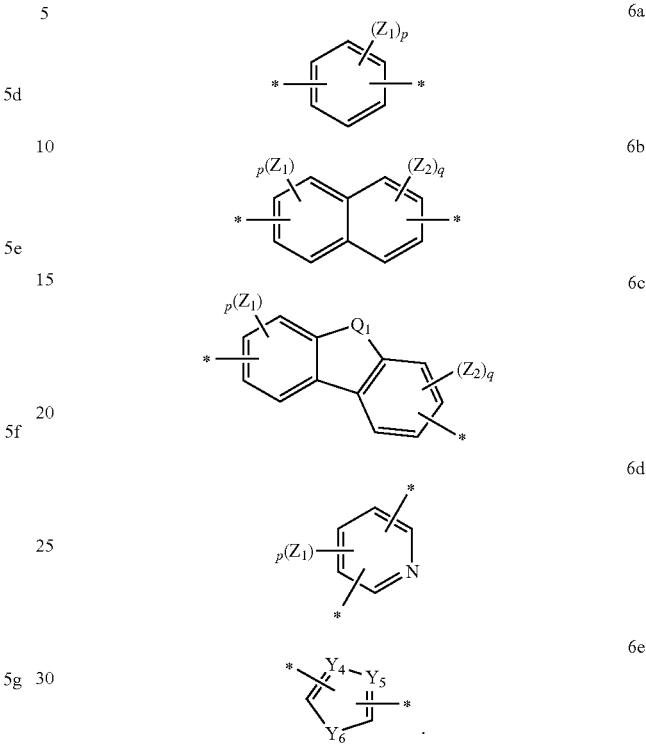

6a

6b

6c

6d

6e

In Formulae 6a to 6e, $Q_1$ is a linking group represented by —C($R_{14}$)($R_{15}$)—, —N($R_{16}$)—, —S—, or —O—;

$Y_4$, $Y_5$ and $Y_6$ are each independently a linking group represented by —O, —S, —N═ or —C($R_{17}$)═;

$Z_1$, $Z_2$, $R_{14}$, $R_{15}$, $R_{16}$, and $R_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

p is an integer from 1 to 4;
q is an integer from 1 to 4; and
* is a binding site.

According to an embodiment of the present invention, in Formulae 2 and 3, $X_1$ may be one of Formulae 7a to 7k below.

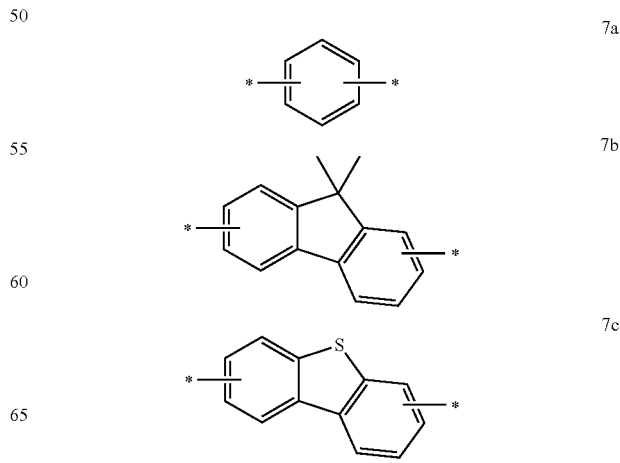

7a

7b

7c

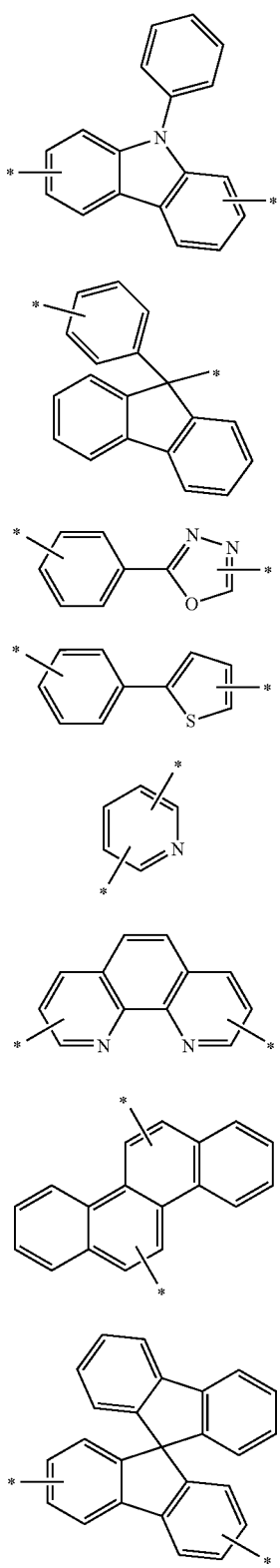

In Formulae 7a to 7k, * is a binding site.

Hereinafter, substituents described with reference to Formulae 1 to 3 will now be described in detail. In this regard, the numbers of carbon atoms in substituents are presented only for illustrative purposes and do not limit the characteristics of the substituents.

The unsubstituted C1-C50 alkyl group used herein may be linear or branched. Examples of the alkyl group include, but are not limited to, methyl, ethyl, propyl, isobutyl, sec-butyl, pentyl, iso-amyl, hexyl, heptyl, octyl, nonanyl, and dodecyl. At least one hydrogen atom of the alkyl group may be substituted with a heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a C1-C10 alkyl group, a C1-C10 alkoxy group, a C2-C10 alkenyl group, a C2-C10 alkynyl group, a C6-C16 aryl group, or a C4-C16 heteroaryl group.

The unsubstituted C2-C60 alkenyl group used herein refers to a hydrocarbon chain having at least one carbon-carbon double bond within or at a terminal of the unsubstituted alkyl group. Examples of the C2-C60 alkenyl group include ethenyl, propenyl, and butenyl. At least one hydrogen atom of the alkenyl group may be substituted with the same substituent groups as described above in connection with the alkyl group.

The unsubstituted C2-C60 alkynyl group used herein refers to a hydrocarbon chain having at least one carbon-carbon triple bond within or at a terminal of the alkyl group. Examples of the unsubstituted C2-C60 alkynyl group include acetylene, propylene, phenylacetylene, naphthylacetylene, isopropylacetylene, t-butylacetylene, and diphenylacetylene. At least one hydrogen atom of the alkynyl group may be substituted with the same substituent groups as described above in connection with the alkyl group.

The unsubstituted C3-C50 cycloalkyl group used herein refers to a C3-C50 cyclic alkyl group wherein at least one hydrogen atom in the cycloalkyl group may be substituted with the same substituent group described above in connection with the C1-C50 alkyl group.

The unsubstituted C1-C50 alkoxy group used herein is a group having a structure of —OA wherein A is an unsubstituted C1-C50 alkyl group as described above. Examples of the C1-C6-alkoxy group include methoxy, ethoxy, propoxy, isopropyloxy, butoxy, and pentoxy. At least one hydrogen atom of the alkoxy group may be substituted with the same substituent groups as described above in connection with the alkyl group.

The unsubstituted C5-C60 aryl group used herein refers to a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with the same substituent groups described with reference to the C1-C50 alkyl group.

Examples of the substituted or unsubstituted C5-C60 aryl group include a phenyl group, a C1-C10 alkylphenyl group (for example, ethylphenyl group), a halophenyl group (for example, o-, m-, and p-fluorophenyl group, and dichlorophenyl group), a cyanophenyl group, a dicyanophenyl group, a trifluoromethoxyphenyl group, a biphenyl group, a halobiphenyl group, a cyanobiphenyl group, a C1-C10 alkyl biphenyl group, a C1-C10 alkoxybiphenyl group, an o-, m-, and p-toryl group, an o-, m-, and p-cumenyl group, a mesityl group, a phenoxyphenyl group, an (α,α-dimethylbenzene) phenyl group, an (N,N'-dimethyl)aminophenyl group, an (N,N'-diphenyl)aminophenyl group, a pentalenyl group, an indenyl group, a naphthyl group, a halonaphthyl group (for example, fluoronaphthyl group), a C1-C10 alkylnaphthyl group (for example, methylnaphthyl group), a C1-C10 alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted C3-C60 heteroaryl group used herein includes one, two or three hetero atoms selected from the group consisting of N, O, P and S. At least two rings may be fused to each other or linked to each other by a single bond. Examples of the unsubstituted C3-C60 heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group. In addition, at least one hydrogen atom in the heteroaryl group may be substituted with the same substituent groups described above with reference to the C1-C50 alkyl group.

The unsubstituted C5-C50 aryloxy group is represented by —OA$_1$ wherein A$_1$ may be a C5-C50 aryl group. Examples of the aryloxy group include a phenoxy group. At least one hydrogen atom in the aryloxy group may be substituted with the same substituent groups described with reference to the C1-C50 alkyl group.

The unsubstituted C5-C50 arylthio group is represented by —SA$_1$ where A$_1$ may be a C5-C50 aryl group. Examples of the arylthio group include a benzenethio group and a naphthylthio group. At least one hydrogen atom in the arylthio group may be substituted with the same substituent groups described with reference to the C1-C50 alkyl group.

The unsubstituted C6-C60 condensed polycyclic group is a substituent including at least two rings wherein at least one aromatic ring and at least one non-aromatic ring are fused to each other or a substituent including an unsaturated ring but not having a conjugation structure. The condensed polycyclic group is distinguished from the aryl group or heteroaryl group since the condensed polycyclic group does not have an aromaticity.

Examples of the heterocyclic compound of Formula 1 according to the current embodiment of may include Compounds 1 through 158 represented below. However, the heterocyclic compound of Formula 1 is not limited thereto.

1

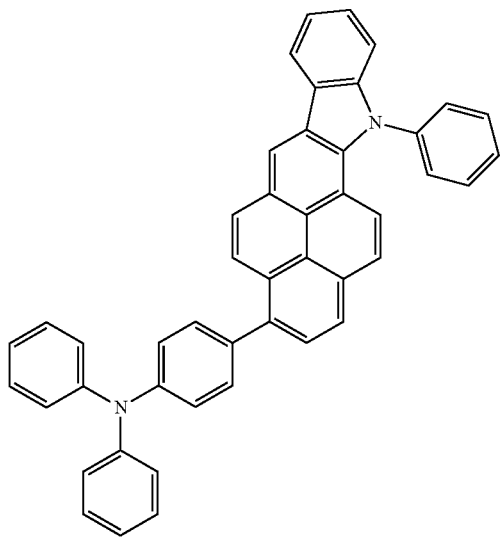

2

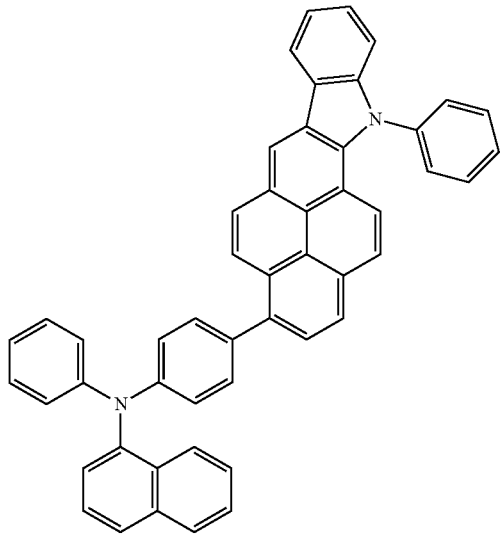

3

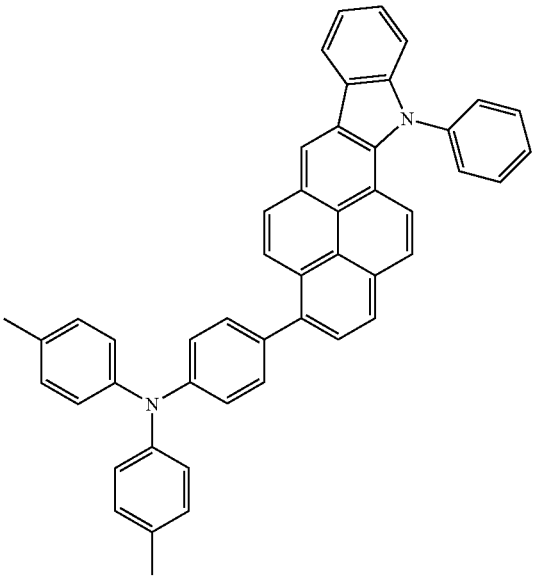

4

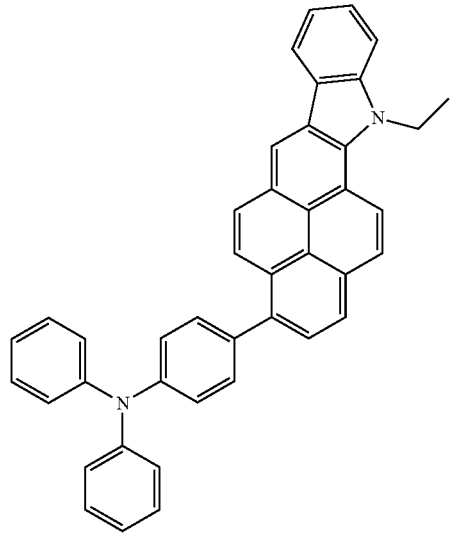

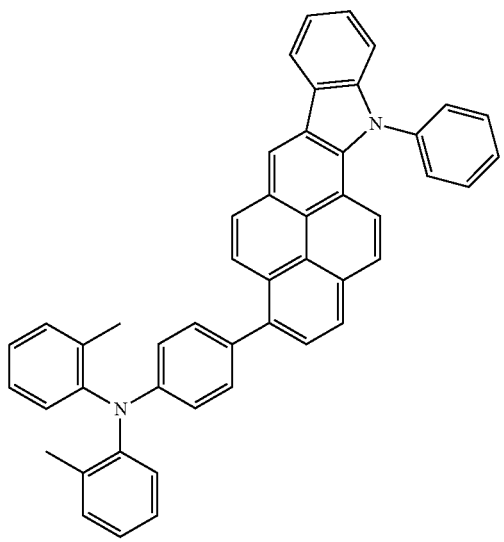
5
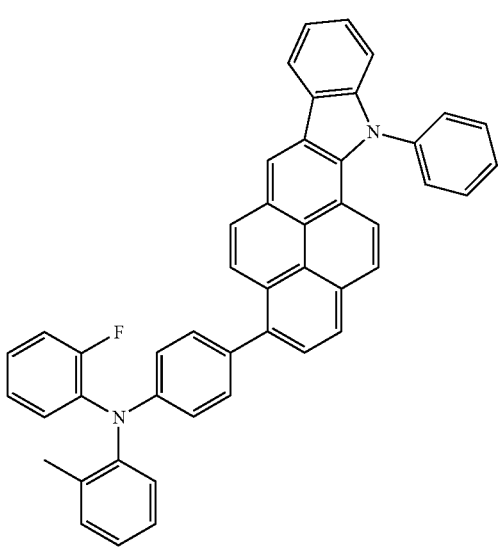
8
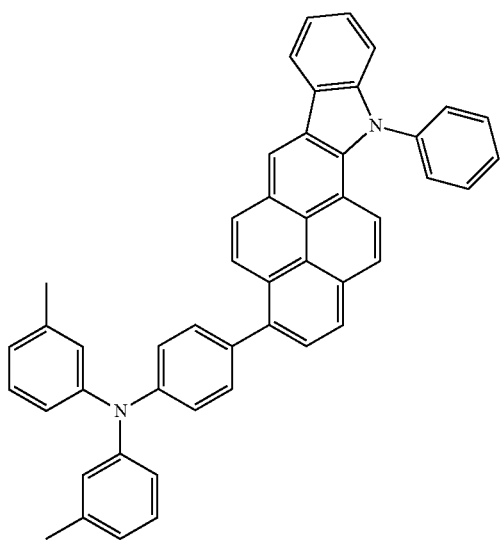
6
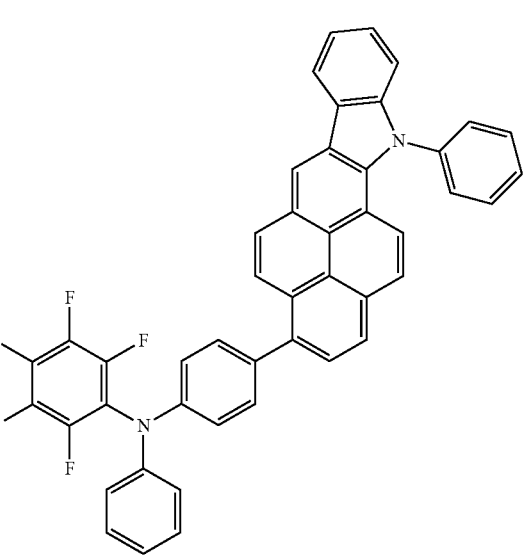
9
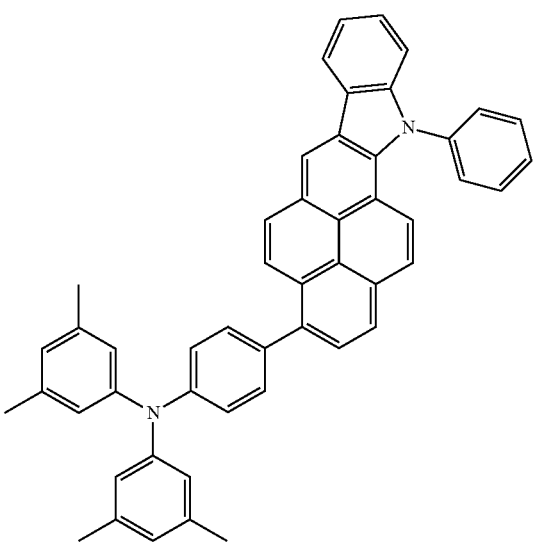
7
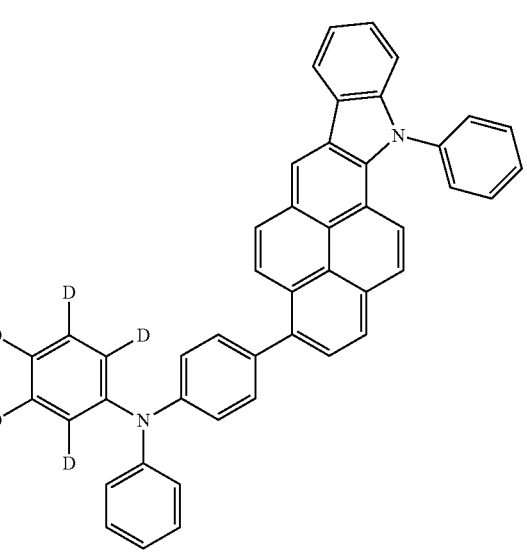
10

11
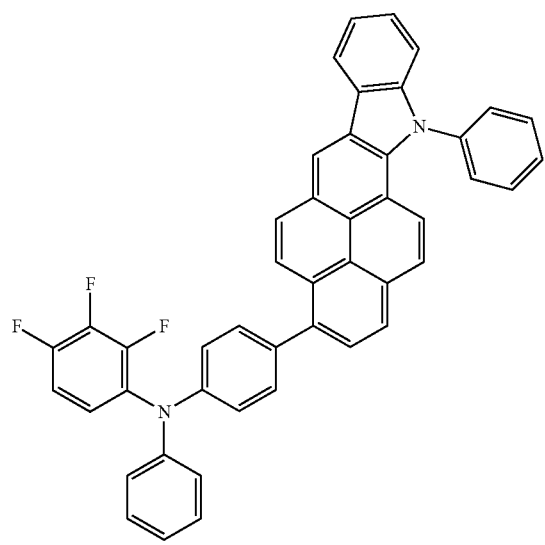
12
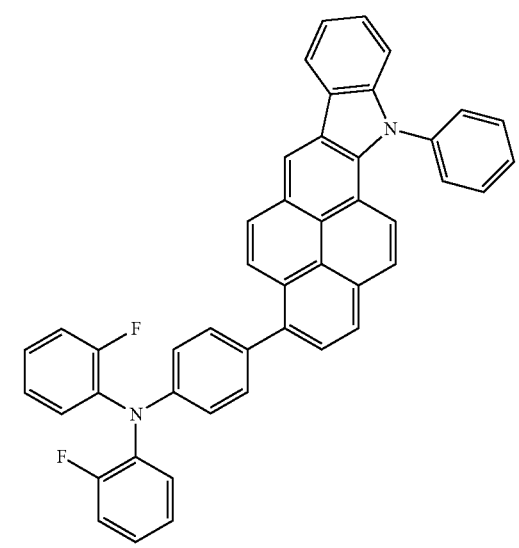
13
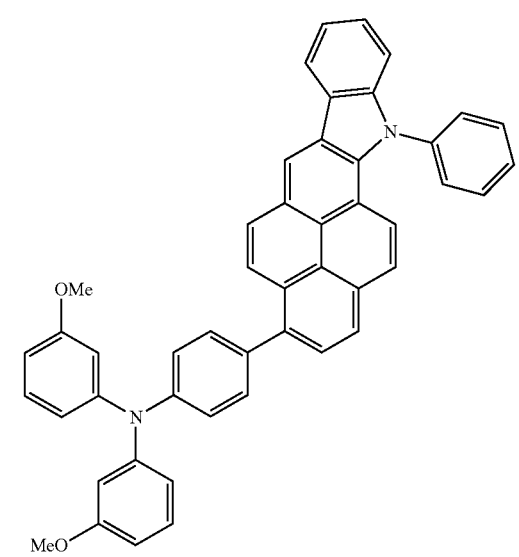
14
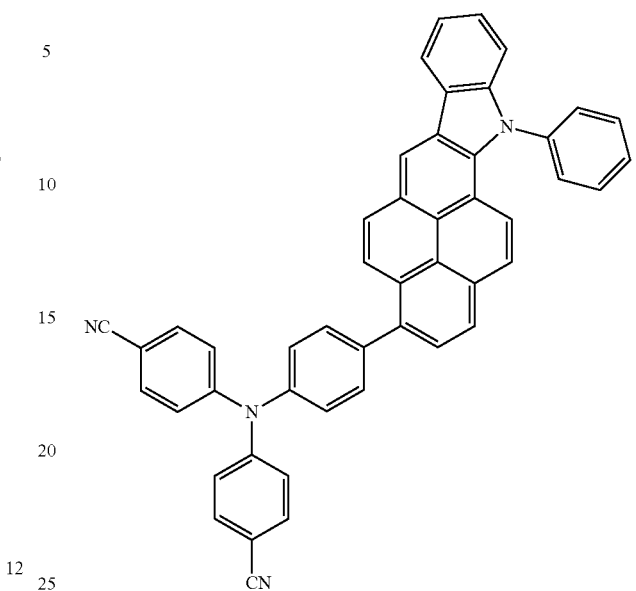
15
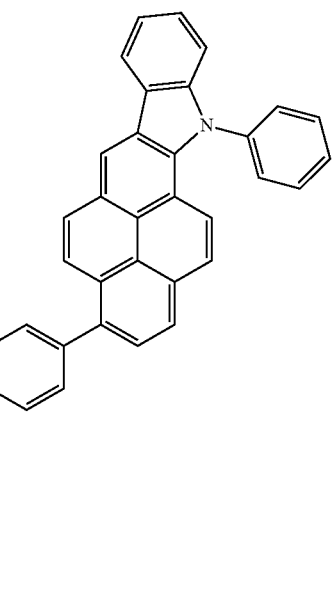

16
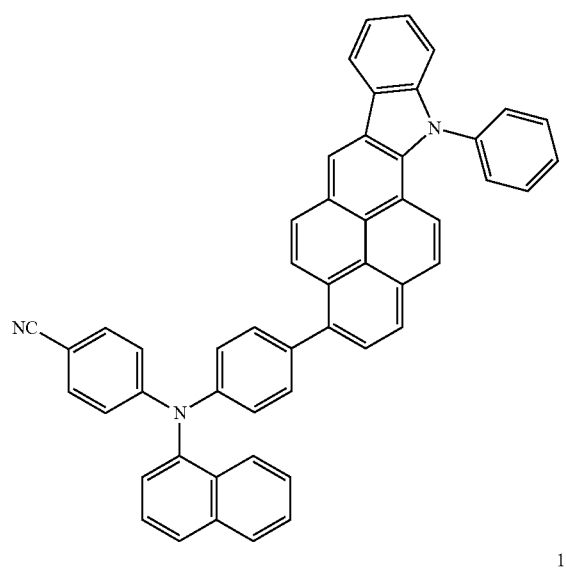
17
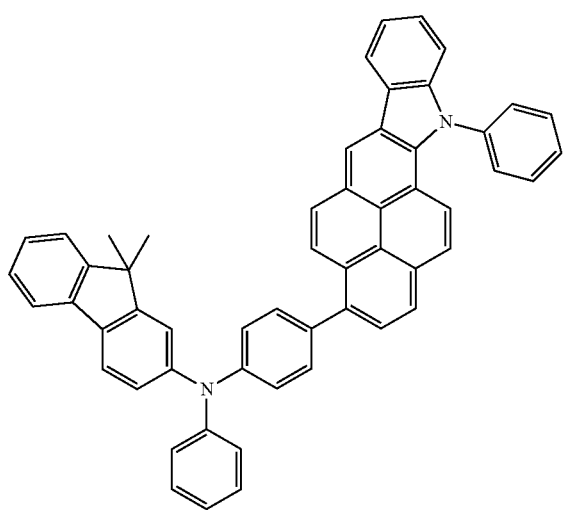
18
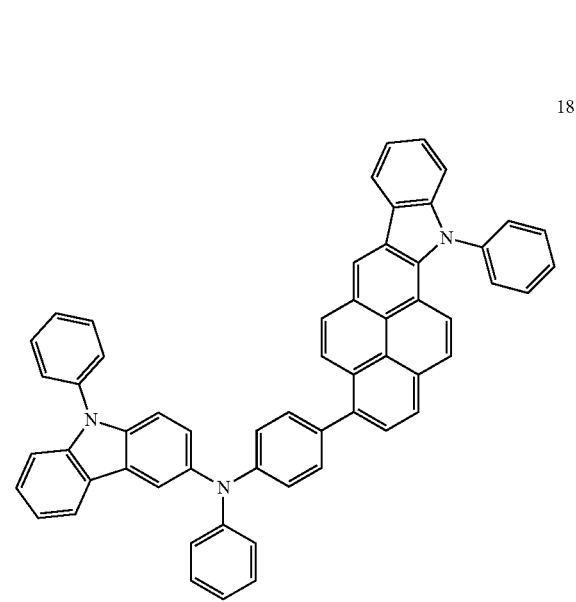
19
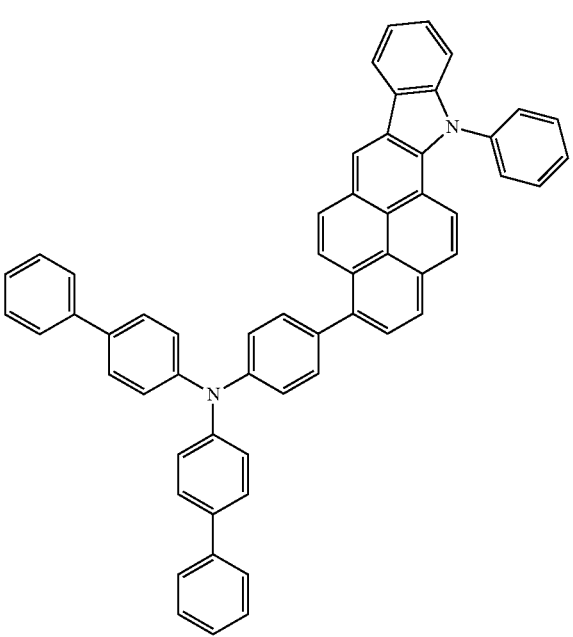
20

21
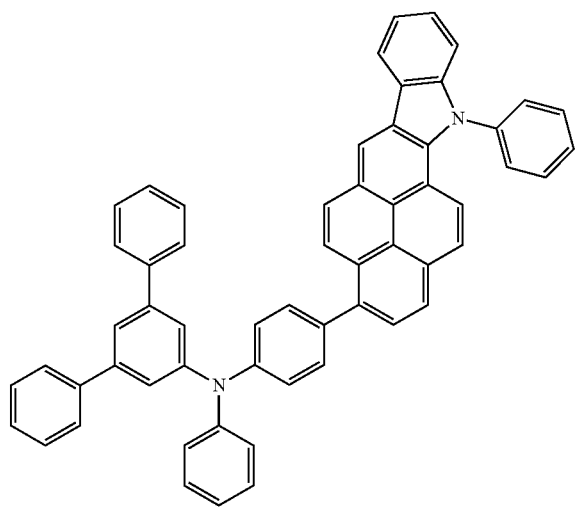
22
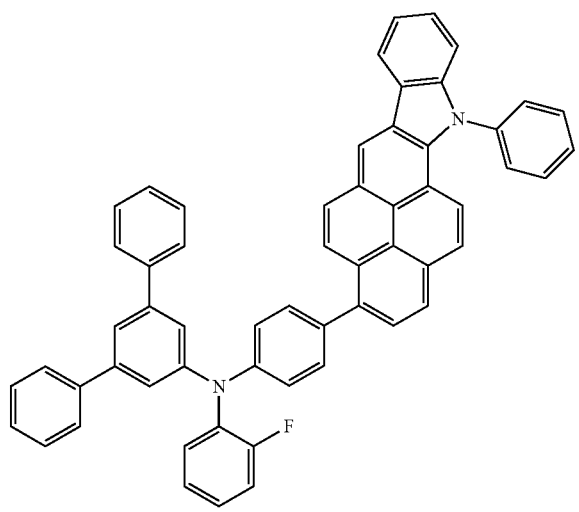
23
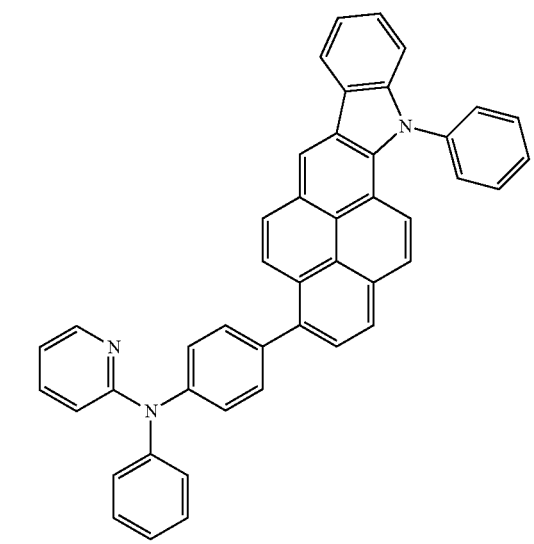
24
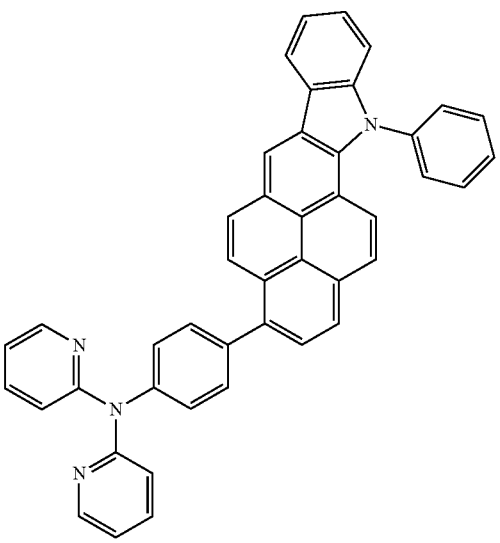
25
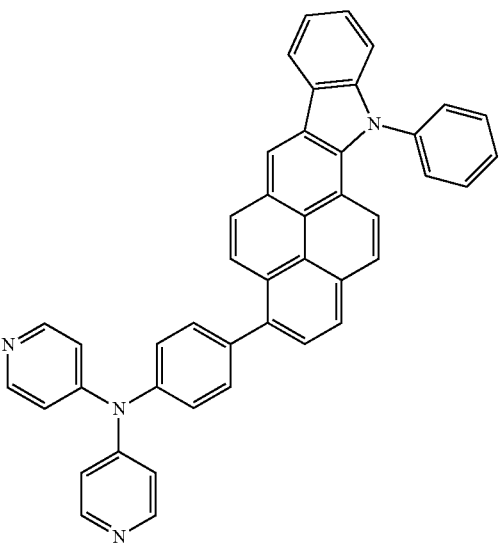
26
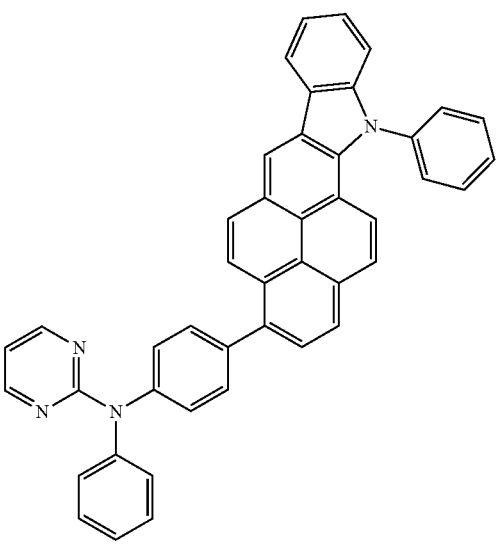

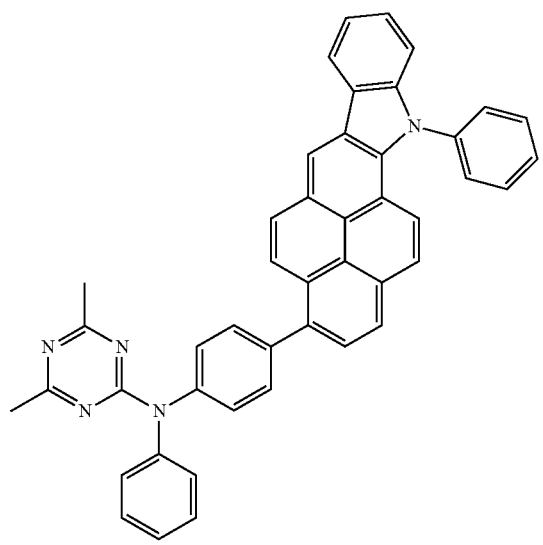
27
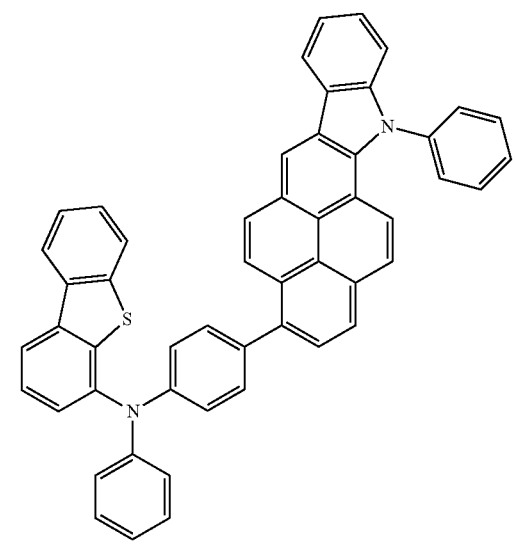
28
29
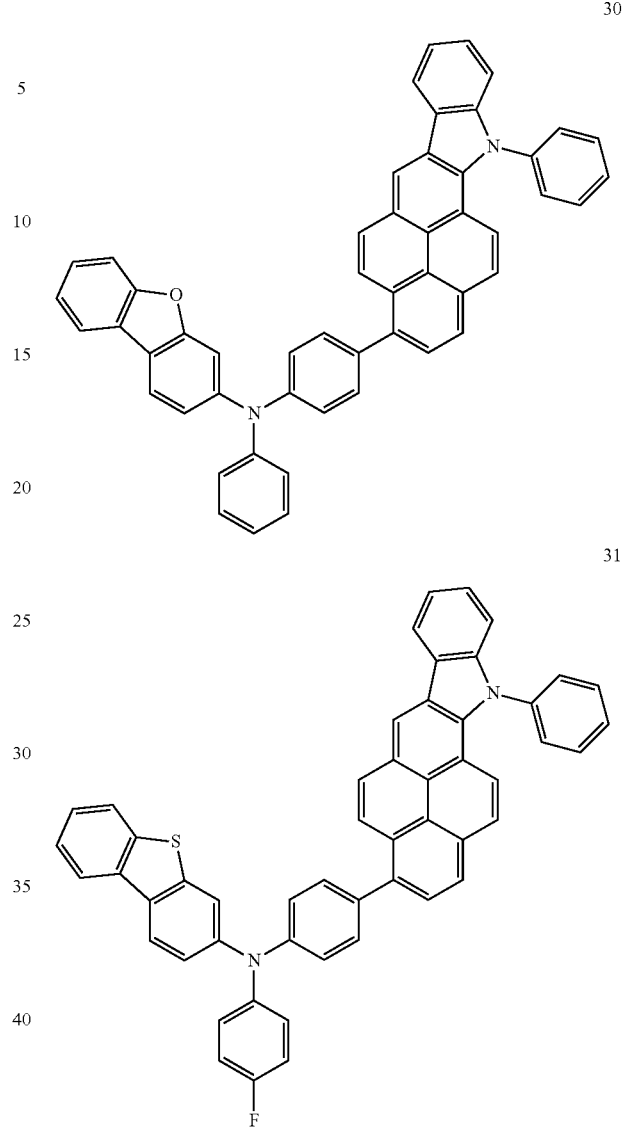
30
31
32

33
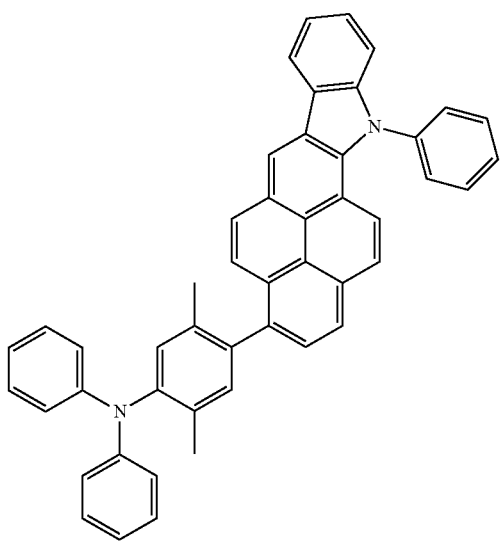
34
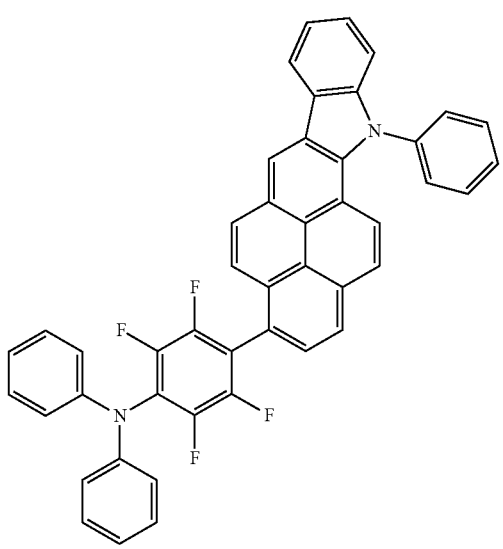
35
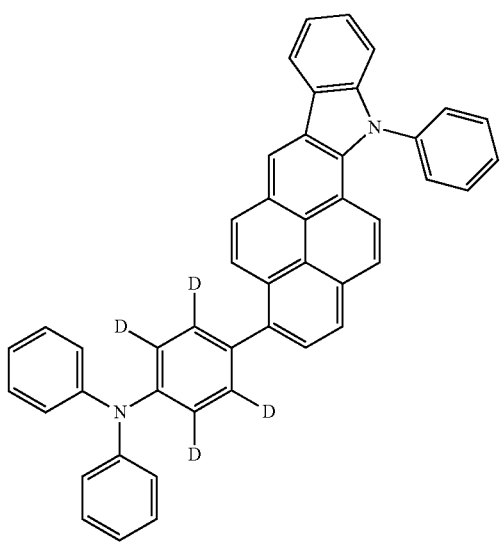
36
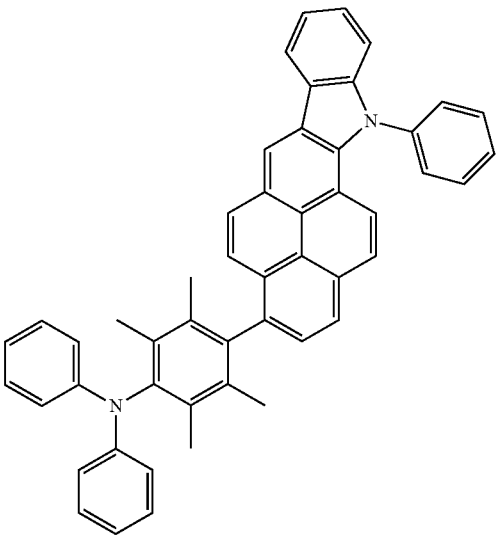
37
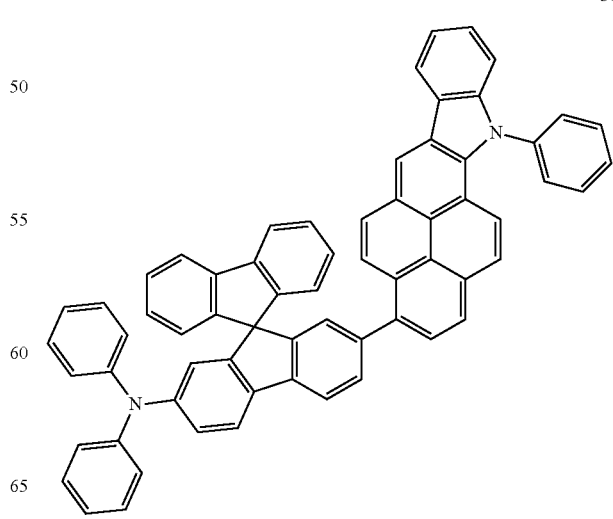
38

39
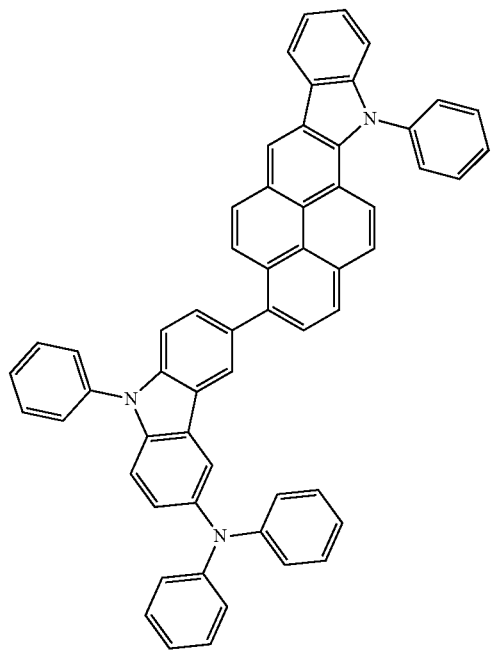
41
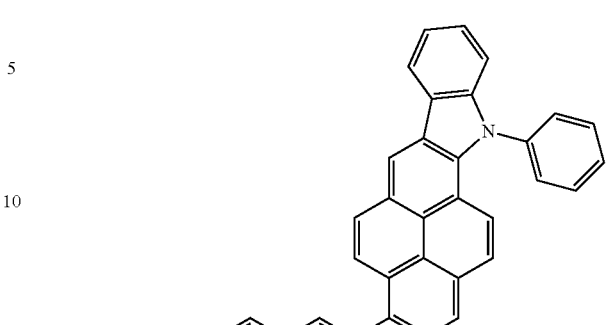
42
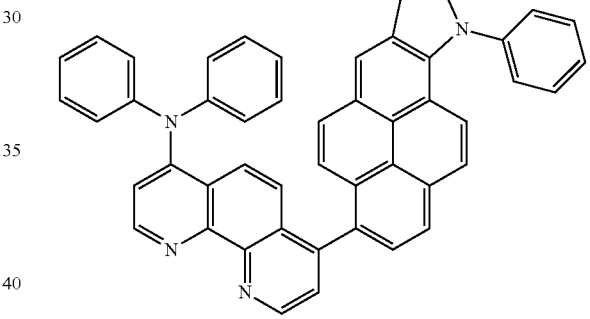
40
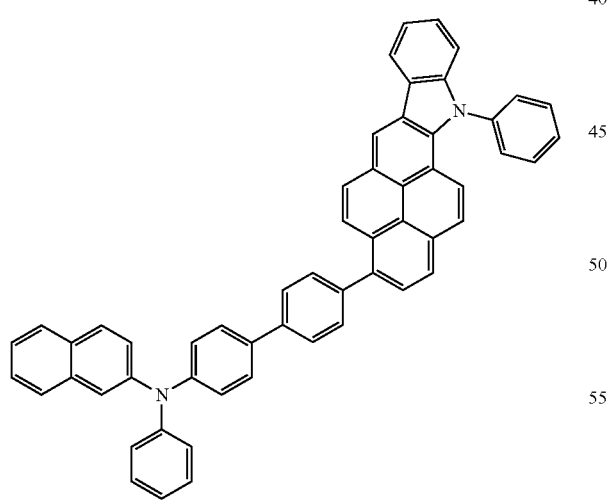
43
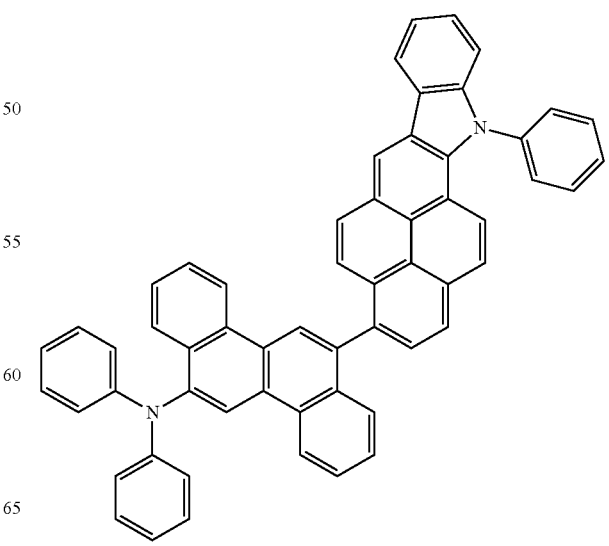

44
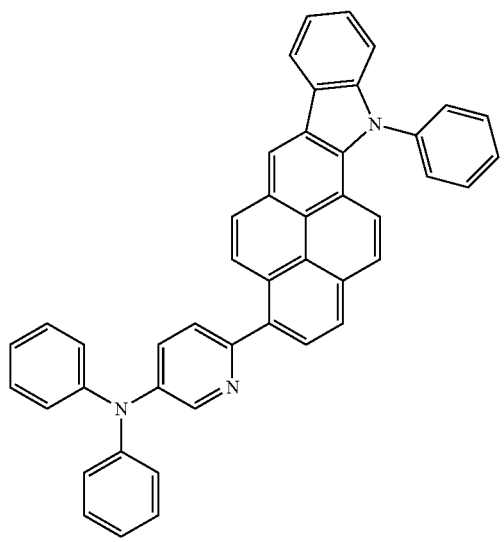
45
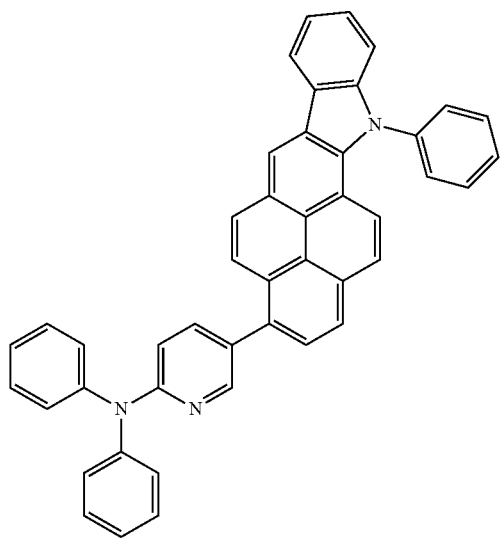
46
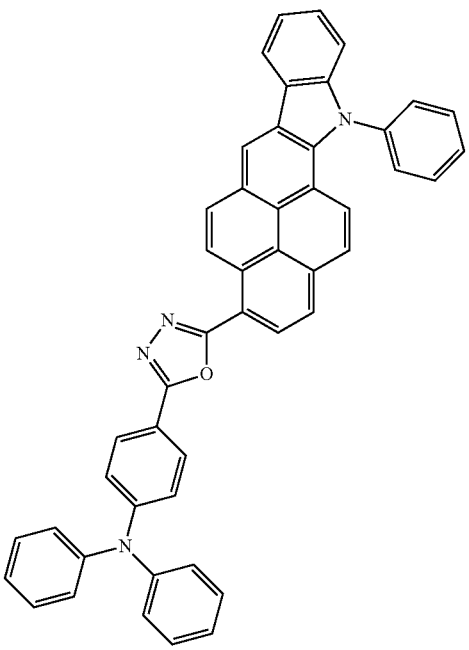
47
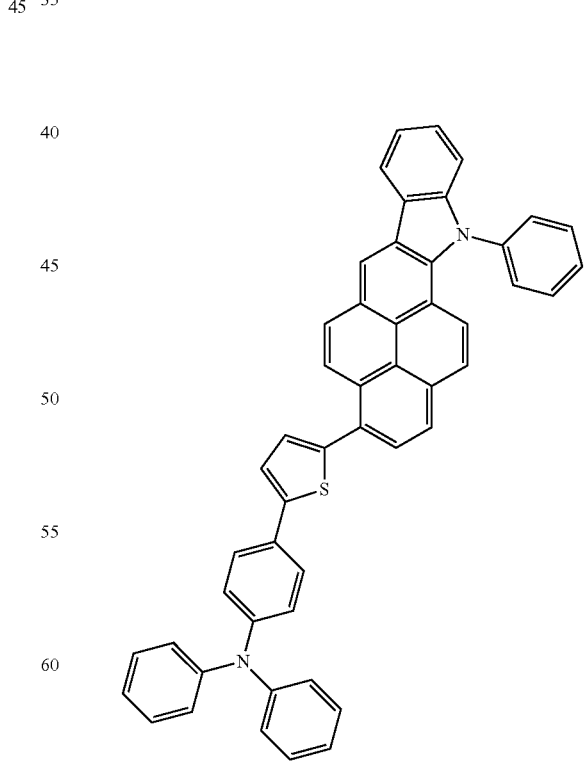

-continued
48
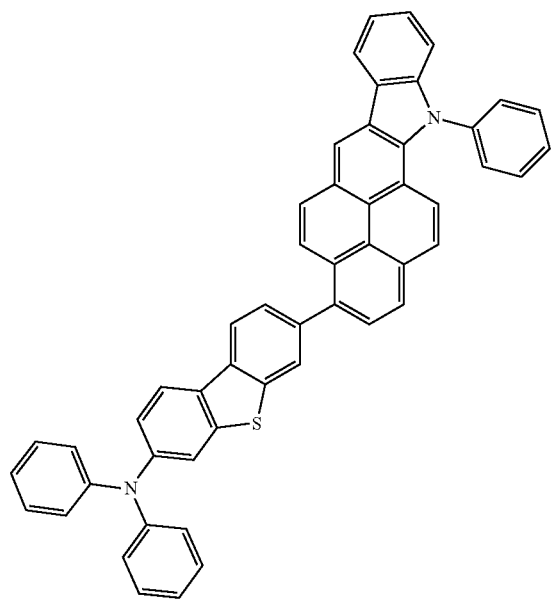
49
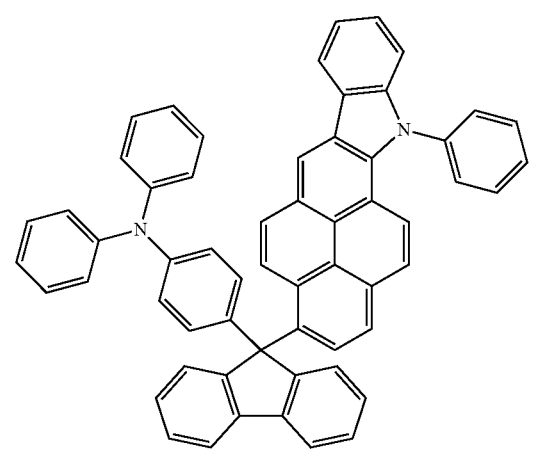
50
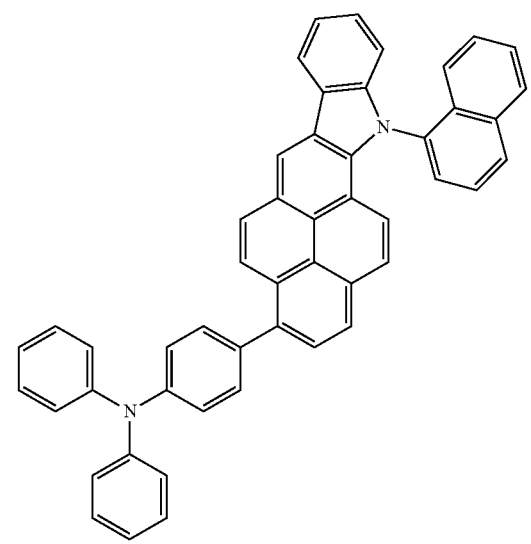
-continued
51
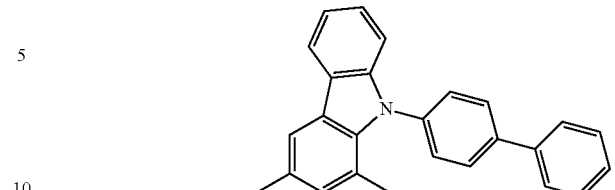
52
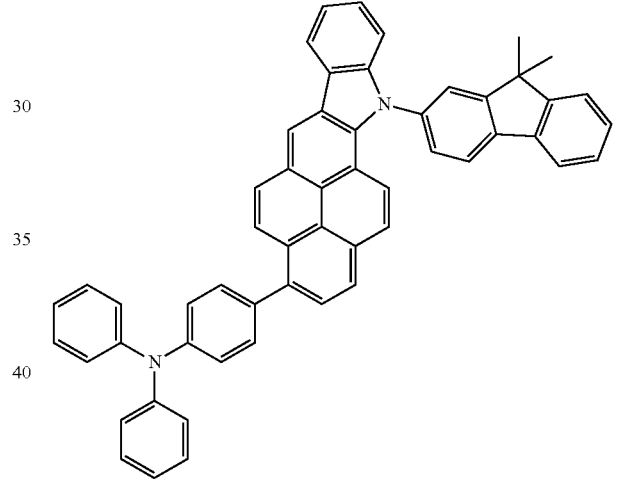
53

54
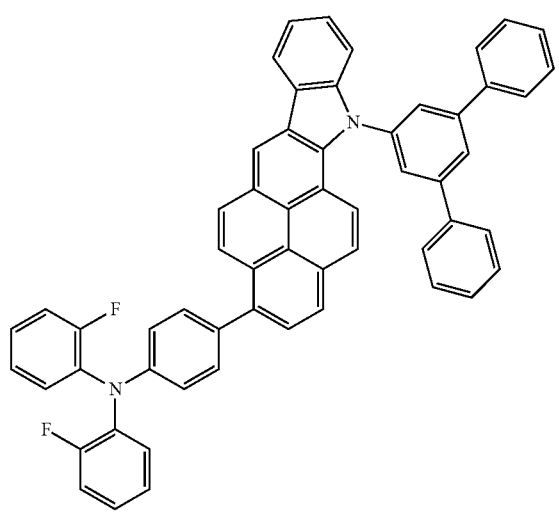
55
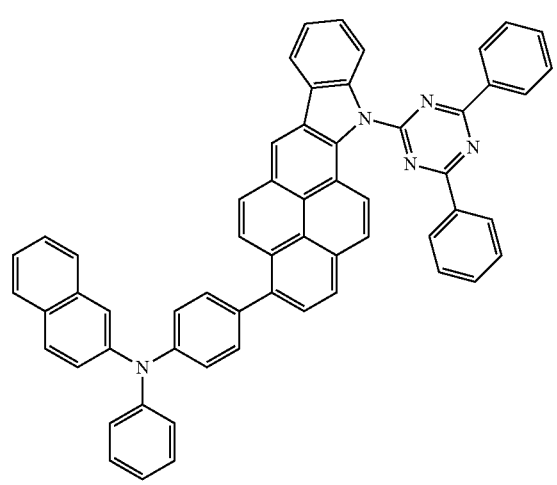
56
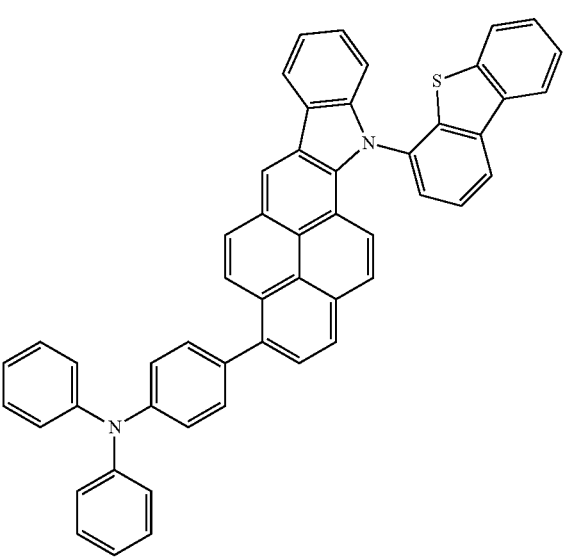
57
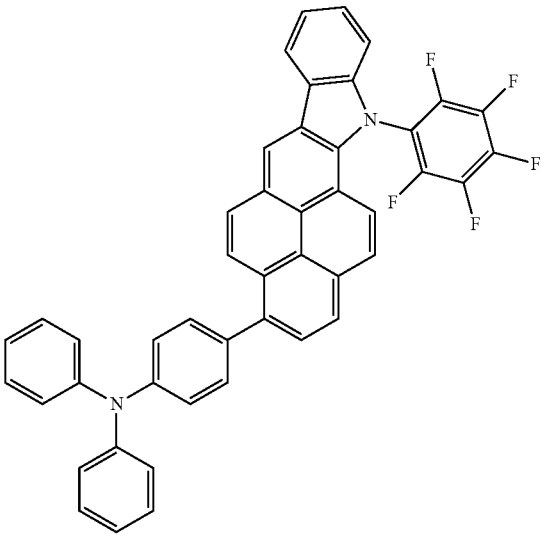
58
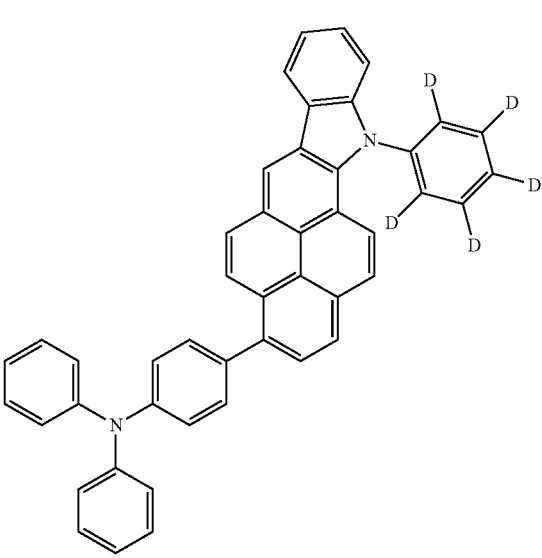
59
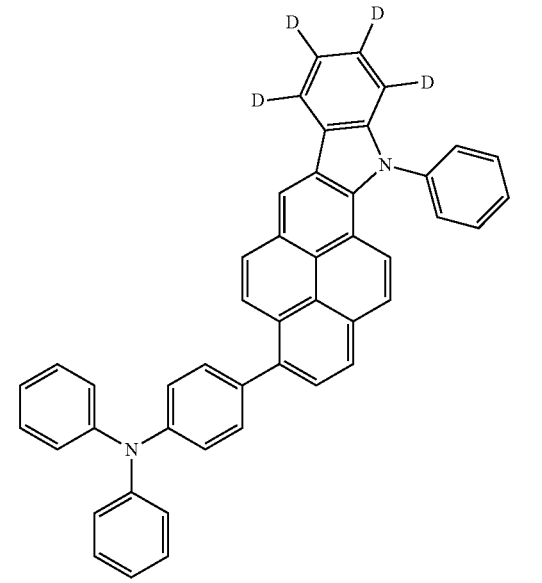

60
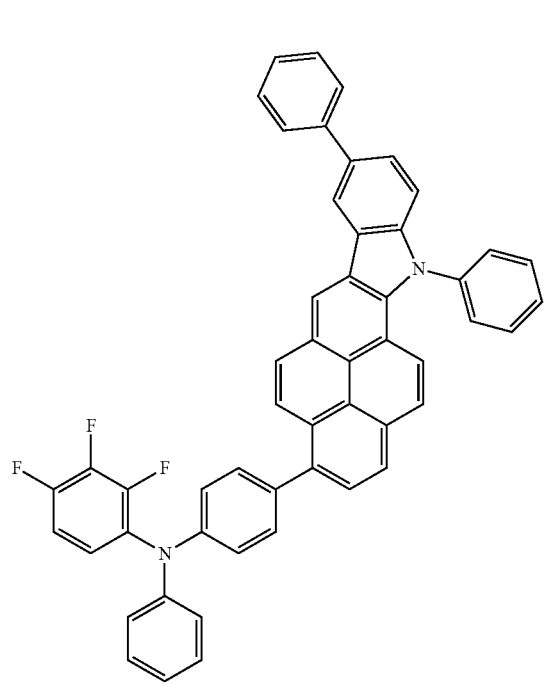
61
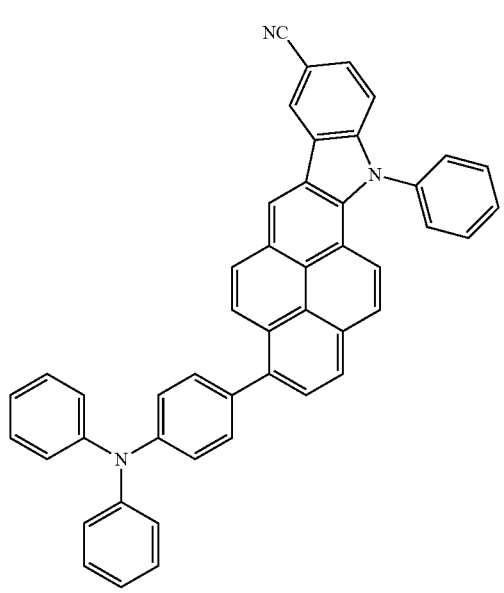
62
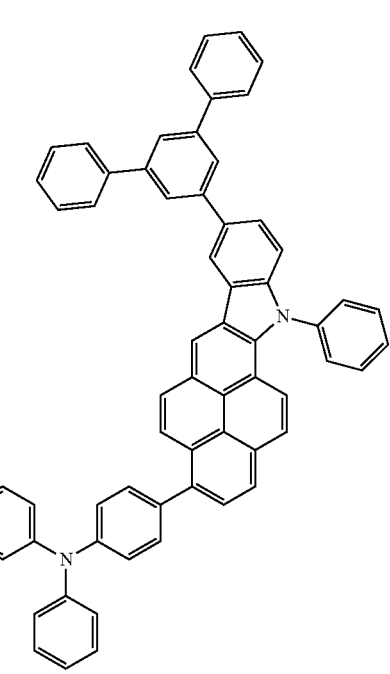
63
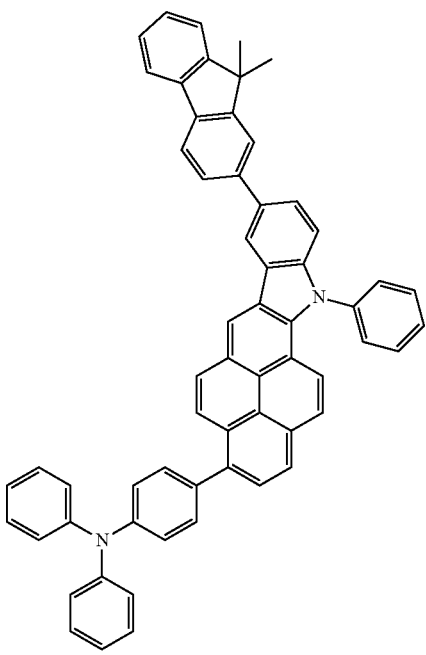

64
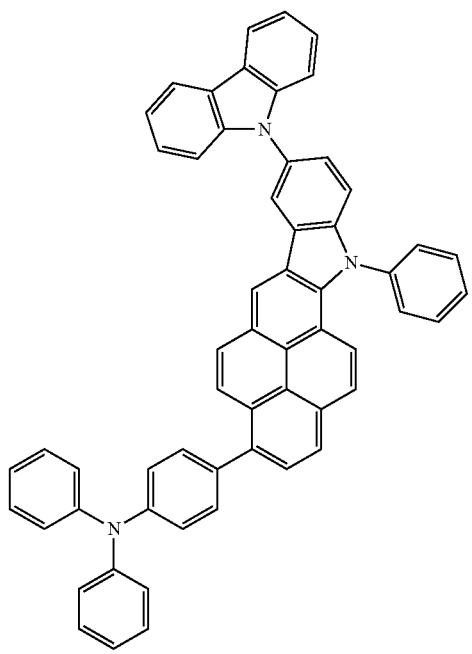
66
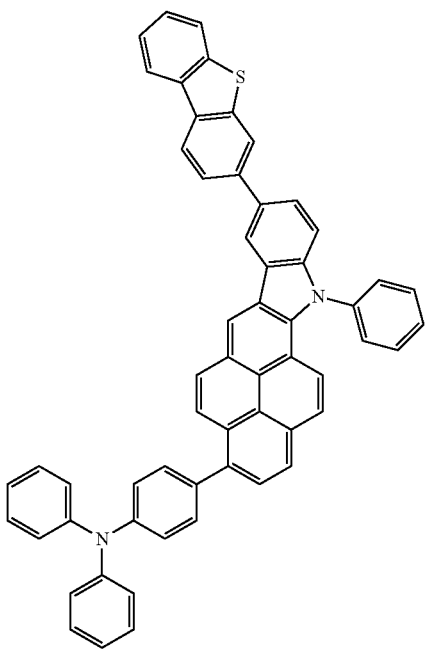
65
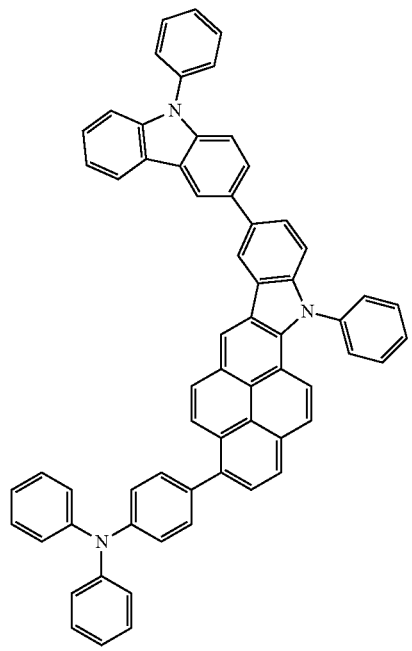
67
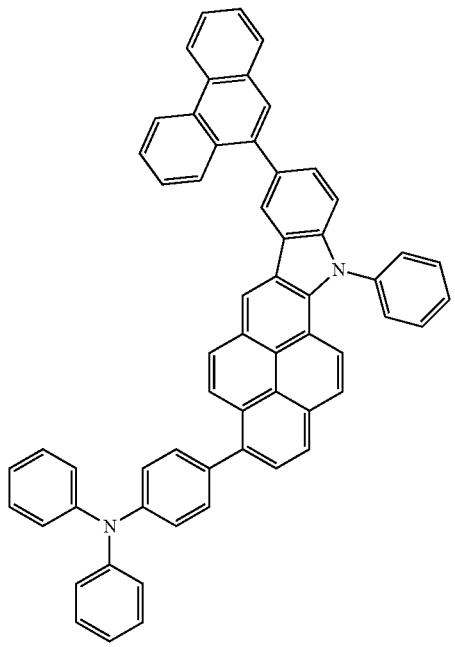

-continued
68
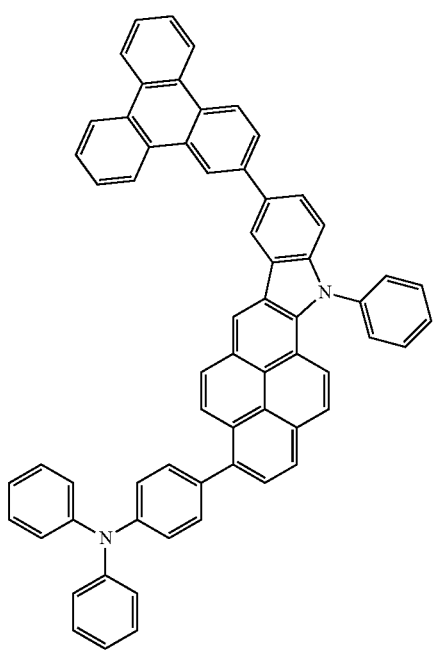
69
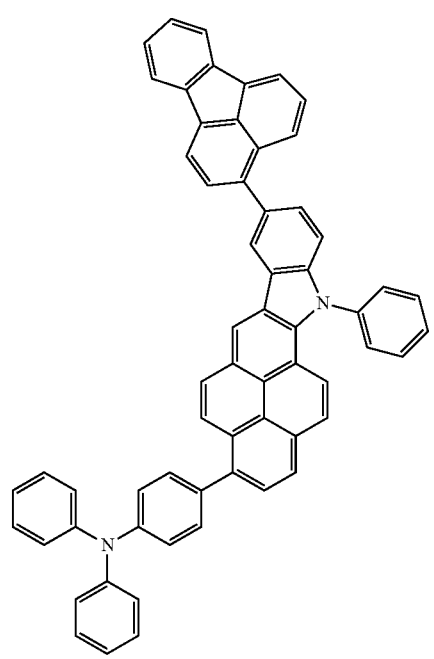
-continued
70
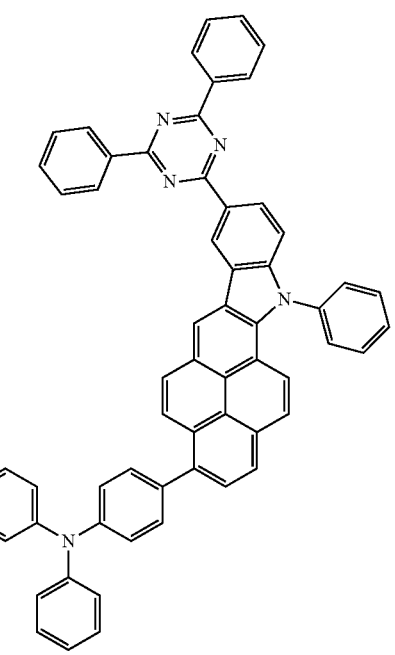
71
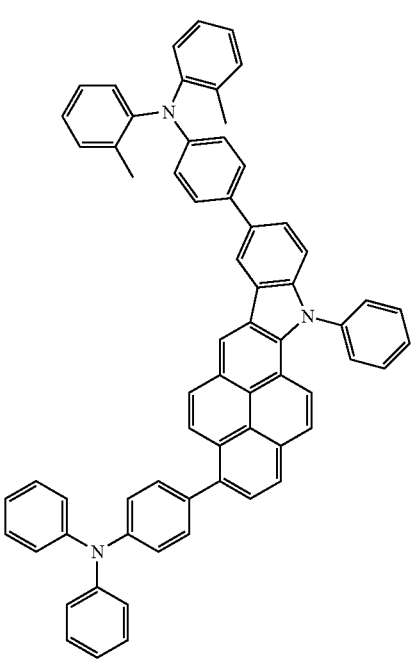

73
-continued
72
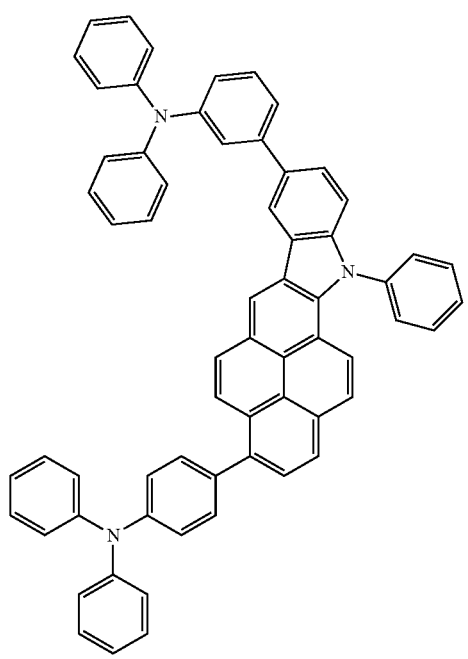
73
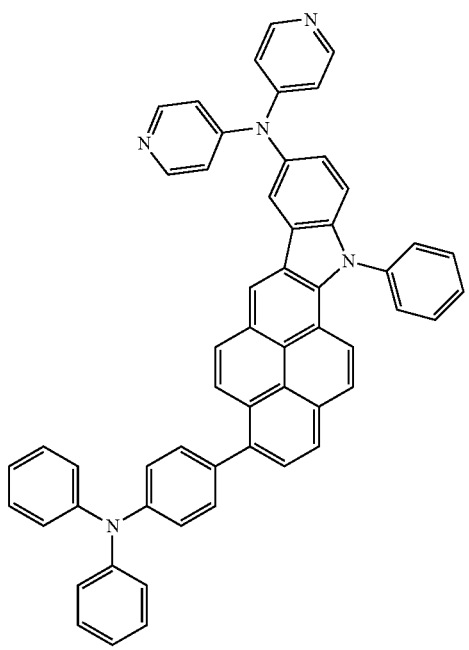
74
-continued
74
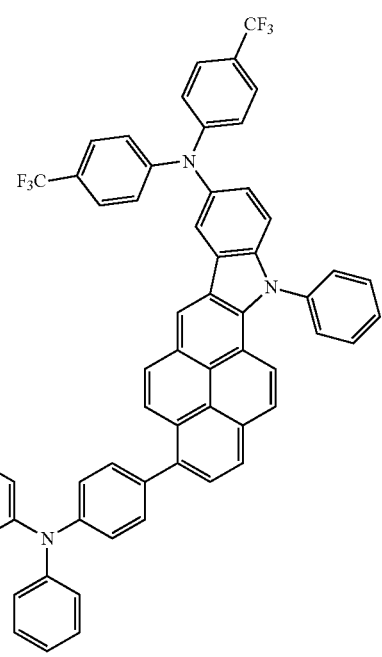
75
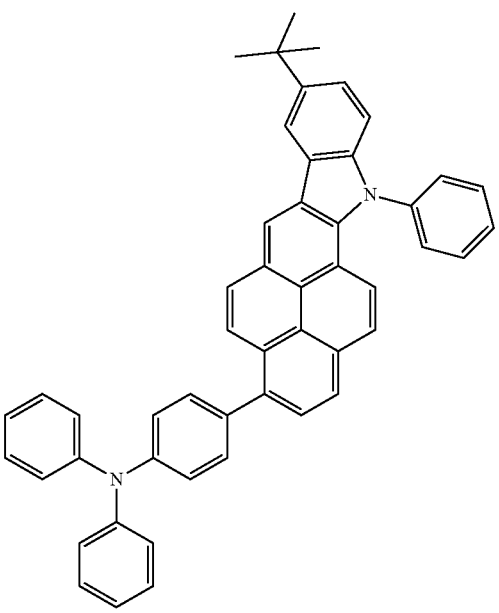

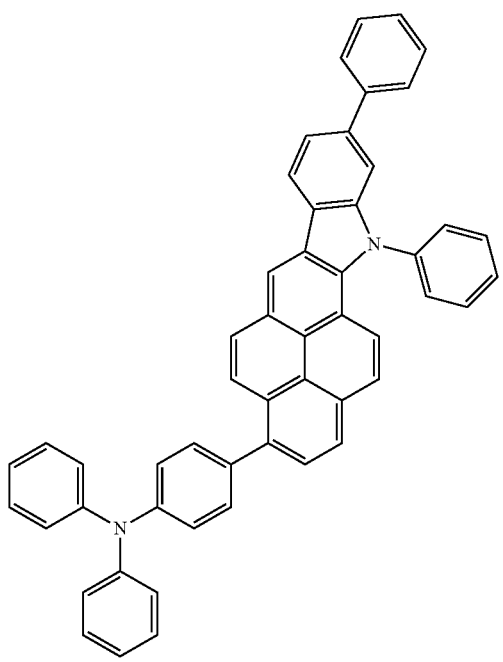
76
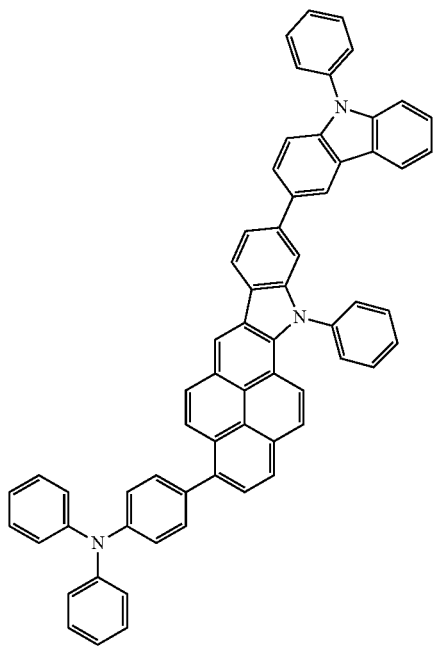
78
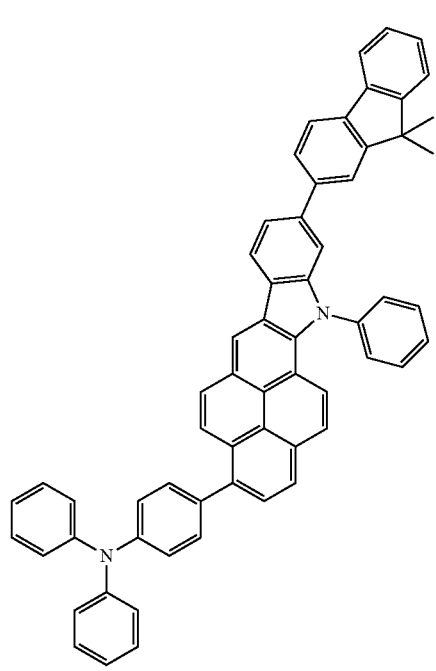
77
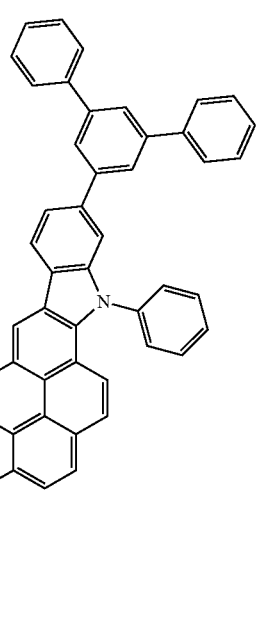
79

80
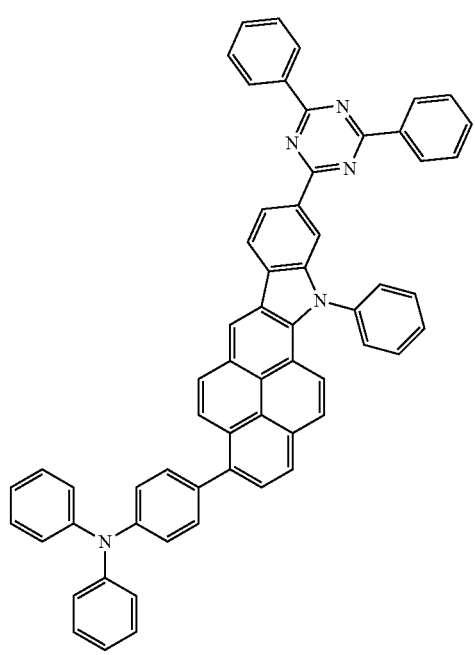
81
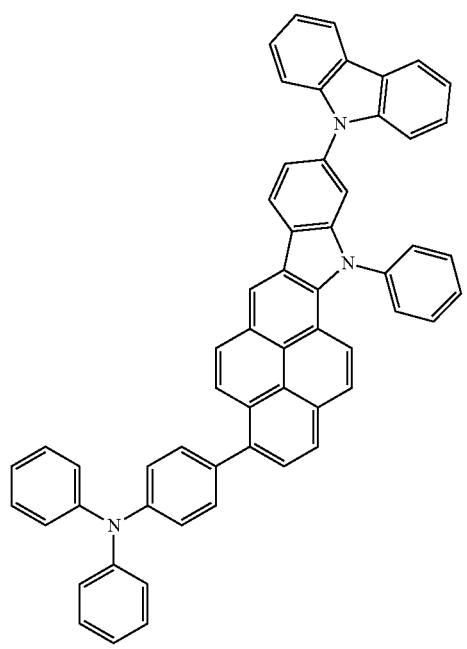
82
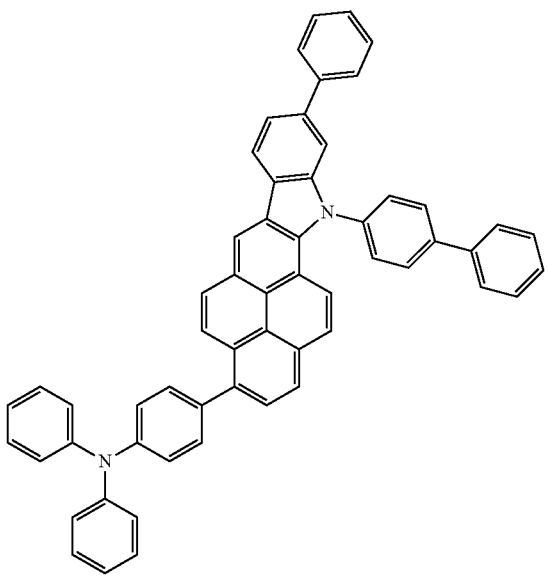
83
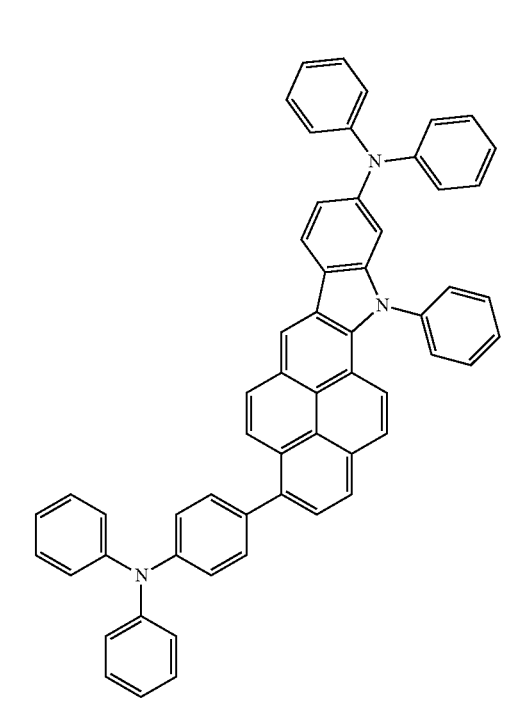

84
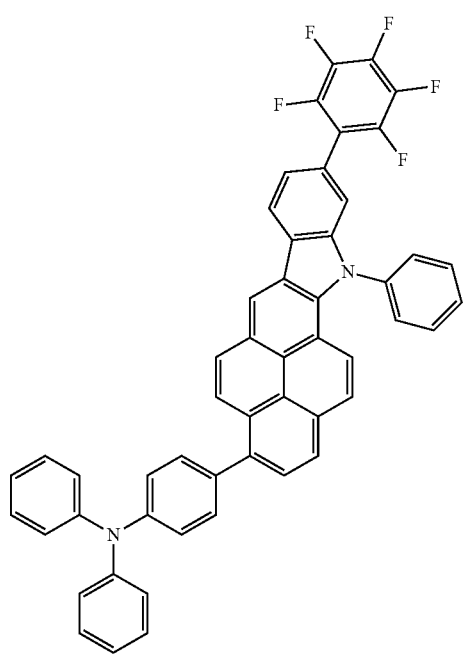
85
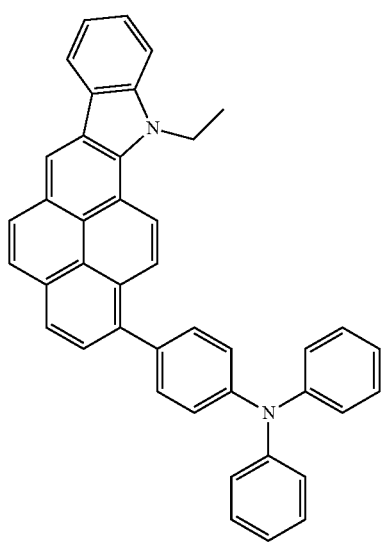
86
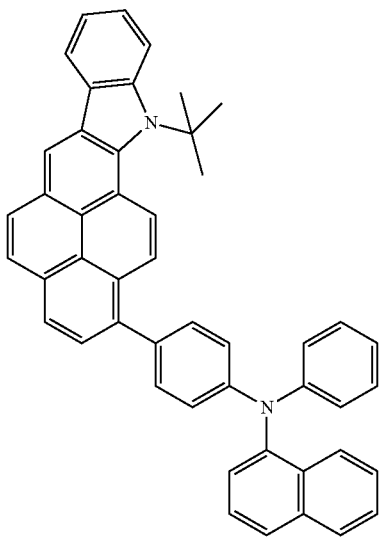
87
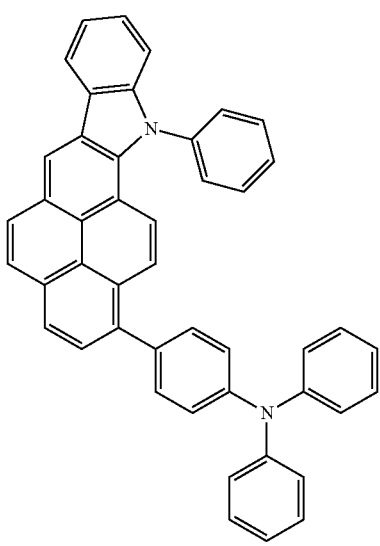
88
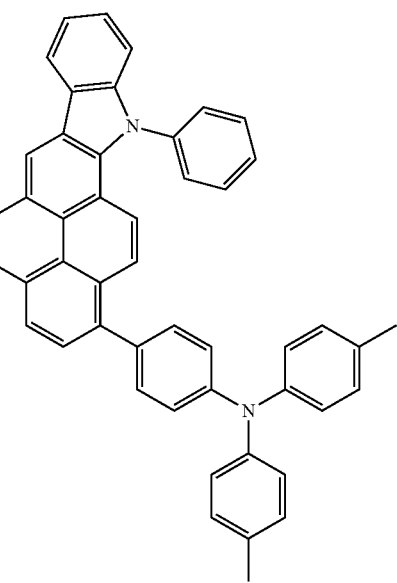

81 -continued
89
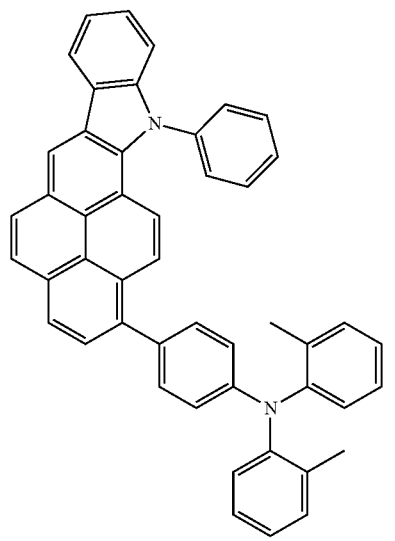
90
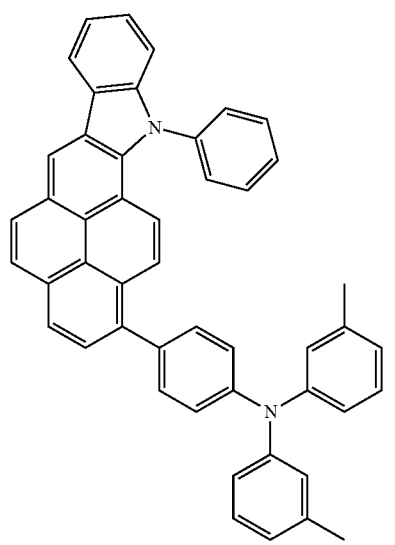
91
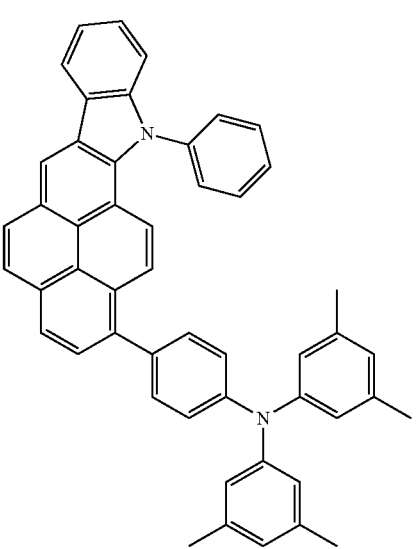
82 -continued
92
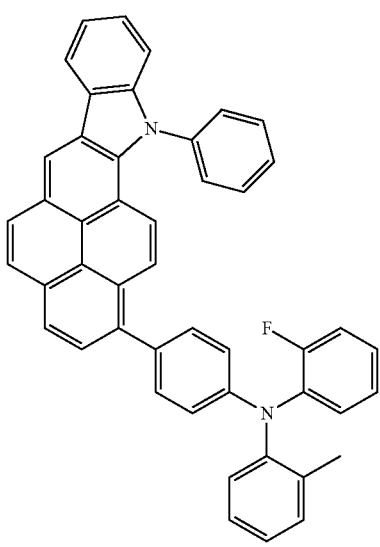
93
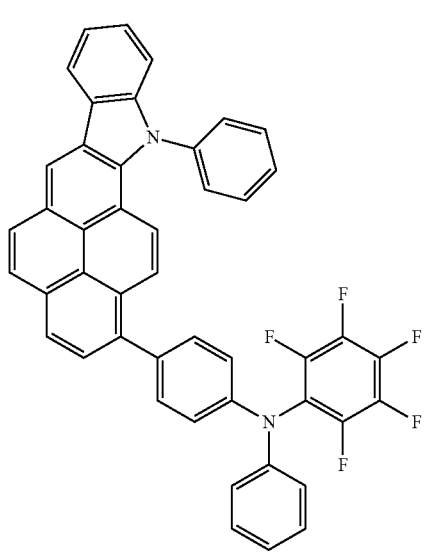
94
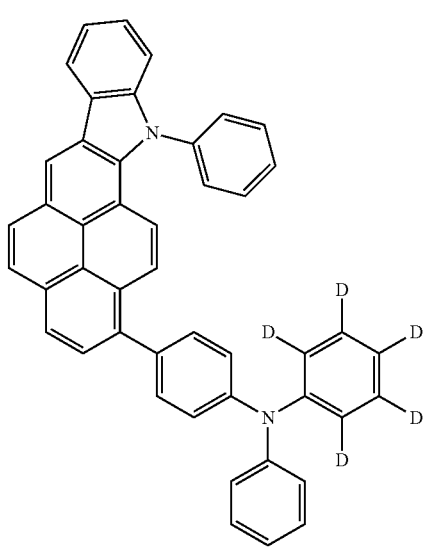

95
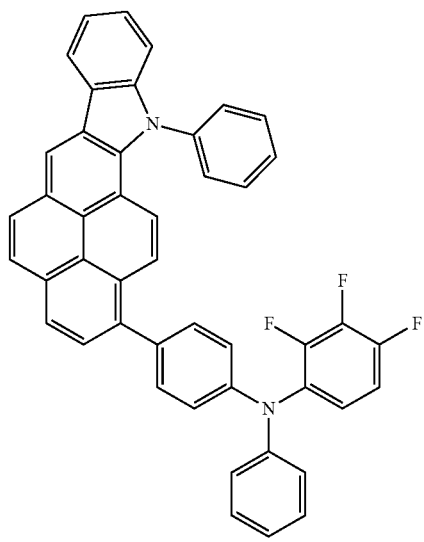
96
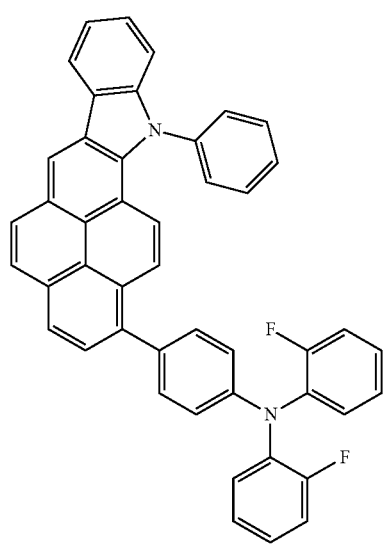
97
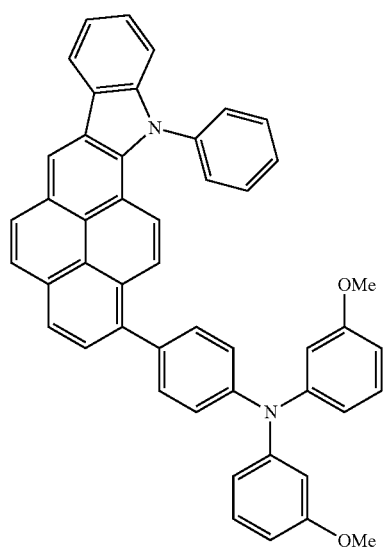
98
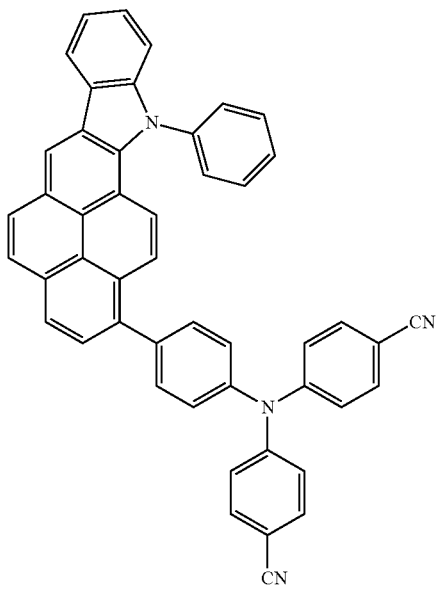
99
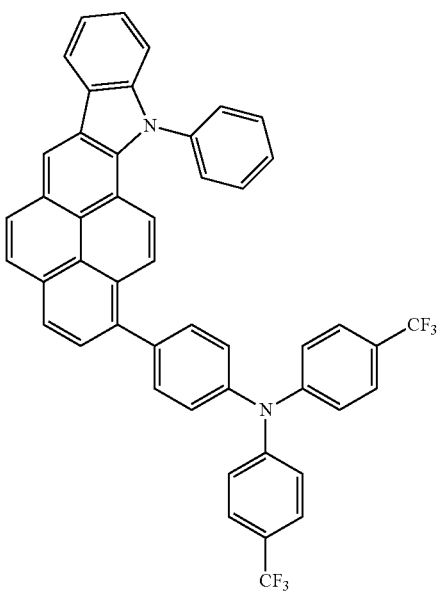

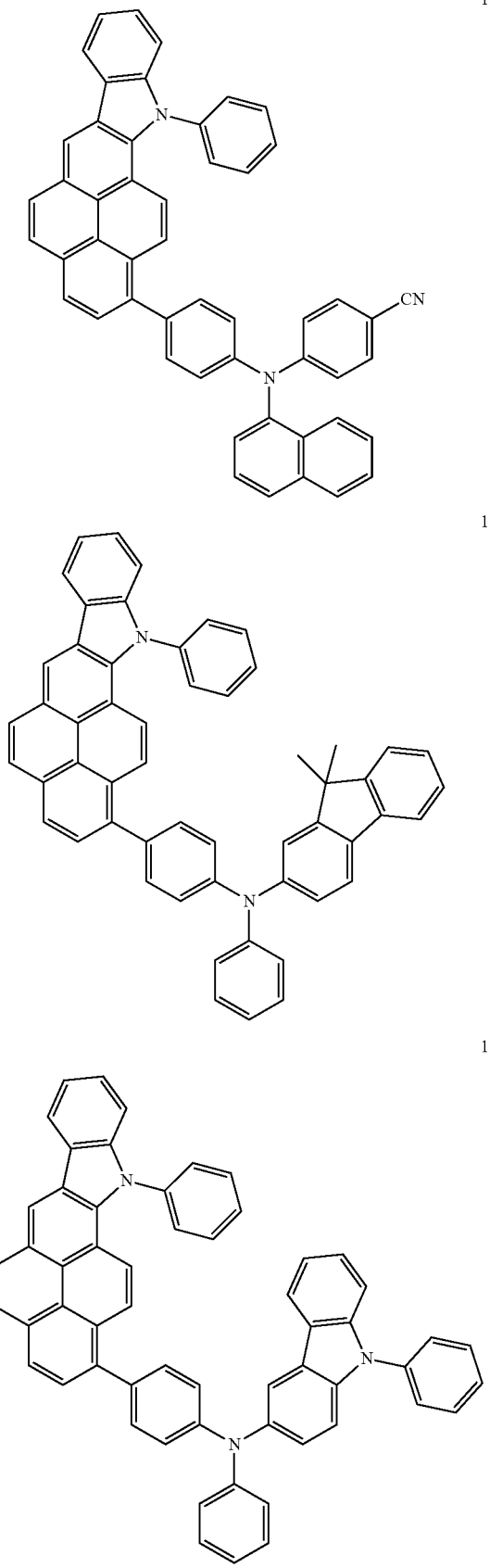
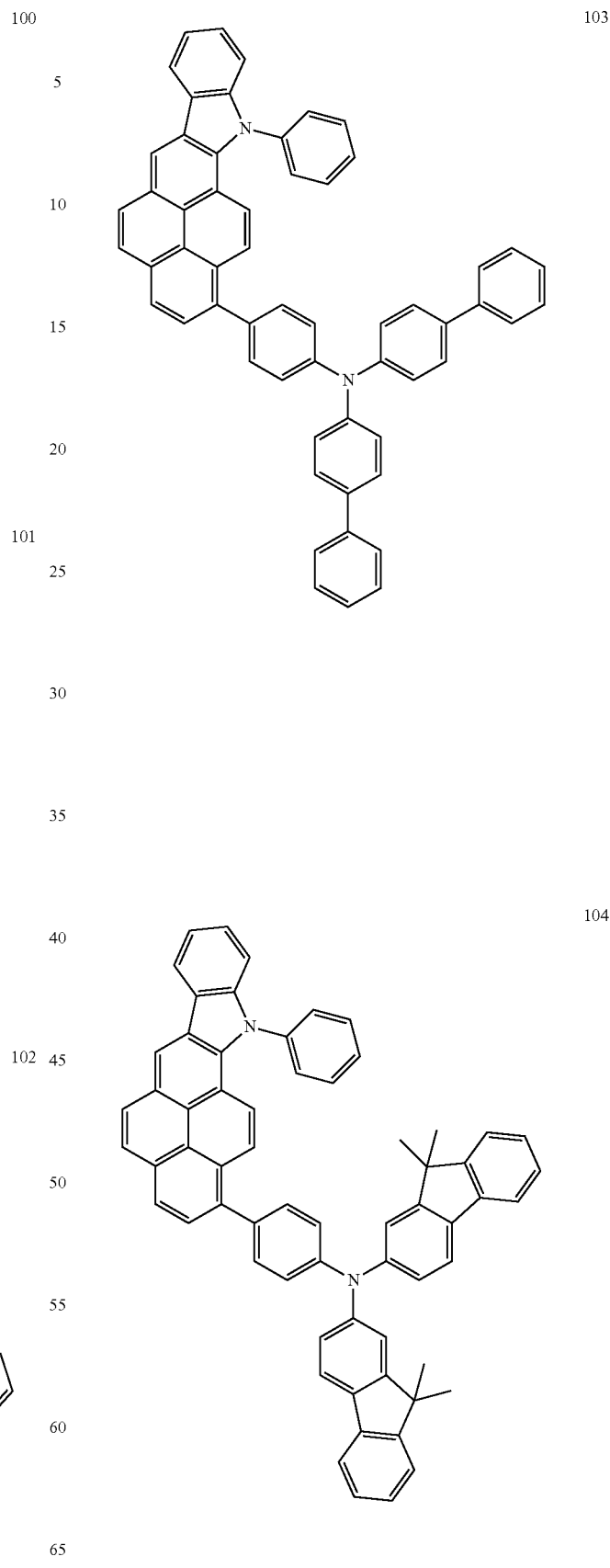

87
-continued
105
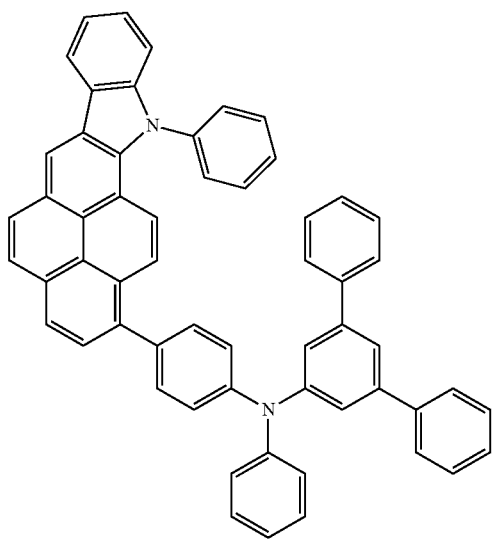
106
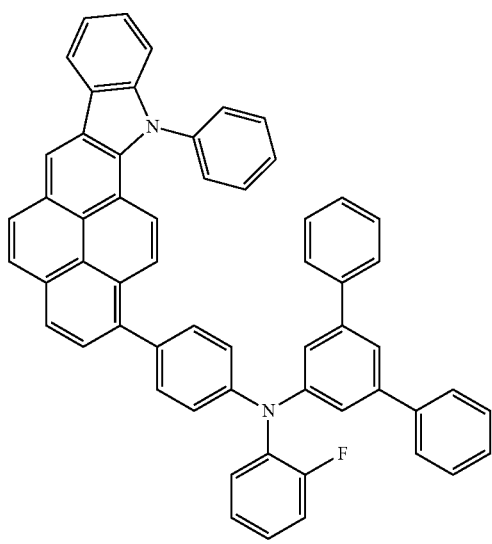
107
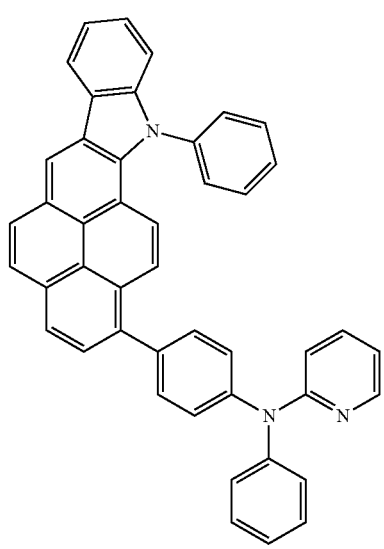
88
-continued
108
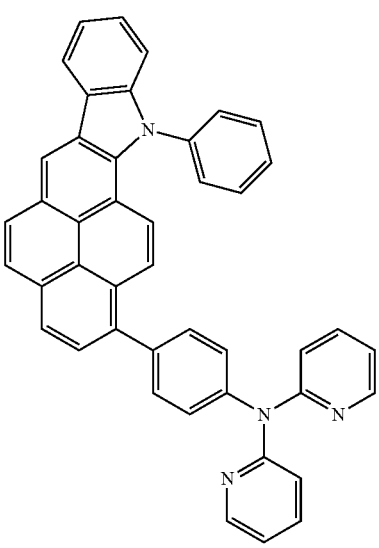
109
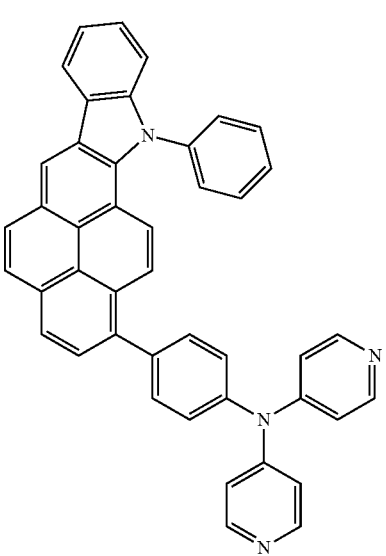
110
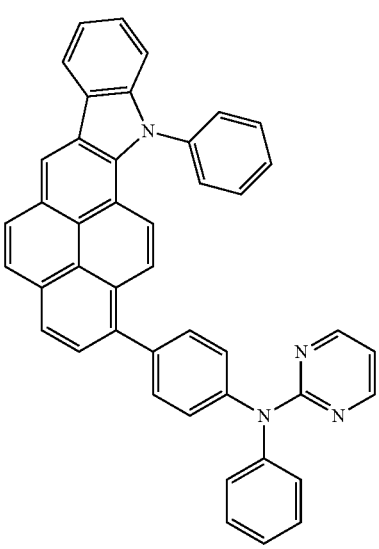

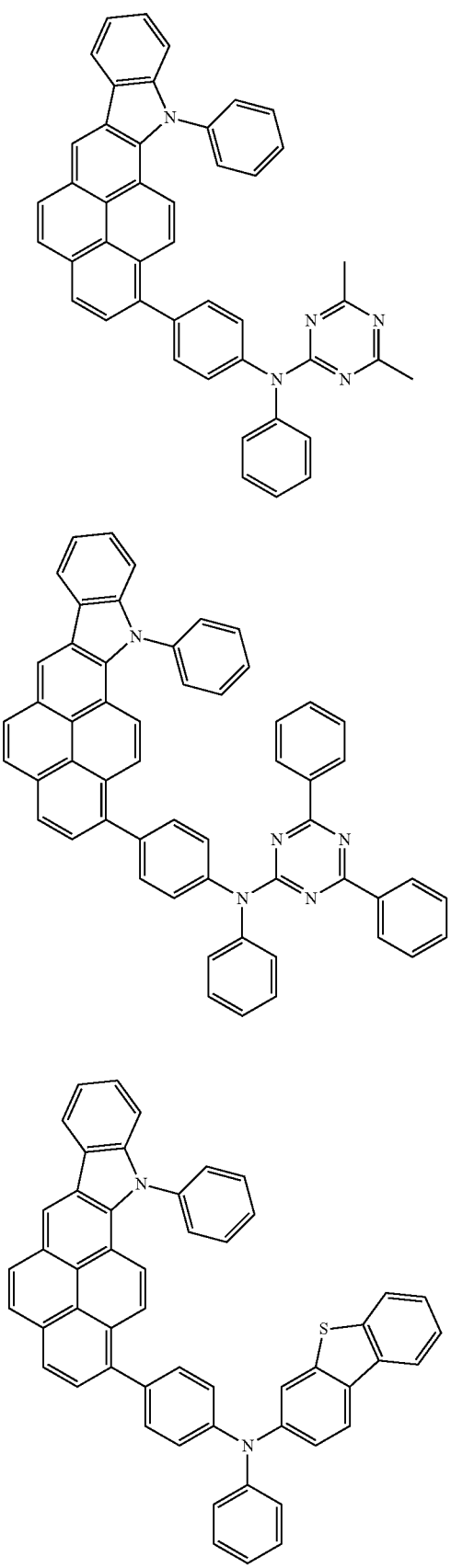
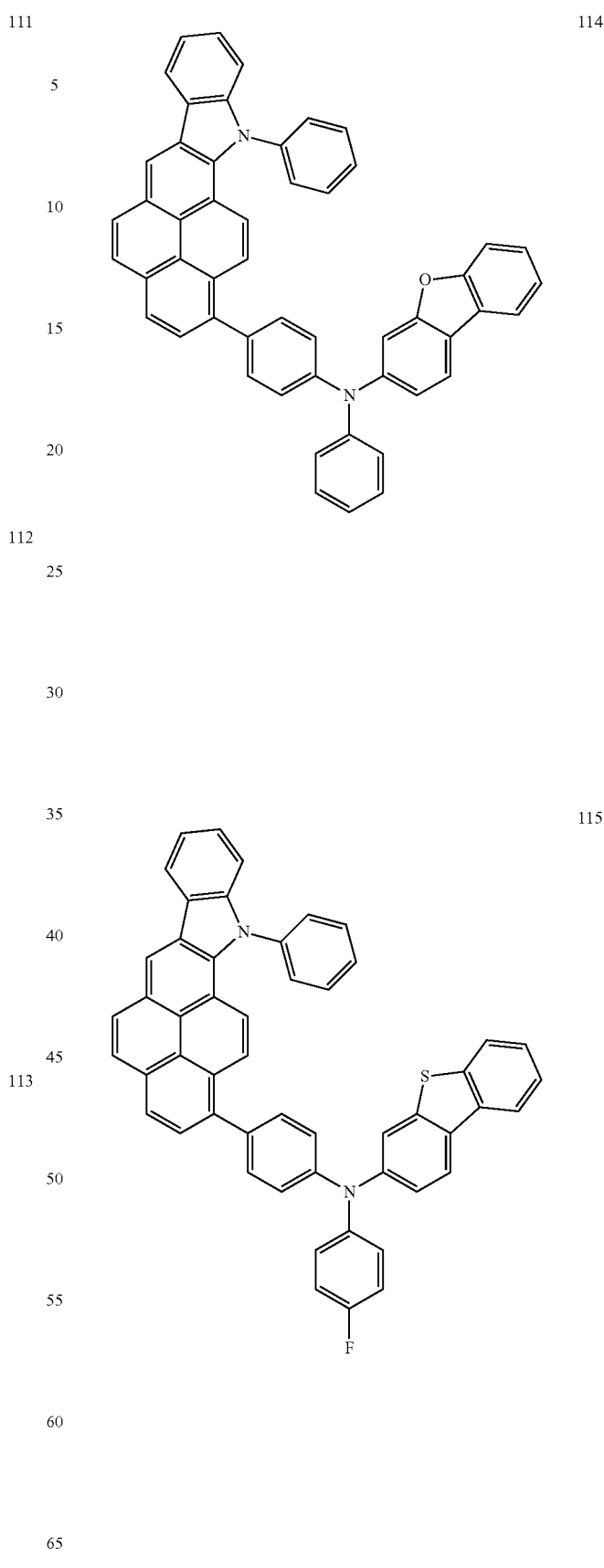

116
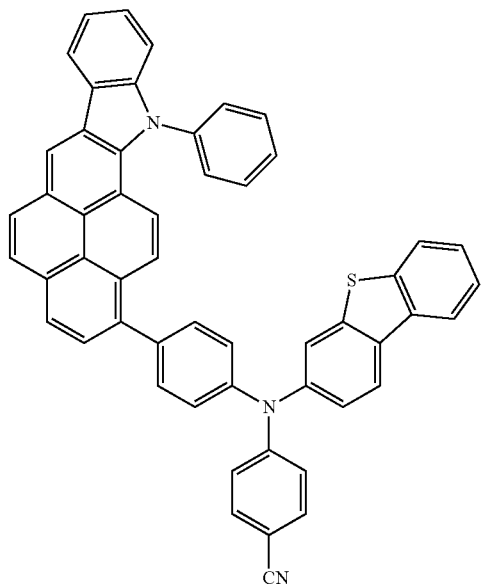
117
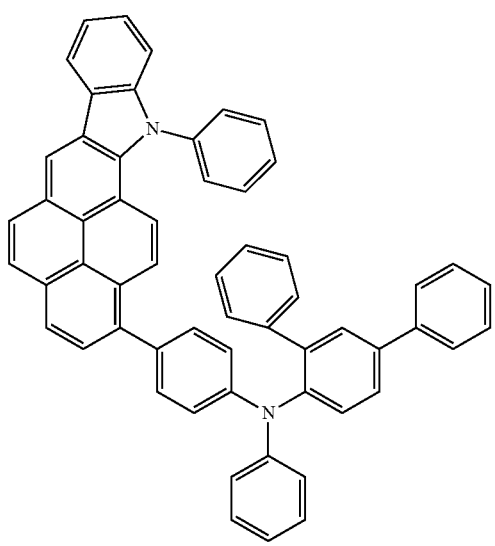
118
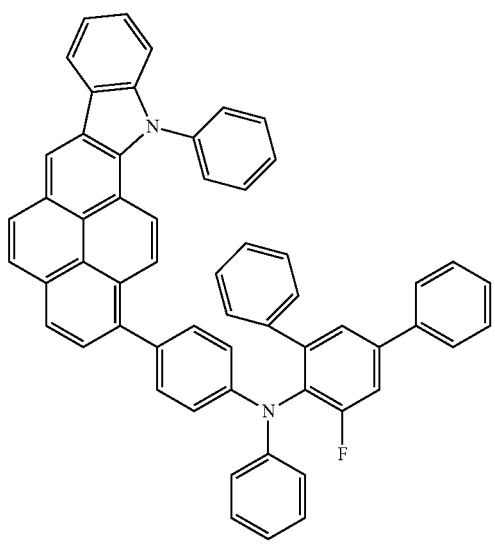
119
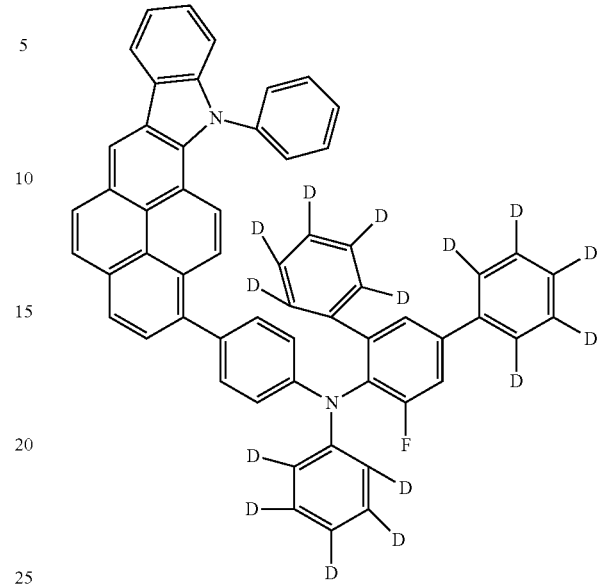
120
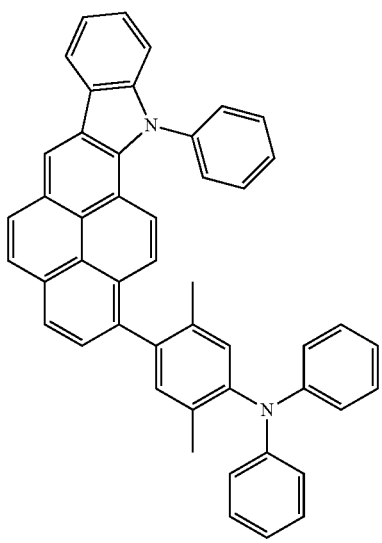

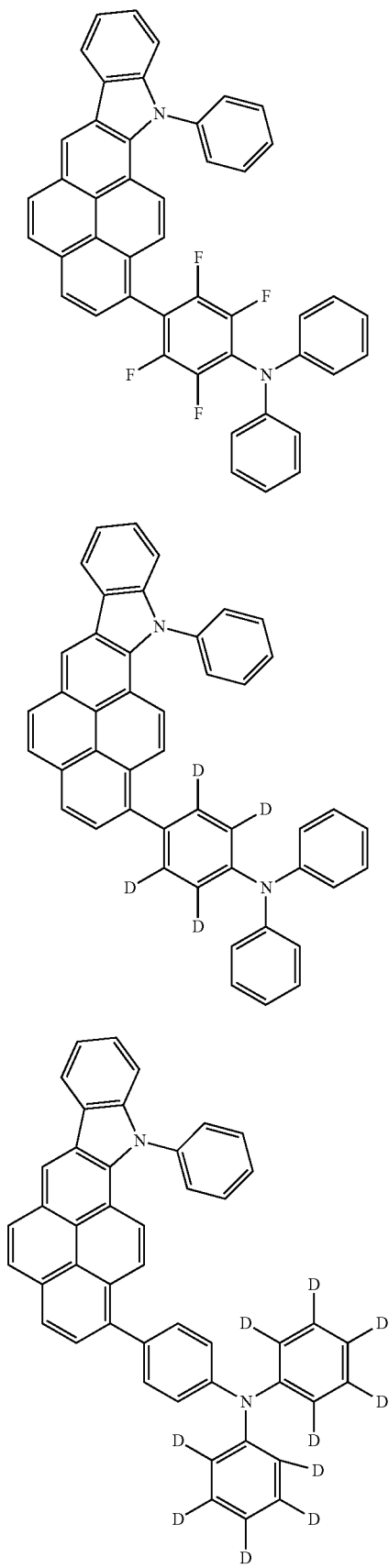
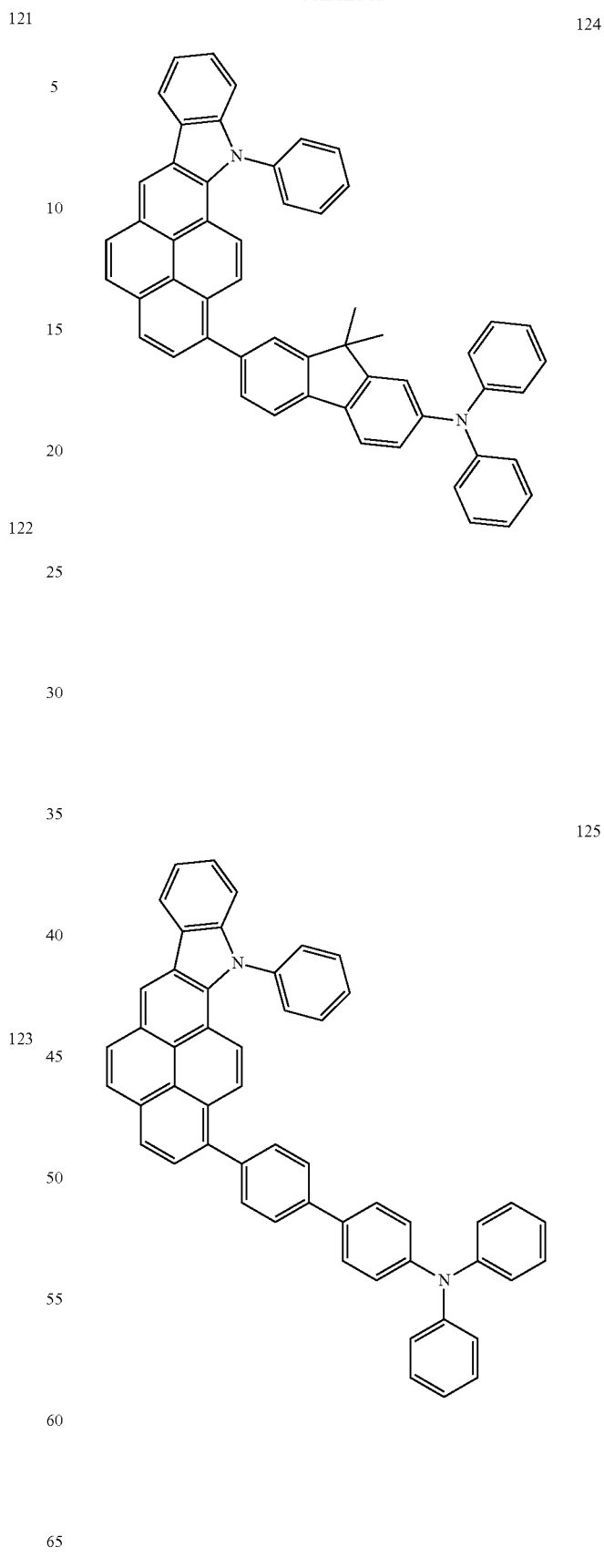

126
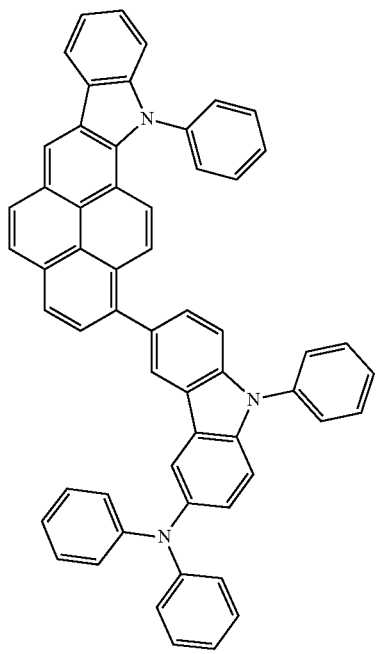
127
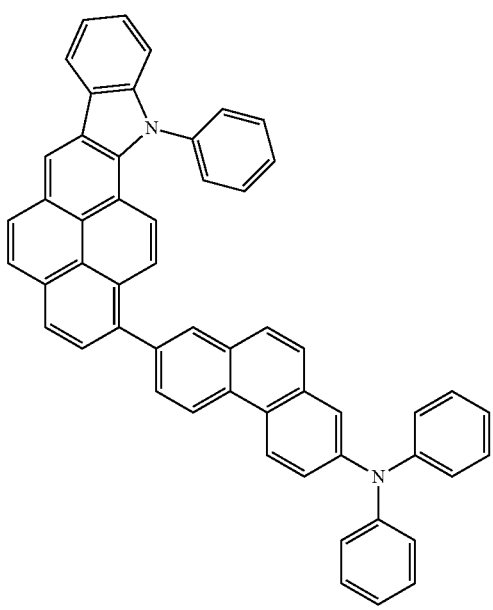
128
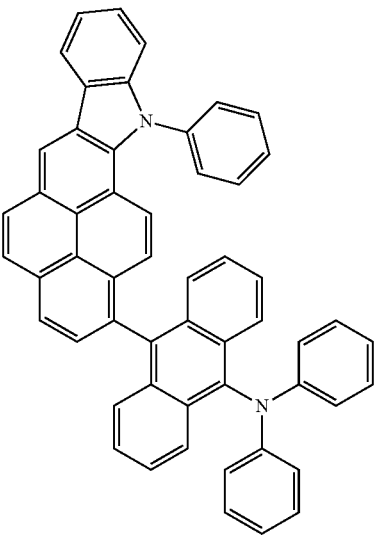
129
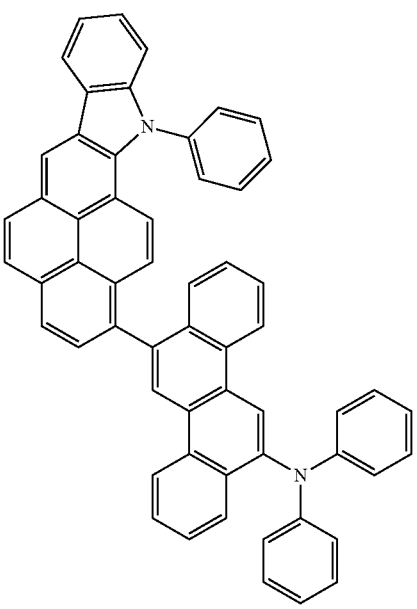

| 97 -continued | 98 -continued |
|---|---|
| 130 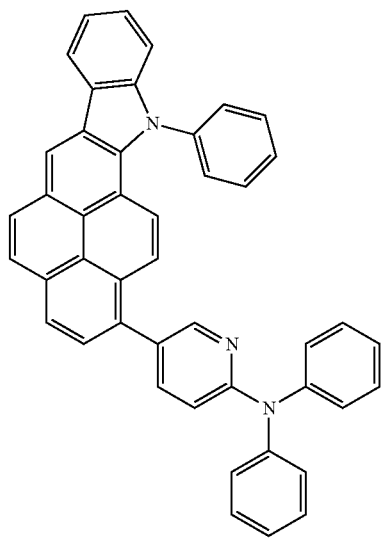 | 133 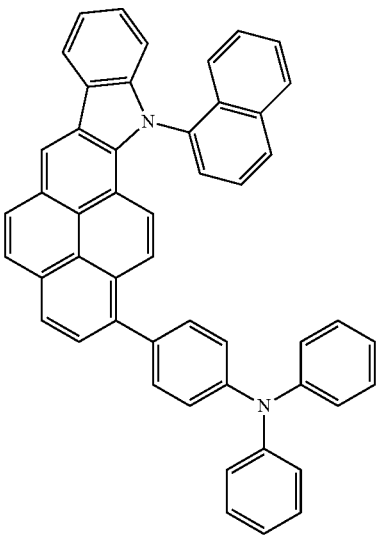 |
| 131 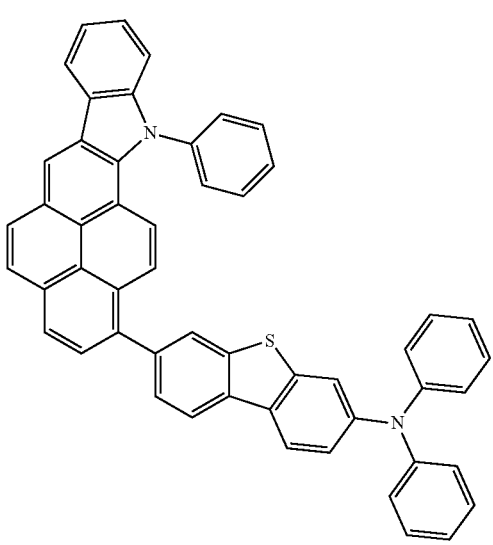 | 134 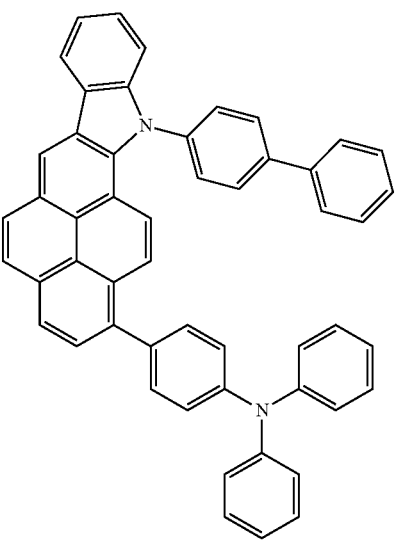 |
| 132 | 135 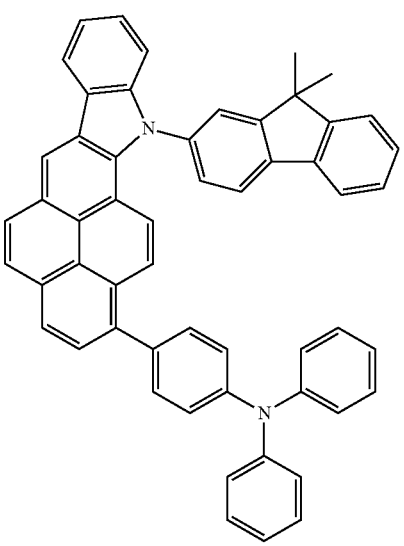 |

136
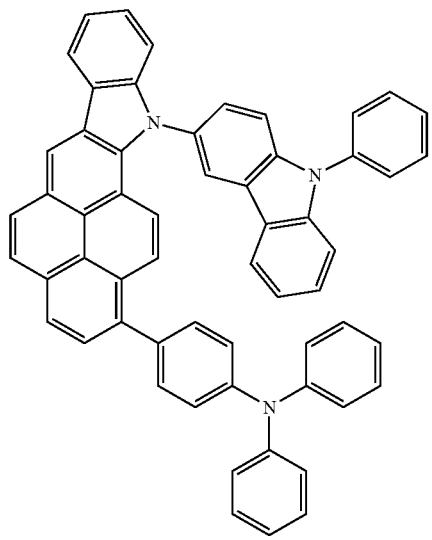
137
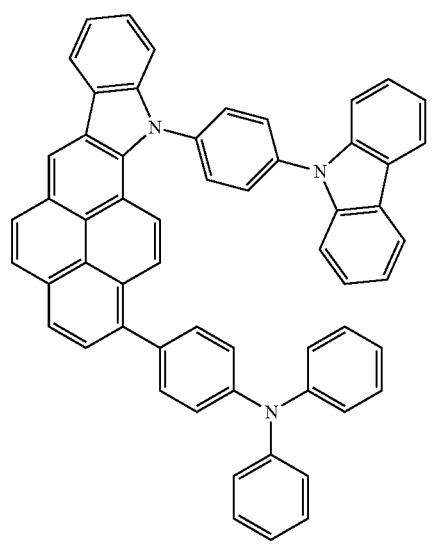
138
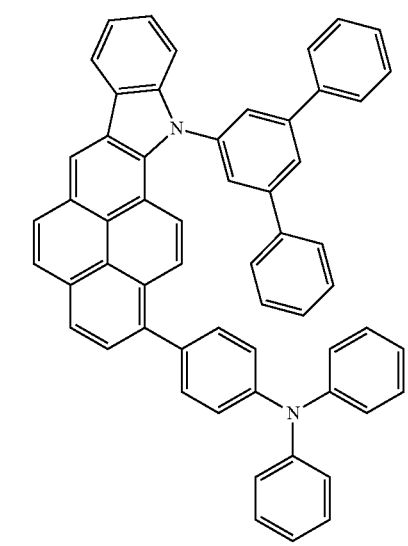
139
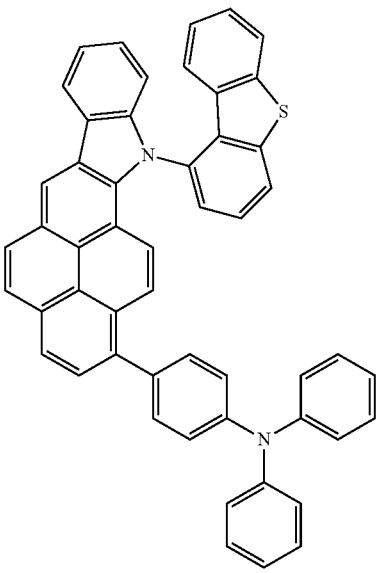
140
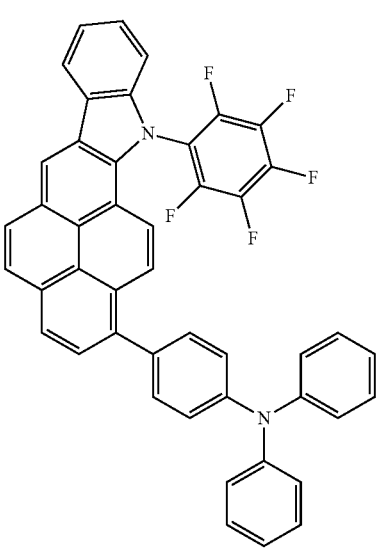
141
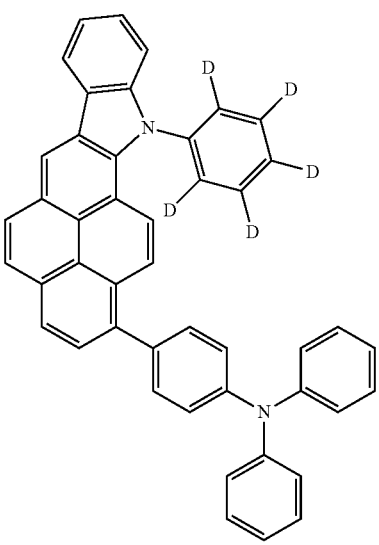

101
-continued
142
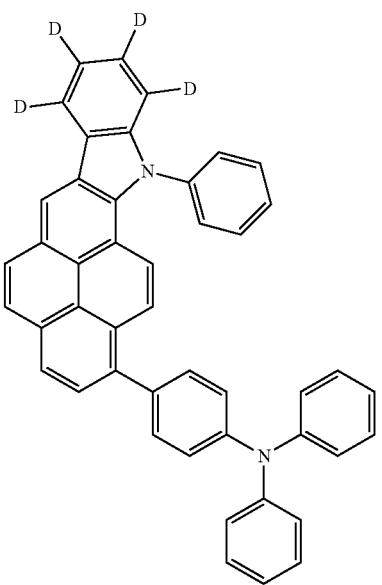
143
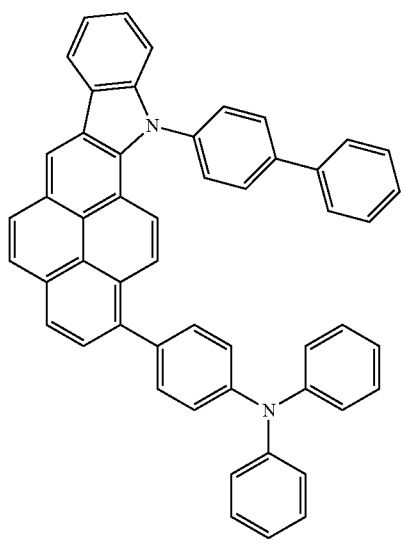
144
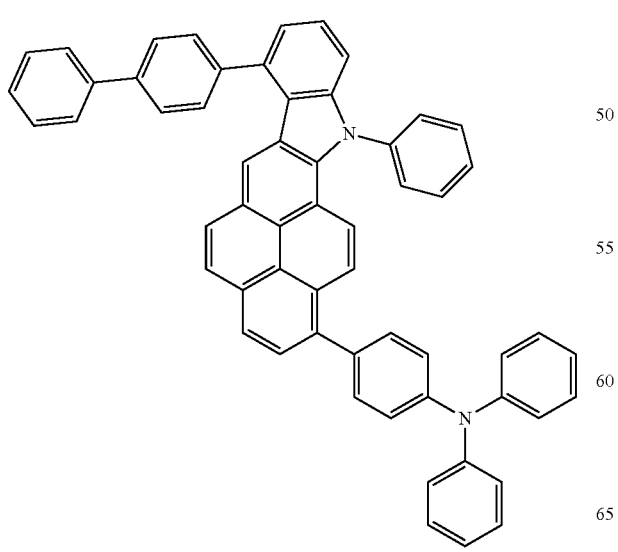
102
-continued
145
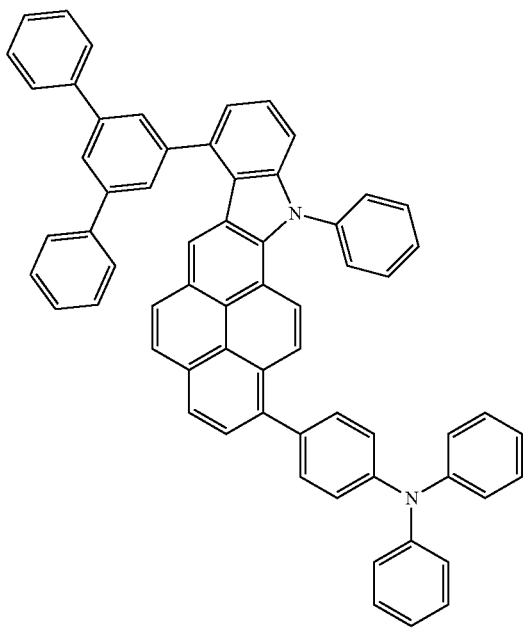
146
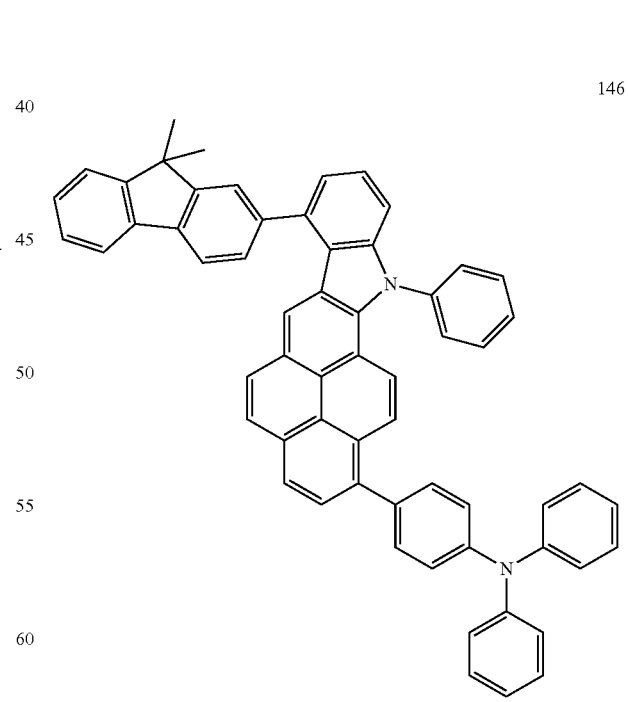

147
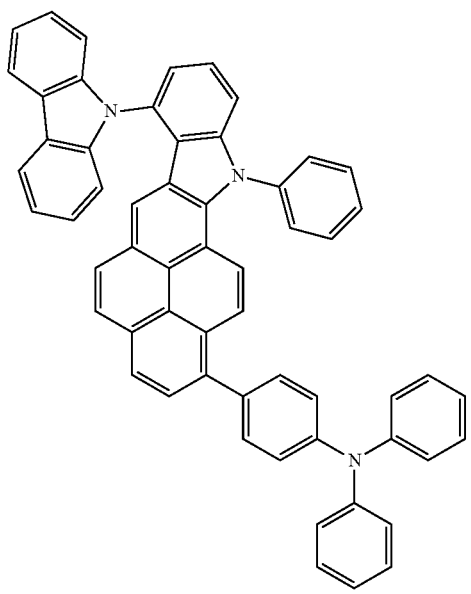
148
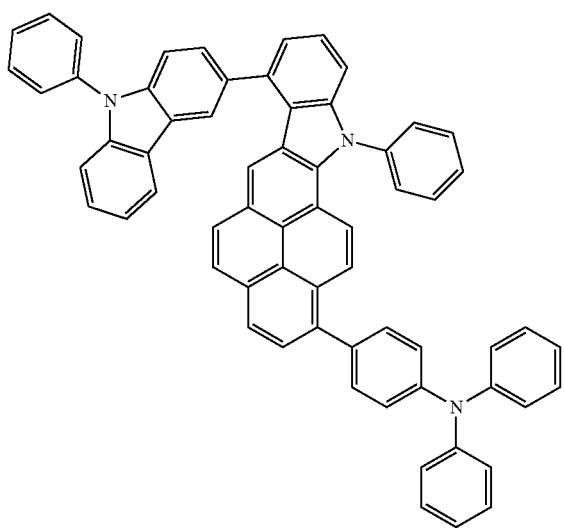
149
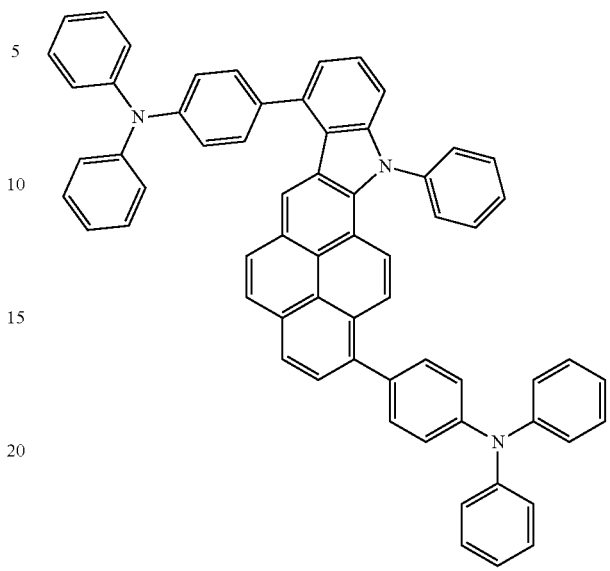
150
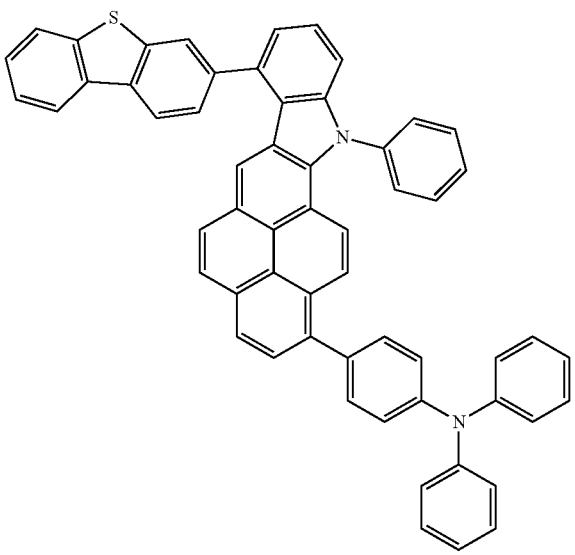

151
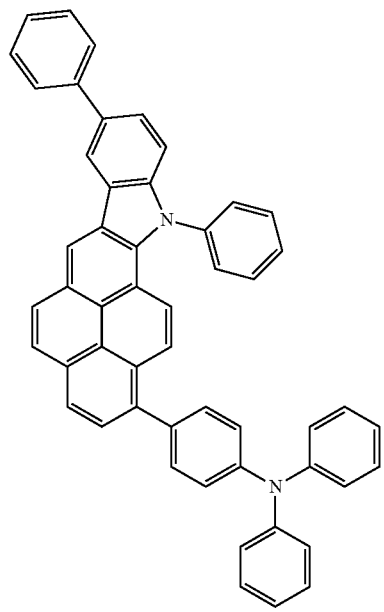
152
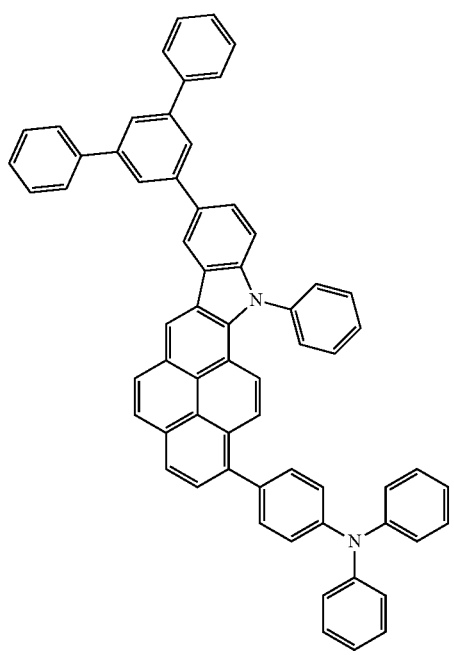
153
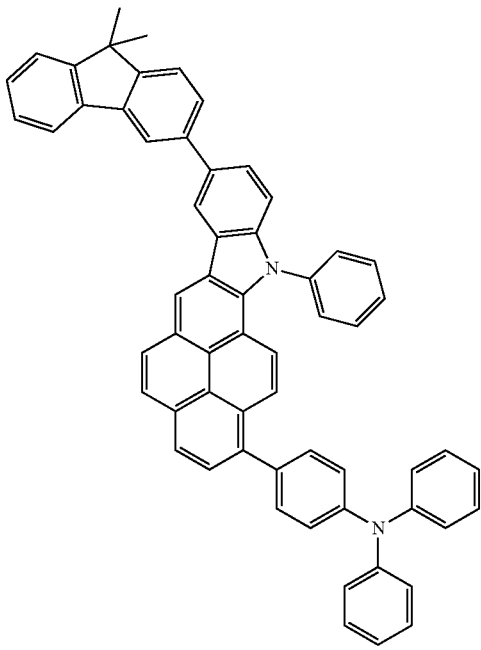
154
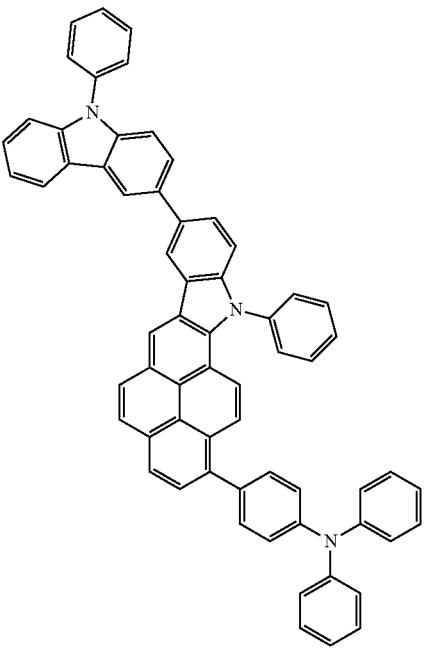

155

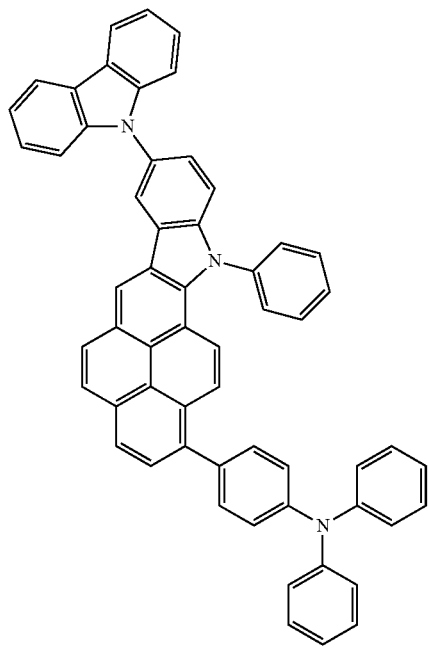

156

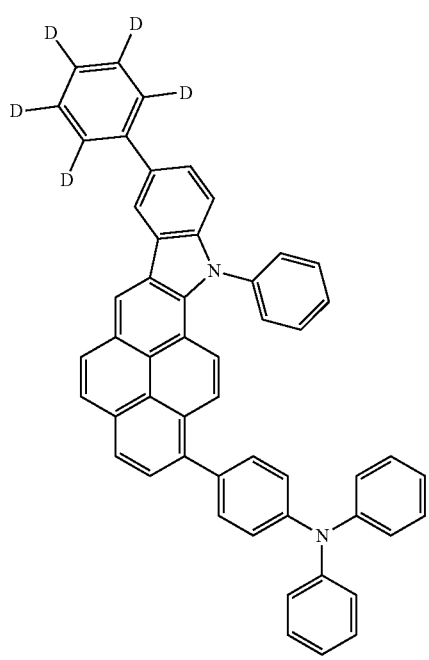

157

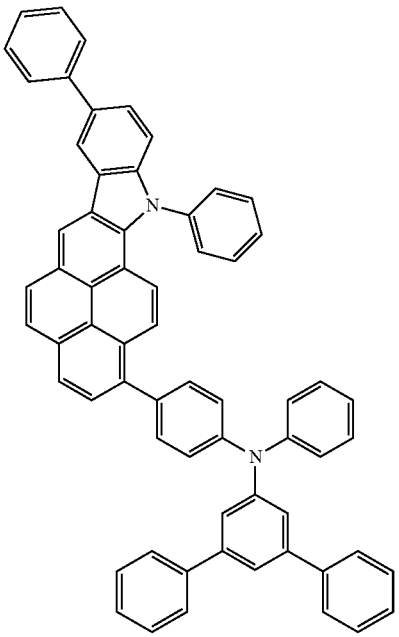

158

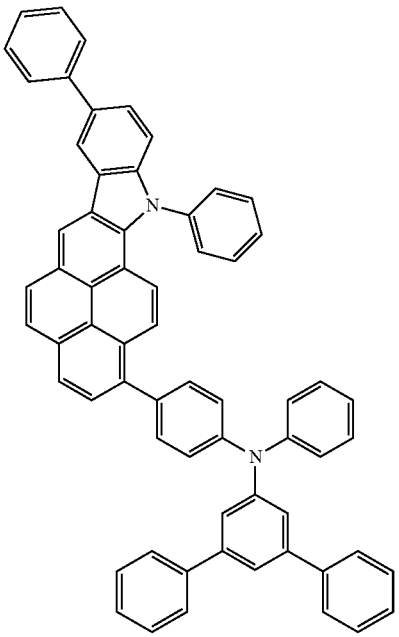

An organic light-emitting device according to an embodiment of the present invention includes a first electrode; a second electrode; and an organic layer interposed between the first electrode and the second electrode, wherein the organic layer includes a first layer including the heterocyclic compound represented by Formula 1 described above.

The first layer including the heterocyclic compound may be a hole injection layer (HIL), a hole transport layer (HTL), a layer having both hole injecting and hole transporting capabilities, an electron injection layer (EEL), an electron transport layer (ETL), or a layer having both electron injecting and electron transporting capabilities.

According to an embodiment of the present invention, the first layer may be an HIL, an HTL, a layer having both hole injecting and hole transporting capabilities, an emission layer (EML), an EIL, an ETL, or a layer having both electron injecting and electron transporting capabilities, wherein the first layer may further include a charge-generating material.

The charge-generating material will be described later.

According to an embodiment of the present invention, the first layer may be an EML, wherein the heterocyclic compound may be used as a host or dopant in the EML, the EML may further include an anthracene compound, an arylamine compound, or a styryl compound, or a red, green, blue, or white layer of the EML may include a phosphorescent compound.

At least one hydrogen atom of the anthracene compound, the arylheterocyclic compound, or the styryl compound may be substituted with the same substituent groups described above with reference to the C1-C50 alkyl group.

The arylamine indicates a C5-C50 arylamine group.

According to an embodiment of the present invention, the first layer may be a blue EML, and the heterocyclic compound may be used as a blue dopant.

The organic layer of the organic light-emitting device may include a HIL, a HTL, a layer having both hole injecting and hole transporting capabilities, an EML, a hole blocking layer (HBL), an ETL, an EIL, or a combination of at least two thereof, but is not limited thereto. At least one of the HIL, the HTL, and the layer having both hole injecting and hole transporting capabilities may further include a charge-generating material in addition to the heterocyclic compound according to the current embodiment, known hole injecting materials, and known hole transporting materials, in order to improve conductivity of the layers. The EML may include a host and a dopant, wherein the dopant may be a fluorescent dopant or a phosphorescent dopant, wherein the phosphorescent dopant may include Ir, Pt, Os, Re, Ti, Zr, Hf, or a combination of at least two thereof.

The charge-generating material may be a p-dopant. Examples of the p-dopant include a quinone derivative such as tetracyanoquinonedimethane (TCNQ) and 2,3,5,6-tetrafluoro-tetracyano-1,4-benzoquinonedimethane (F4TCNQ); a metal oxide such as tungsten oxide and molybdenum oxide; and a cyano group-containing compound such as Compound 100 below, but are not limited thereto:

<Compound 100>

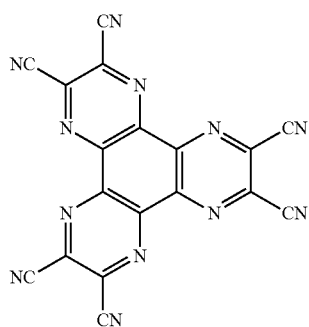

If the HIL, the HTL, or the layer having both hole injecting and hole transporting capabilities further includes the charge-generating material, the charge-generating material may be homogeneously or non-homogeneously dispersed between the layers, or a variety of modifications may be possible.

The ETL of the organic light-emitting device may include an electron-transporting organic compound and a metal-containing material. Examples of the electron-transporting organic compound include anthracene-based compounds such as 9,10-di(naphthalene-2-yl)anthracene) (AND), and Compounds 101 and 102 below, but are not limited thereto.

<Compound 101>

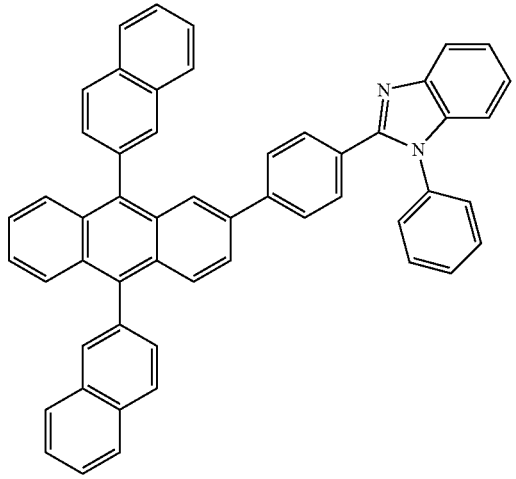

<Compound 102>

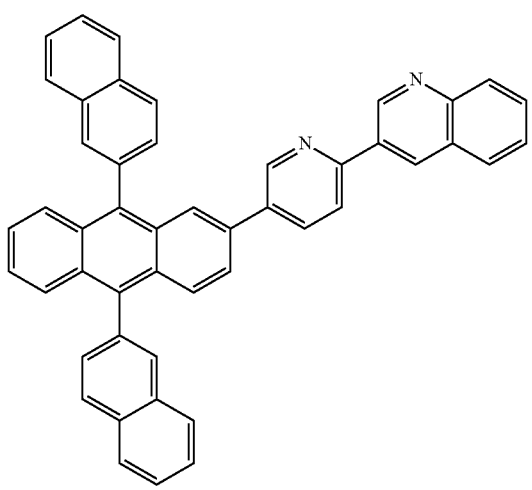

The metal-containing material may include a Li complex. Examples of the Li complex include lithium quinolate (LiQ) or Compound 103 below, but are not limited thereto.

<Compound 103>

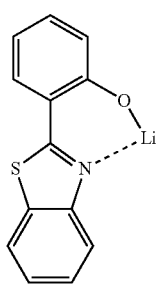

Meanwhile, the first electrode may be an anode, and the second electrode may be a cathode, but the reverse is also possible.

For example, the organic light-emitting device according to the current embodiment may have a structure of first electrode/HIL/EML/second electrode, a structure of first electrode/HIL/HTL/EML/ETL/second electrode, or a structure of first electrode/HIL/HTL/EML/ETL/EIL/second electrode. The organic light-emitting device may also have a structure of first electrode/layer having both hole injecting and hole transporting capabilities/EML/ETL/second electrode, or a structure of first electrode/layer having both hole injecting and hole transporting capabilities/EML/ETL/EIL/second electrode. The organic light-emitting device may also have a structure of first electrode/HTL/EML/layer having both electron injecting and electron transporting capabilities/second electrode, a structure of first electrode/HIL/EML/layer having both electron injecting and electron transporting capabilities/second electrode, or a structure of first electrode/HIL/HTL/EML/layer having both electron injecting and electron transporting capabilities/second electrode.

The organic light-emitting device according to the current embodiment may be a top-emission type organic light-emitting device or a bottom-emission type organic light-emitting device.

Hereinafter, a method of manufacturing an organic light-emitting device according to an embodiment of the present invention will be described with reference to FIG. 1. Referring to FIG. 1, the organic light-emitting device includes a substrate (not shown), a first electrode (anode), a HIL, a HTL, an EML, an ETL, an EIL, and a second electrode (cathode).

First, the first electrode is formed by depositing or sputtering a material for forming the first electrode having a high work function on a substrate. The first electrode may constitute an anode or a cathode. The substrate may be any substrate commonly used in organic light-emitting devices, and may include, for example, a glass substrate or a transparent plastic substrate with excellent mechanical strength, thermal stability, transparency, surface smoothness, ease of handling, and water resistance. The material for forming the first electrode may be indium tin oxide (ITO), indium zinc oxide (IZO), tin oxide ($SnO_2$), zinc oxide (ZnO), aluminum (Al), silver (Ag), magnesium (Mg), or the like, which has excellent conductivity, and may form a transparent or reflective electrode.

Then, a HIL may be formed on the first electrode by vacuum deposition, spin coating, casting, Langmuir Blodgett (LB) deposition, or the like.

When the HIL is formed using vacuum deposition, the deposition conditions may vary according to a compound that is used to form the HIL, and the structure and thermal characteristics of the HIL to be formed. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, coating conditions may vary according to a compound that is used to form the HIL, and the structure and thermal properties of the HIL to be formed. For example, the coating conditions may include a coating speed of about 2000 rpm to about 5000 rpm, and a thermal treatment temperature of about 80° C. to about 200° C., wherein the thermal treatment is for removing a solvent after coating.

The HIL may be formed of the heterocyclic compound of Formula 1 or any material that is commonly used to form a HIL. Examples of the material that can be used to form the HIL include a phthalocyanine compound such as copper-phthalocyanine, 4,4',4''-tris(3-methylphenylphenylamino) triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate) (PANI/PSS), but are not limited thereto.

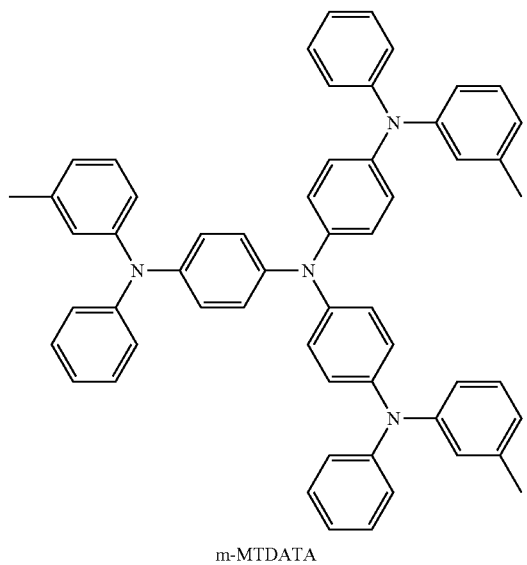

m-MTDATA

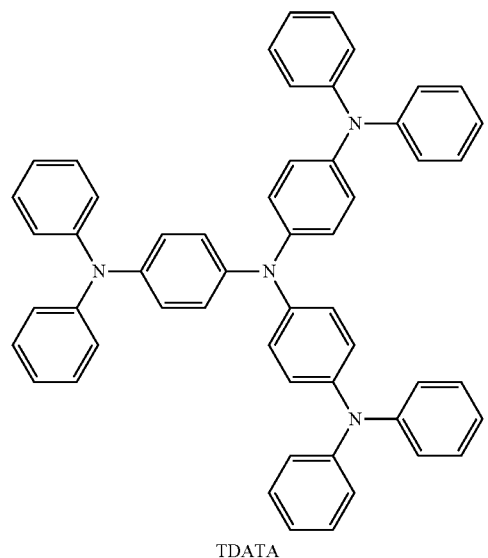

TDATA

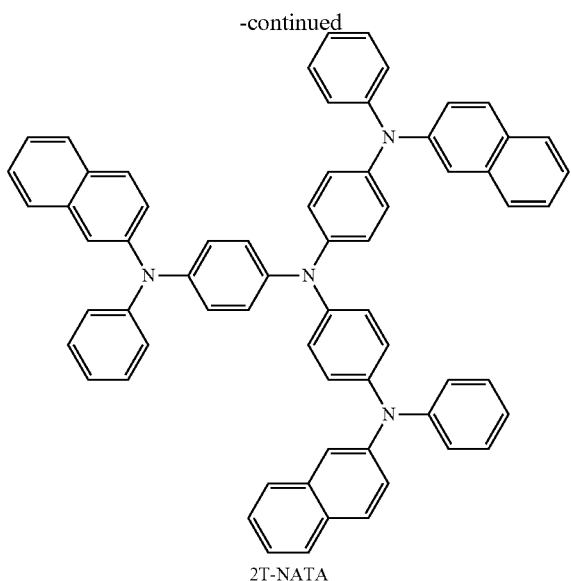

2T-NATA

The thickness of the HIL may be about 100 Å to about 10000 Å, and for example, about 100 Å to about 1000 Å. When the HIL has a thickness within the above range, the HIL may have excellent hole injection characteristics without an increase in driving voltage.

Then, the HTL may be formed on the HIL using various methods, for example by vacuum deposition, spin coating, casting, and LB deposition. When the HTL is formed using vacuum deposition or spin coating, the deposition or coating conditions may be similar to those applied to form the HIL, although the deposition or coating conditions may vary according to a material used to form the HTL.

The HTL may be formed of the heterocyclic compound of Formula 1 or any known HTL material. Examples of such HTL materials include carbazole derivatives such as N-phenylcarbazole or polyvinylcarbazole, and amine derivatives having an aromatic condensed ring, such as NPB, N,N'-bis(3-methylphenyl)-N,N'-diphenyl-[1,1-biphenyl]-4,4'-diamine (TPD), or the like.

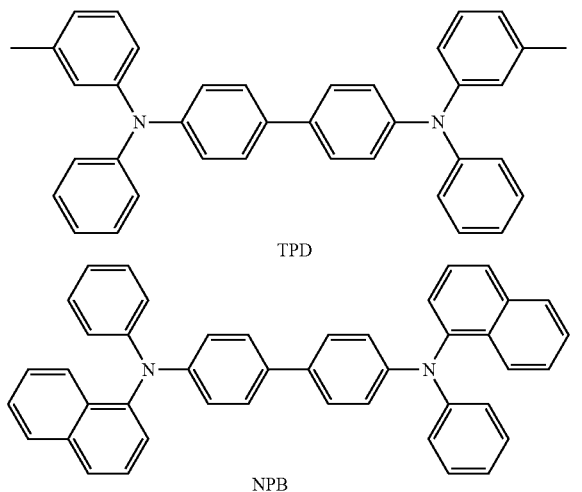

TPD

NPB

The HTL may have a thickness of about 50 Å to about 1000 Å, for example, about 100 Å to about 600 Å. When the HTL has a thickness within the above range, the HTL may have excellent hole transporting characteristics without a substantial increase in driving voltage.

Then, the EML may be formed on the HTL using various methods, for example, vacuum deposition, spin coating, casting, and LB deposition. When the EML is formed using vacuum deposition or spin coating, the deposition or coating conditions may be similar to those applied to form the HIL, although the deposition and coating conditions may vary according to a material that is used to form the EML.

The EML may include the heterocyclic compound according to an embodiment of the present invention. For example, the heterocyclic compound according to an embodiment of the present invention may be used as a host or dopant. The EML may be formed using a variety of well-known light-emitting materials, in addition to the heterocyclic compound according to an embodiment of the present invention. Alternatively, the EML may also be formed using well-known hosts and dopants. The dopant for forming the EML may include either a fluorescent dopant or a phosphorescent dopant, which are widely known in the art.

Examples of the host include Alq3, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphtha-2-yl)anthracene (TBADN), E3, and distyrylarylene (DSA), but are not limited thereto.

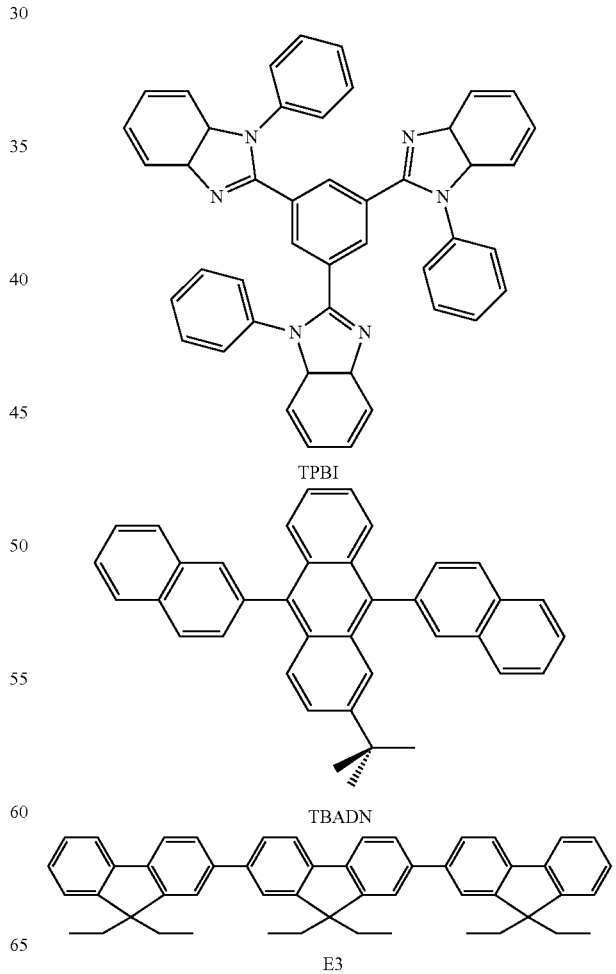

TPBI

TBADN

E3

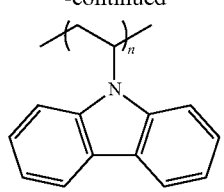

PVK

Examples of well-known red dopants include platinum(II) octaethylporphyrin (PtOEP), Ir(piq)₃, Btp₂Ir(acac), and DCJTB, but are not limited thereto.

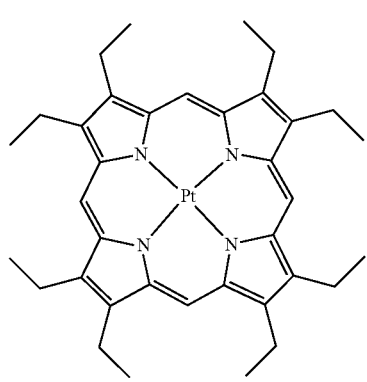

PtOEP

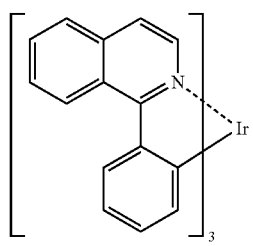

Ir(piq)₃

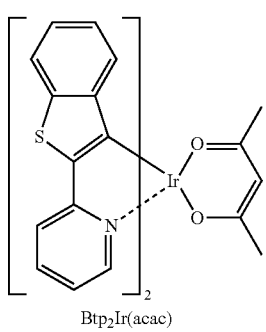

Btp₂Ir(acac)

Examples of known green dopants include Ir(ppy)₃ (where "ppy" denotes phenylpyridine), Ir(ppy)₂(acac), Ir(mpyp)₃, and C545T, but are not limited thereto.

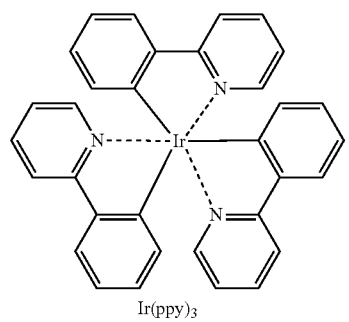

Ir(ppy)₃

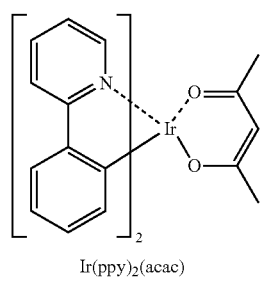

Ir(ppy)₂(acac)

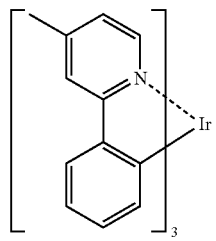

Ir(mpyp)₃

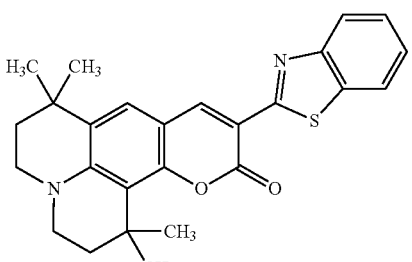

C545T

Meanwhile, examples of the blue dopant include the heterocyclic compound according to an embodiment of the present invention, or known blue dopants such as F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl pherylene (TBPe), but are not limited thereto.

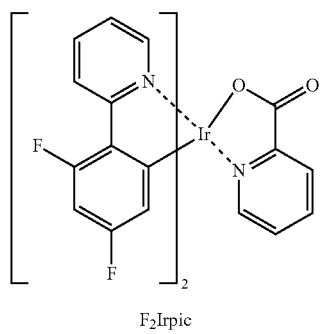

F₂Irpic

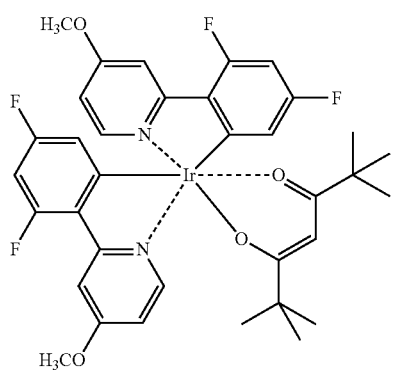

(F₂ppy)₂Ir(tmd)

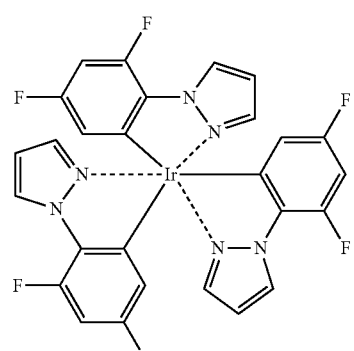

Ir(dfppz)₃

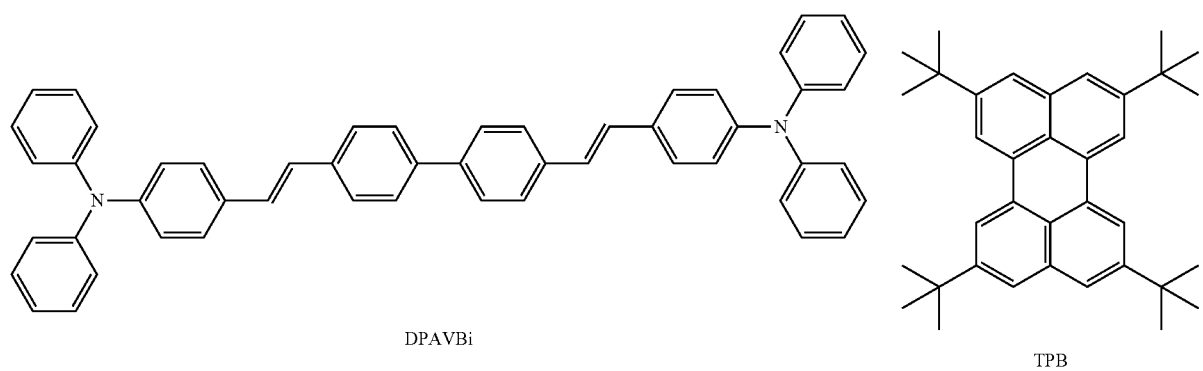

DPAVBi

TPB

The amount of the dopant may be in a range of about 0.1 to about 20 parts by weight, or about 0.5 to about 12 parts by weight, based on 100 parts by weight of the EML material (which is equivalent to the total weight of the host and the dopant). When the amount of the dopant is within the above range, concentration quenching may be substantially prevented.

The EML may have a thickness of about 100 Å to about 1000 Å, for example, about 200 Å to about 600 Å. When the EML has a thickness within the above range, the EML may have excellent light-emitting characteristics without a substantial increase in driving voltage.

When the EML includes a phosphorescent dopant, an HBL (not shown in FIG. 1) may be formed on the EML in order to prevent diffusion of triplet excitons or holes into the ETL. In this case, the HBL may be formed of any material that is commonly used to form a HBL, without limitation. Examples of such HBL materials include oxadiazole derivatives, triazole derivatives, phenathroline derivatives, Balq, and BCP.

The HBL may have a thickness of about 50 Å to about 1000 Å, for example, about 100 Å to about 300 Å. When the thickness of the HBL is within these ranges, diffusion of triplet excitons or holes into the ETL may be readily prevented without a substantial increase in driving voltage.

Then, the ETL is formed on the EML (or HBL) using various methods, for example, by vacuum deposition, spin coating, casting, or the like. When the ETL is formed using vacuum deposition or spin coating, the deposition or coating conditions may be similar to those applied to form the HIL, although the deposition and coating conditions may vary according to the material that is used to form the ETL.

A material for forming the ETL may be the heterocyclic compound according to an embodiment of the present invention. Alternatively, the ETL may be formed of any material that is widely known in the art. Examples of electron transporting materials include quinoline derivatives, such as tris (8-quinolinolate)aluminum (Alq3), TAZ, or BAlq, but are not limited thereto.

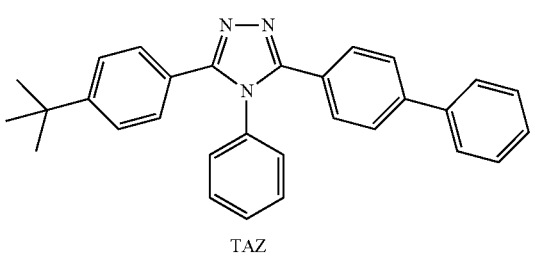

TAZ

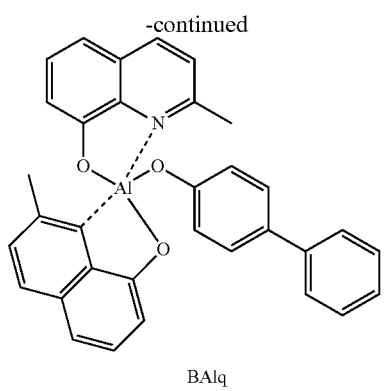

BAlq

The ETL may have a thickness of about 100 Å to about 1000 Å, for example, about 100 Å to about 500 Å. When the ETL has a thickness within the above range, the ETL may have excellent electron transporting characteristics without a substantial increase in driving voltage.

In addition, the EIL, which facilitates injection of electrons from the cathode, may be formed on the ETL.

The EIL may be formed using the heterocyclic compound according to an to embodiment of the present invention or known materials such as LiF, NaCl, CsF, $Li_2O$, and BaO. The deposition or coating conditions for forming the EIL may be similar to those applied to form the HIL, although the deposition and coating conditions may vary according to the material that is used to form the EIL.

The EIL may have a thickness of about 1 Å to about 100 Å, for example, about 5 Å to about 90 Å. When the EIL has a thickness within the above range, the EIL may have excellent electron injecting 16 injecting characteristics without a substantial increase in driving voltage.

Finally, the second electrode may be formed on the EIL using, for example, vacuum deposition, sputtering, or the like. The second electrode may constitute a cathode or an anode. The material for forming the second electrode may include a metal, an alloy, or an electrically conductive compound which has a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like. In addition, in order to manufacture a top-emission type organic light-emitting device, a transparent cathode formed of a transparent material such as ITO or IZO may be used as the second electrode.

If the organic layer of the organic light-emitting device according to an embodiment of the present invention has a plurality of organic layers, at least one of the organic layers may be formed of the heterocyclic compound according to the current embodiment by using a deposition method or a wet process of coating a solution of the heterocyclic compound according to the current embodiment.

The organic light-emitting device according to the current embodiment may be applied to various types of flat panel display devices, such as in a passive matrix organic light-emitting display device or an active matrix organic light-emitting display device. In particular, when the organic light-emitting device is applied to an active matrix organic light-emitting display device including a thin-film transistor, the first electrode formed on the substrate may function as a pixel electrode, electrically connected to a source electrode or a drain electrode of the thin-film transistor. Moreover, the organic light-emitting device may also be applied to a flat panel display device having a double-sided screen.

Hereinafter, the present invention will be described in detail with reference to synthesis examples of Compounds 2, 11, 24, 33, 45, 48, 55, 57, 73, and 82 represented by Formula 2 and Compounds 87, 89, 95, 105, 108, 124, 141, 146, and 158 represented by Formula 3 and other examples. However, these examples are for illustrative purpose only and are not intended to limit the scope of the present invention.

EXAMPLES

Synthesis Example 1

Synthesis of Compound 2

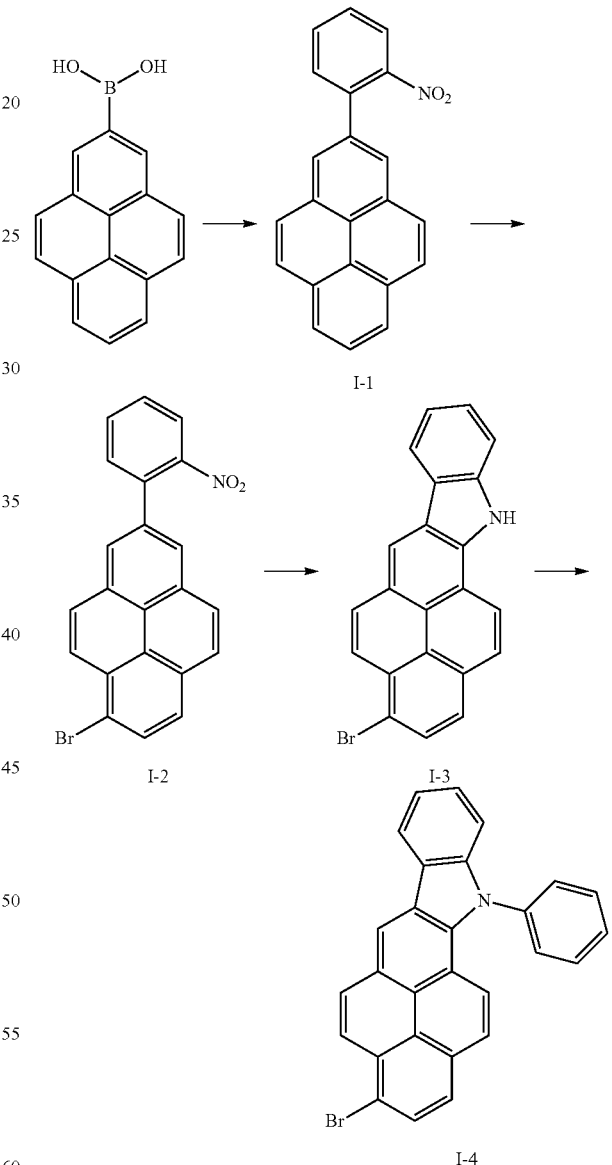

Synthesis of Intermediate I-1

4.93 g (20.0 mmol) of 2-pyrene boronic acid, 4.04 g (20.0 mmol) of 2-bromonitrobenzene, 1.15 g (1.0 mmol) of $Pd(PPh_3)_4$, and 8.29 g (60.0 mmol) of $K_2CO_3$ were dissolved in 60 mL of a THF/H$_2$O (2/1) solution, and the mixture was stirred at 70° C. for 5 hours. The mixture was cooled to room temperature, 40 mL of water was added thereto, and the mixture was subjected to extraction three times with 50 mL of ethyl ether. An organic layer was collected and dried using magnesium sulfate to evaporate the solvent. The residue was separately purified using silica gel column chromatography to obtain 5.95 g of Intermediate I-1 (Yield: 92%) The produced compound was identified using LC-MS. C$_{22}$H$_{13}$NO$_2$ Calc.: 323.1; Measured [M+1] 324.1

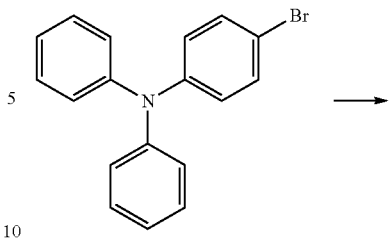

Synthesis of Intermediate I-2

4.85 g (15.0 mmol) of Intermediate I-1 was dissolved in 100 mL of dichloromethane, and 1.75 mL (15.0 mmol) of bromine (Br$_2$) was gradually added thereto at 0° C. The mixture was stirred at room temperature for 12 hours. 60 mL of water and 30 mL of a 20% sodium thiosulfate solution were added thereto. Then, the mixture was subjected to extraction three times with 80 mL of dichloromethane. An organic layer was collected and dried using magnesium sulfate to evaporate the solvent. The residue was separately purified using silica gel column chromatography and recrystallized using a dichloromethane/hexane solution to obtain 3.38 g of Intermediate I (Yield: 56%) The produced compound was identified using LC-MS. C$_{22}$H$_{12}$BrNO$_2$ Calc.: 401.0; Measured [M+1] 402.0

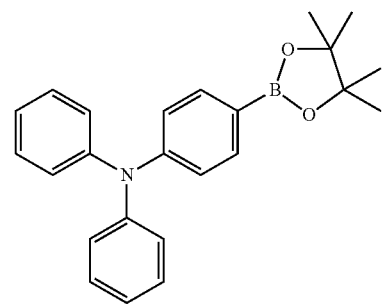

I-5

Synthesis of Intermediate I-3

4.02 g (10.0 mmol) of Intermediate I-2 and 5.77 g (22 mmol) of triphenylphosphine (PPh$_3$) were dissolved in 30 mL of 1,2-dichlorobenzene, and the mixture was stirred at 170° C. for 12 hours. The mixture was cooled to room temperature, the solvent was removed in a vacuum, and the mixture was subjected to extraction three times with 50 mL of water and 50 mL of dichloromethane. An organic-layer was collected and dried using magnesium sulfate to evaporate the solvent. The residue was separately purified using silica gel column chromatography to obtain 2.66 g of Intermediate I-3 (Yield: 72%) The produced compound was identified using LC-MS. C$_{22}$H$_{12}$BrN Calc.: 369.0; Measured [M+1] 370.0

Synthesis of Intermediate I-4

3.70 g (10.0 mmol) of Intermediate I-3, 3.06 g (15.0 mmol) of iodobenzene, 0.19 g (1.0 mmol) of CuI, 0.05 g (0.2 mmol) of 18-Crown-6, and 4.15 g (30.0 mmol) of K$_2$CO$_3$ were dissolved in 30 mL of 1,3-dimethyl-3,4,5,6-tetrahydro-3(1H)-pyrimidinone (DMPU), and the mixture was stirred at 170° C. for 12 hours. The mixture was cooled to room temperature and subjected to extraction three times with 50 mL of water and 50 mL of dichloromethane. An organic layer was collected and dried using magnesium sulfate to evaporate the solvent. The residue was separately purified using silica gel column chromatography to obtain 4.15 g of Intermediate I-4 (Yield: 93%) The produced compound was identified using LC-MS. C$_{28}$H$_{16}$BrN Calc.: 445.0; Measured [M+1] 446.0

Synthesis of Intermediate I-5

3.24 g (10.0 mmol) of 4-bromotriphenylamine, 2.54 g (10.0 mmol) of bis(pinacolato)diborone, 0.36 g (0.5 mmol) of 1,1'-bis(diphenylphosphino)ferrocene]dichloro palladium (II) (PdCl$_2$(dppf)$_2$), and 2.94 g (30.0 mmol) of KOAc were dissolved in 40 mL of dimethyl sulfoxide (DMSO), and the mixture was stirred at 80° C. for 6 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 2.57 g of Intermediate I-5 (Yield: 89%) The produced compound was identified using LC-MS. C$_{24}$H$_{76}$BNO$_2$ Calc.: 371.2; Measured [M+1] 372.2

Synthesis of Compound 2

2.23 g (5.0 mmol) of Intermediate I-4, 1.86 g (5.0 mmol) of Intermediate I-5, 0.29 g (0.25 mmol) of Pd(PPh$_3$)$_4$, and 2.07 g (15.0 mmol) of K$_2$CO$_3$ were dissolved in 30 mL of a THF/H$_2$O (2/1) solution, and the mixture was stirred at 70° C. for 5 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 2.11 g of Compound 2 (Yield: 69%). The produced compound was identified using HR-MS. C$_{46}$H$_{30}$N$_2$ Calc.: 610.2409; Measured [M+1] 611.2401

$^1$H NMR (CDCl$_3$, 400 MHz) δ (ppm) 9.25-9.21 (d, 1H), 8.92-8.85 (m, 1H), 8.66-8.62 (d, 1H), 8.26-8.24 (d, 1H), 8.17

(s, 1H), 8.07 (s, 2H), 8.01-7.98 (d, 1H), 7.76-7.74 (d, 4H), 7.62-7.56 (m, 6H), 7.39-7.23 (m, 10H), 7.12-7.00 (dt, 2H)

Synthesis Example 2

Synthesis of Compound I1

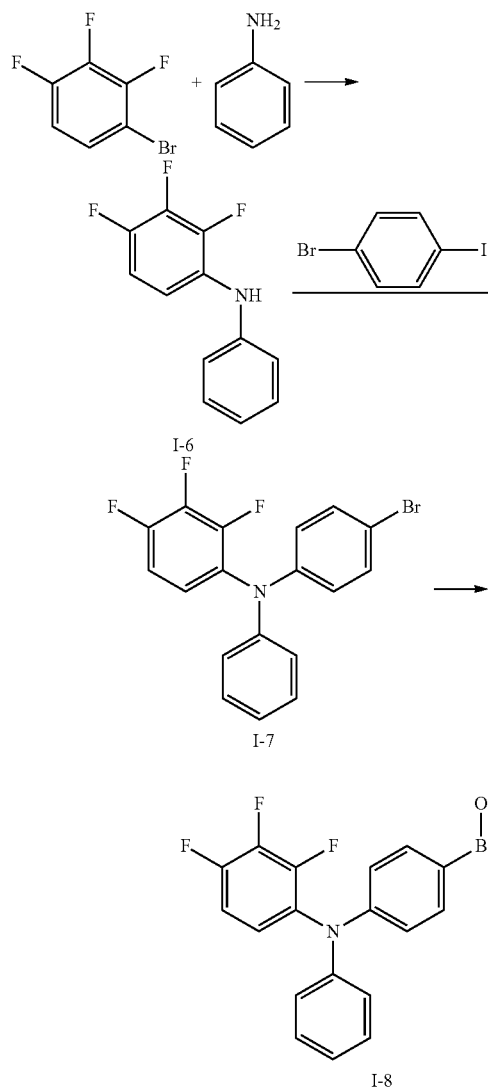

Synthesis of Intermediate I-6

4.22 g (20.0 mmol) of 1-bromo-2,3,4-trifluorobenzene, 2.79 g (30.0 mmol) of aniline, 0.37 g (0.4 mmol) of $Pd_2(dba)_3$, 0.08 g (0.4 mmol) of $PtBu_3$, and 2.88 g (30.0 mmol) of KOtBu were dissolved in 60 mL of toluene, and the mixture was stirred at 85° C. for 4 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 3.93 g of Intermediate I-6 (Yield: 88%) The produced compound was identified using LC-MS. $C_{12}H_8F_3N$ Calc.: 223.1; Measured [M+1] 224.1

Synthesis of Intermediate I-7

3.45 g (15.0 mmol) of Intermediate I-6, 2.83 g (10.0 mmol) of 4-bromoiodobenzene, 0.18 g (0.2 mmol) of $Pd_2(dba)_3$, 0.04 g (0.4 mmol) of $PtBu_3$, and 1.44 g (15.0 mmol) of KOtBu were dissolved in 40 mL of toluene, and the mixture was stirred at 85° C. for 4 hours. The mixture was cooled to room temperature and subjected to extraction three times with 30 mL of water and 30 mL of diethyl ether. An organic layer was collected and dried using magnesium sulfate to evaporate the solvent. The residue was separately purified using silica gel column chromatography to obtain 2.38 g of Intermediate I-7 (Yield: 63%) The produced compound was identified using LC-MS. $C_{18}H_{11}BrF_3N$ Calc.: 377.0; Measured [M+1] 378.0

Synthesis of Intermediate I-8

3.78 g (10.0 mmol) of Intermediate I-7, 2.54 g (10.0 mmol) of bis(pinacolato)diborone, 0.36 g (0.5 mmol) of $PdCl_2(dppf)_2$, and 2.94 g (30.0 mmol) of KOAc were dissolved in 40 mL of DMSO, and the mixture was stirred at 80° C. for 6 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 3.40 g of Intermediate I-8 (Yield: 80%) The produced compound was identified using LC-MS. $C_{24}H_{23}BF_3NO_2$ Calc.: 425.2; Measured [M+1] 426.2

Synthesis of Compound 11

Compound 11 was synthesized in the same manner as in the synthesis of Compound 2 using Intermediate I-4 and Intermediate I-8. The produced compound was identified using HR-MS. $C_{46}H_{27}F_3N_2$ Calc.: 664.2126; Measured [M+1] 665.2124

$^1$H NMR (CDCl$_3$, 400 MHz) δ (ppm) 8.80-8.78 (d, 1H), 8.44-8.41 (d, 1H), 8.23-8.20 (m, 1H), 8.10-8.07 (d, 1H), 8.04 (s, 1H), 8.00-7.99 (d, 1H), 7.95-7.88 (m, 2H), 7.56-7.53 (m, 2H), 7.91-7.47 (m, 3H), 7.35-7.29 (m, 8H), 6.64-6.60 (m, 1H), 6.45-6.43 (d, 2H), 6.35-6.33 (d, 1H), 5.71-5.70 (d, 1H)

Synthesis Example 3

Synthesis of Compound 24

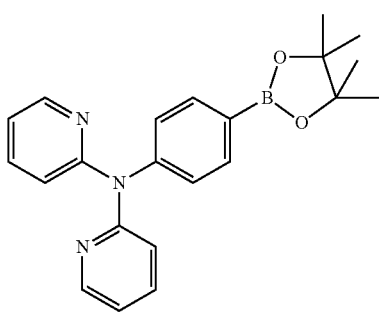

I-9

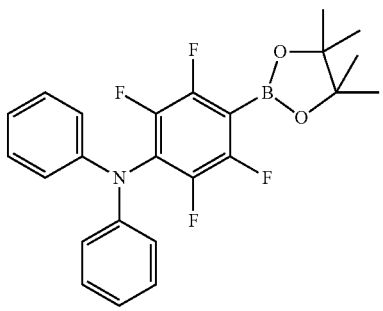

I-10

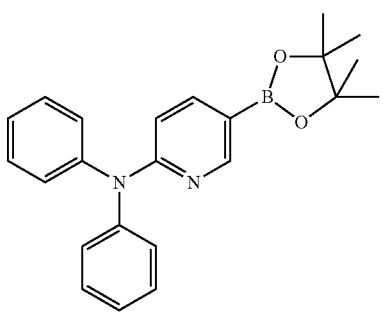

I-11

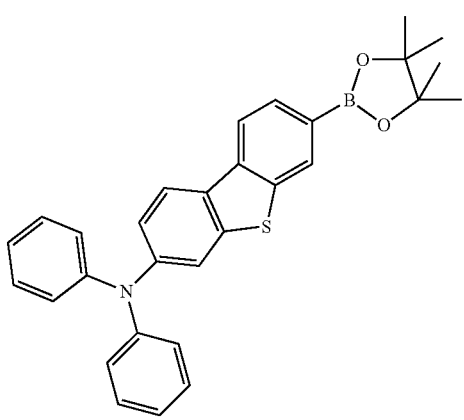

I-12

Synthesis of Intermediate I-9

Intermediate I-9 was synthesized using 2-aminopyridine and 2-bromopyridine in the same manner as in the synthesis of Intermediates I-7 and I-8 by synthesizing Intermediate I-6. The produced compound was identified using LC-MS. $C_{22}H_{24}BN_3O_2$ Calc.: 373.2; Measured [M+1] 374.2

Synthesis of Intermediate I-10

Intermediate I-10 was synthesized in the same manner as in the synthesis of Intermediate I-9 using diphenylamine and 1,4-dibromo-tetrafluorobenzene. The produced compound was identified using LC-MS. $C_{24}H_{22}BF_4NO_2$ Calc.: 443.2; Measured [M+1] 444.2

Synthesis of Intermediate I-11

Intermediate I-11 was synthesized in the same manner as in the synthesis of Intermediate I-9 using diphenylamine and 2-dibromo-iodopyridine. The produced compound was identified using LC-MS. $C_{23}H_{25}BN_2O_2$ Calc.: 372.2; Measured [M-1] 373.2

Synthesis of Intermediate I-12

Intermediate I-12 was synthesized in the same manner as in the synthesis of Intermediate I-9 using diphenylamine and 3,7-dibromo-dibenzothiophene The produced compound was identified using LC-MS. $C_{30}H_{28}BNO_2S$ Calc.: 477.2; Measured [M+1] 478.2

Synthesis of Compound 24

Compound 24 was synthesized in the same manner as in the synthesis of Compound 2 using Intermediate I-4 and Intermediate I-9. The produced compound was identified using HR-MS. $C_{44}H_{28}N_4$ Calc.: 612.2314; Measured [M+1] 613.2310

$^1$H NMR (CDCl$_3$, 400 MHz) δ (ppm) 8.80 (d, 1H), 8.44-8.41 (d, 1H), 8.23-8.20 (m, 2H), 8.10-8.07 (d, 1H), 8.04 (s, 1H), 8.00-7.98 (d, 1H), 7.94-7.88 (m, 2H), 7.58-7.51 (m, 3H), 7.50-7.47 (m, 6H), 7.37-7.29 (m, 6H), 7.01-6.97 (m, 2H), 6.91-6.89 (dd, 2H)

Synthesis Example 4

Synthesis of Compound 34

Compound 34 was synthesized in the same manner as in the synthesis of Compound 2 using Intermediate I-4 and Intermediate I-10. The produced compound was identified using HR-MS. $C_{46}H_{26}F_4N_2$ Calc.: 682.2032; Measured [M+1] 683.2029

$^1$H NMR (CDCl$_3$, 400 MHz) δ (ppm) 8.79-8.77 (d, 1H), 8.40-8.39 (d, 1H), 8.25-8.22 (m, 1H), 8.14-8.11 (d, 1H), 8.06-8.01 (m, 2H), 7.93-7.91 (d, 1H), 7.59-7.57 (d, 1H), 7.51-7.46 (m, 4H), 7.35-7.31 (m, 8H), 6.64-6.60 (t, 2H), 5.73-5.71 (m, 4H)

Synthesis Example 5

Synthesis of Compound 45

Compound 45 was synthesized in the same manner as in the synthesis of Compound 2 using Intermediate I-4 and Intermediate I-11. The produced compound was identified using HR-MS. $C_{45}H_{29}N_3$ Calc.: 611.2361; Measured [M+1] 612.2357

$^1$H NMR (CDCl$_3$, 400 MHz) δ (ppm) 8.93-8.91 (m, 1H), 8.77-8.75 (d, 1H), 8.43-8.42 (d, 1H), 8.23-8.19 (m, 2H), 8.17-8.11 (m, 3H), 8.07-8.01 (m, 3H), 5.55-7.46 (m, 8H), 7.33-7.26 (m, 3H), 7.01-6.96 (m, 2H), 6.93-6.90 (m, 4H), 6.61-6.58 (d, 1H)

Synthesis Example 6

Synthesis of Compound 48

Compound 48 was synthesized in the same manner as in the synthesis of Compound 2 using Intermediate I-4 and Intermediate I-12. The produced compound was identified using HR-MS. $C_{52}H_{32}N_2S$ Calc.: 716.2286; Measured [M+1] 717.2281

$^1$H NMR (CDCl$_3$, 400 MHz) δ (ppm) 8.74-8.72 (d, 1H), 8.39-8.37 (d, 1H), 8.22-8.17 (m, 3H), 8.13-8.04 (m, 5H), 7.98-7.96 (d, 1H), 7.72-7.70 (d, 1H), 7.54-7.45 (m, 5H), 7.37-7.27 (m, 8H), 7.04-6.98 (m, 1H), 6.66-6.60 (m, 2H), 6.23-6.21 (d, 4H)

Synthesis Example 7

Synthesis of Compound 55

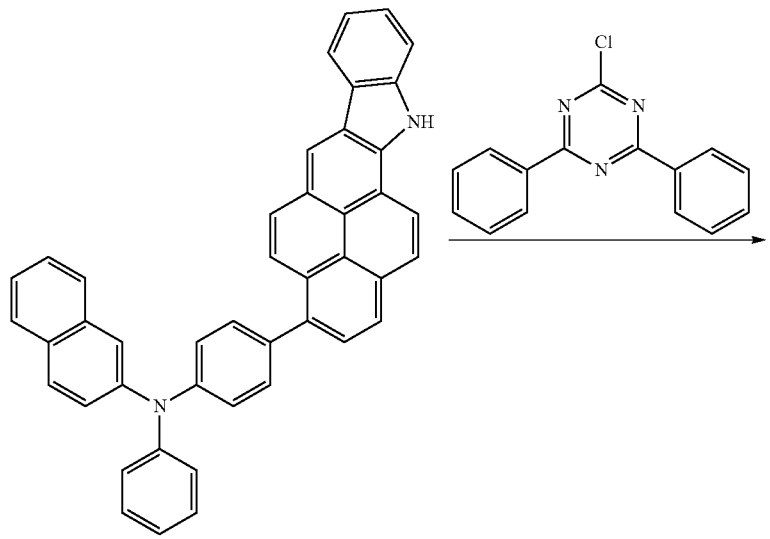

I-13

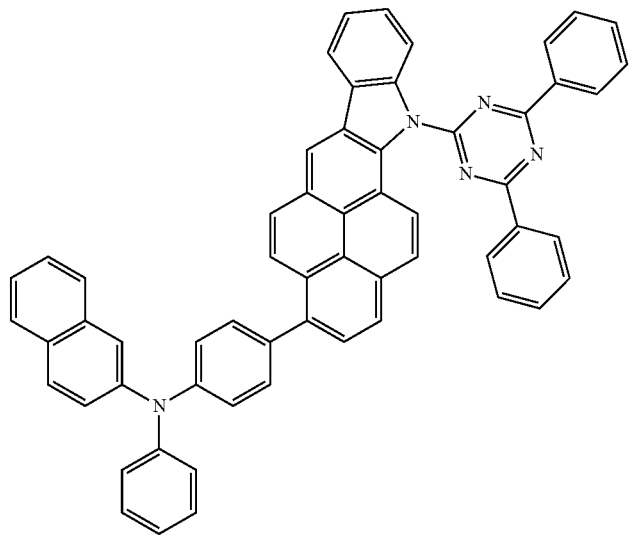

55

Synthesis of Compound 55

A secondary amine was synthesized in the same manner as in the synthesis of Intermediate I-8 using 2-bromonaphthalene and aniline and subjected to a Suzuki coupling with 4-bromo-1-iodobenzene. Then, a boron compound was synthesized using bis(pinacolato)diborone and PdCl$_2$(dppf)$_2$. Then, the boron compound was reacted with Intermediate I-3 to synthesize Intermediate I-13.

A solution prepared by dissolving 2.92 g (5.0 mmol) of Intermediate I-13 in 20 mL of DMF was slowly added to a solution prepared by dissolving 0.6 g (15.0 mmol) of 60% sodium hydride (NaH) in 10 mL of DMF for 10 minutes. The mixture was maintained at room temperature for 1 hour, and a solution prepared by dissolving 2.67 g (10.0 mmol) of 2-chloro-4,6-diphenyl-(1,3,5)-triazine in 10 mL of DMF was slowly added to the mixture for 30 minutes, and the resultant was stirred at room temperature for 3 hours. After the reaction was terminated, the resultant was subjected to extraction three times with 60 mL of water and 60 mL of diethyl ether. An organic layer was collected and dried using magnesium sulfate to evaporate the solvent. The residue was separately purified using silica gel column chromatography to obtain 3.83 g of Compound 55 (Yield: 47%). The produced compound was identified using HR-MS. $C_{59}H_{37}N_5$ Calc.: 815.3049; Measured [M+1] 816.3044

$^1$H NMR (CDCl$_3$, 400 MHz) δ (ppm) 8.85-8.78 (m, 3H), 8.59-8.56 (m, 4H), 8.44-8.41 (d, 1H), 8.22-8.21 (d, 1H), 8.08-7.98 (m, 2H), 7.94-7.86 (m, 3H), 7.70-7.62 (m, 2H), 7.57-7.50 (m, 3H), 7.47-7.25 (m, 11H), 7.16-7.11 (m, 1H), 6.87-6.79 (m, 1H), 6.63-6.59 (m, 3H), 6.12-6.09 (m, 2H)

Synthesis Example 8

Synthesis of Compound 57

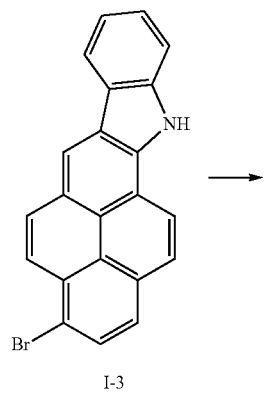

I-3

Intermediate I-14 was synthesized in the same manner as in the synthesis of Intermediate I-4 using bromopentafluorobenzene, and Compound 57 was synthesized in the same manner as in the synthesis of Compound 2 using Intermediate I-14 and Intermediate I-5. The produced compound was identified using HR-MS. $C_{45}H_{25}F_5N_2$ Calc.: 700.1938; Measured [M+1] 701.1932

$^1$H NMR (CDCl$_3$, 400 MHz) δ (ppm) 8.70-8.68 (d, 1H), 8.34-8.31 (d, 1H), 8.16-8.14 (m, 1H), 8.05-8.02 (m, 2H), 7.80-7.78 (d, 1H), 7.70-7.58 (m, 2H), 7.41-7.23 (m, 8H), 6.86-6.82 (m, 3H), 6.65-6.61 (m, 2H), 5.99-5.97 (m, 4H)

Synthesis Example 9

Synthesis of Compound 73

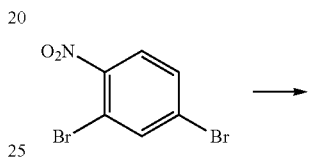

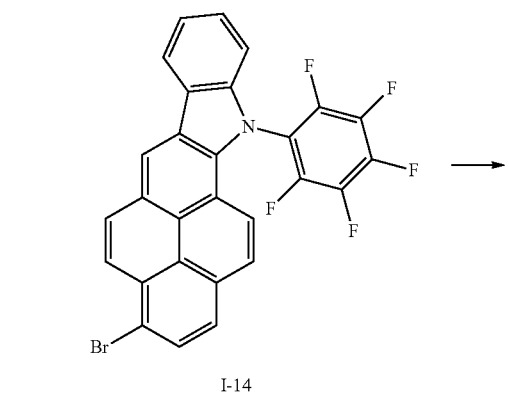

I-14

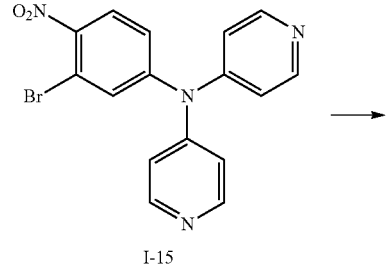

I-15

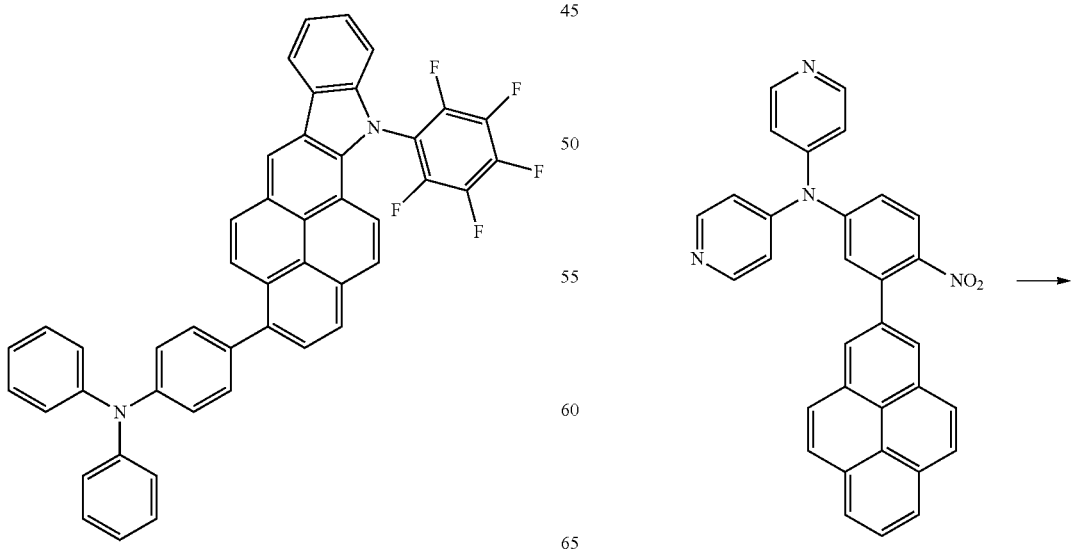

57

I-16

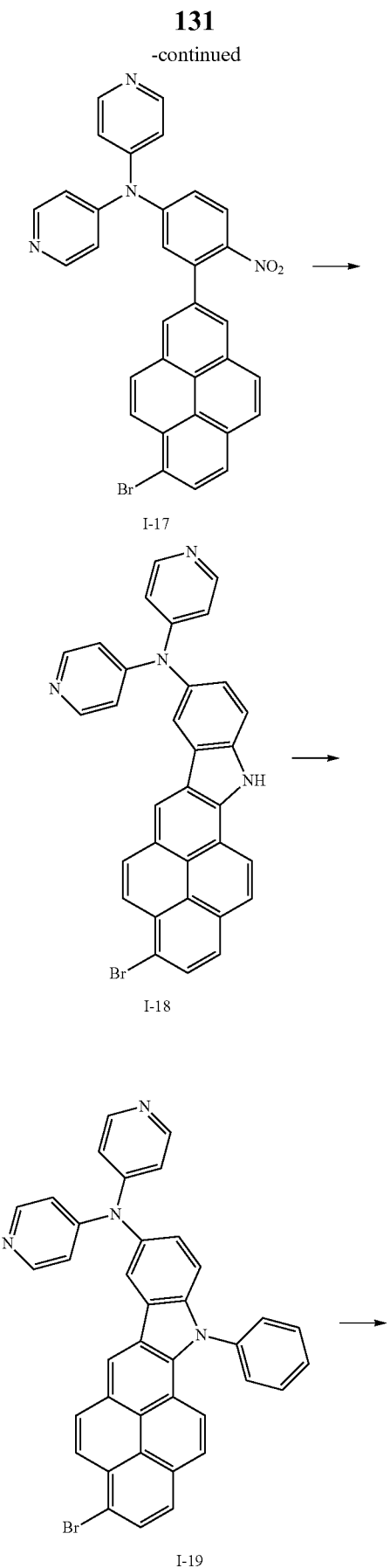

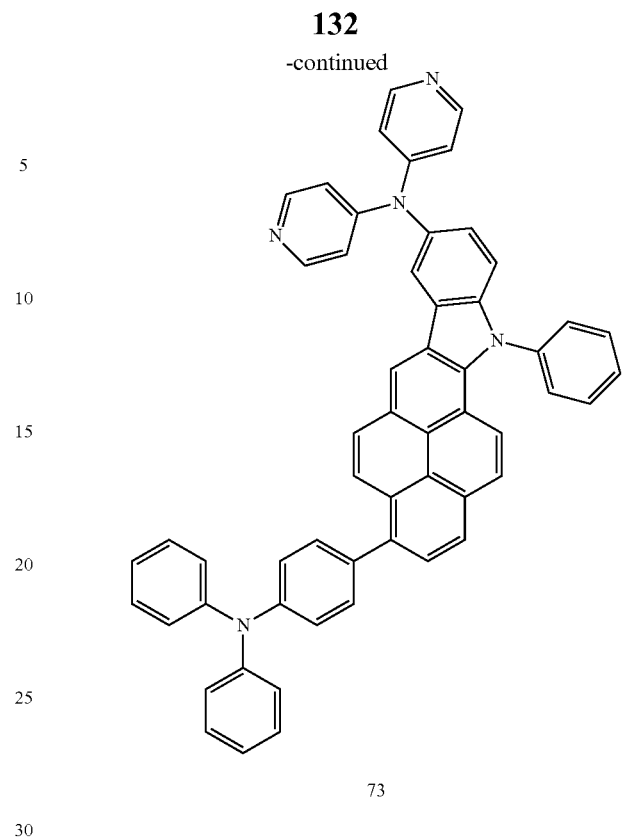

73

Synthesis of Intermediate I-15

5.62 g (20.0 mmol) of 2,4-dibromo-1-nitrobenzene, 1.71 g (10.0 mmol) of di-4-pyridylamine, 0.18 g (0.2 mmol) of $Pd_2(dba)_3$, 0.04 g (0.2 mmol) of $PtBu_3$, and 1.44 g (15.0 mmol) of NaOtBu were dissolved in 40 mL of toluene, and the mixture was stirred at 85° C. for 5 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 1.63 g of Intermediate I-15 (Yield: 44%) The produced compound was identified using LC-MS. $C_{16}H_{11}BrN_4O_2$ Calc.: 370.0; Measured [M+1] 371.0

Synthesis of Intermediate I-16

Intermediate I-16 was synthesized in the same manner as in the synthesis of Intermediate I-1 using Intermediate I-15. The produced compound was identified using LC-MS. $C_{32}H_{20}N_4O_2$ Calc.: 492.2; Measured [M+1] 493.3

Synthesis of Intermediate I-17

Intermediate I-17 was synthesized in the same manner as in the synthesis of Intermediate I-2 using Intermediate I-16. The produced compound was identified using LC-MS. $C_{32}H_{19}BrN_4O_2$ Calc.: 570.1; Measured [M+1] 571.1

Synthesis of Intermediate I-18

Intermediate I-18 was synthesized in the same manner as in the synthesis of Intermediate I-3 using Intermediate I-17. The produced compound was identified using LC-MS. $C_{32}H_{19}BrN_4$ Calc.: 538.1; Measured [M−1] 539.1

Synthesis of Intermediate I-19

Intermediate I-19 was synthesized in the same manner as in the synthesis of Intermediate I-4 using Intermediate I-18. The produced compound was identified using LC-MS. $C_{38}H_{23}BrN_4$ Calc.: 614.1; Measured [M+1] 615.1

Synthesis of Compound 73

Compound 73 was synthesized in the same manner as in the synthesis of Compound 2 using Intermediate I-5 and Intermediate I-19. The produced compound was identified using HR-MS. $C_{56}H_{37}N_5$ Calc.: 779.3049; Measured [M+1] 780.3042

$^1$H NMR (CDCl$_3$, 400 MHz) δ (ppm) 8.95-8.92 (d, 1H), 8.44-8.41 (d, 1H), 8.21-8.10 (m, 5H), 8.05-7.99 (m, 2H), 7.96-7.88 (m, 2H), 7.79-7.76 (m, 1H), 7.66-7.62 (m, 1H), 7.53-7.45 (m, 4H), 7.36-7.25 (m, 8H), 6.92-6.88 (m, 4H), 6.74-6.70 (m, 2H), 6.54-6.50 (m, 2H), 6.02-6.98 (m, 4H)

Synthesis Example 10

Synthesis of Compound 82

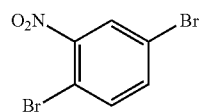

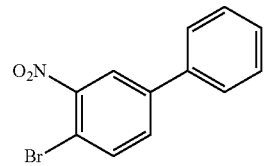
I-20

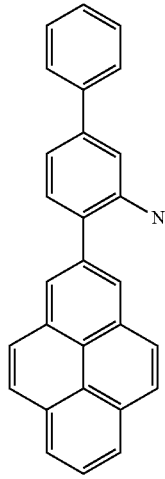
I-21

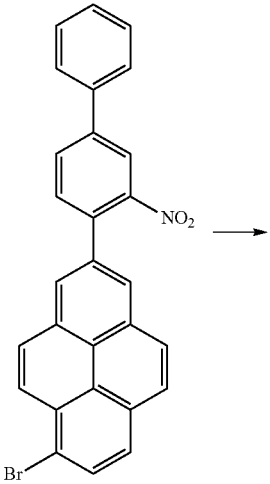
I-22
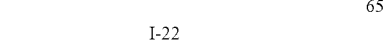

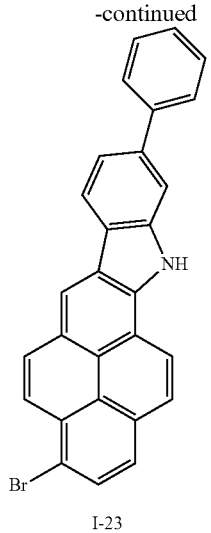
I-23

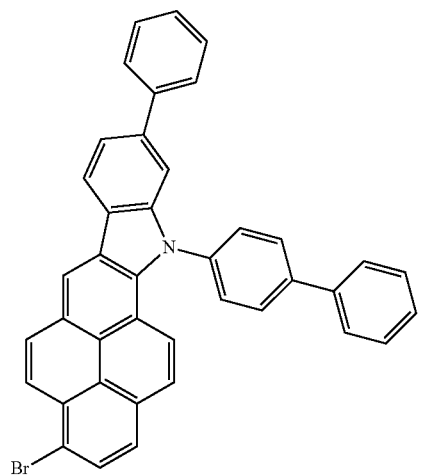
I-24

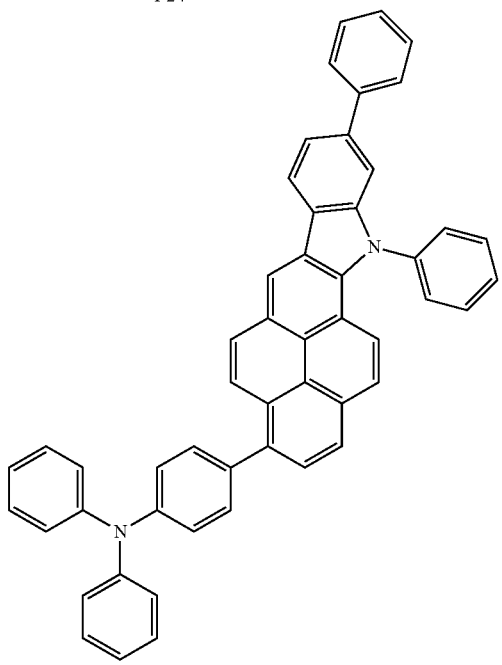
82

Synthesis of Intermediate I-20

5.62 g (20.0 mmol) of 1,4-dibromo-2-nitrobenzene, 1.22 g (10.0 mmol) of phenylboronic acid, 0.58 g (0.5 mmol) of PdPPh$_3$, and 4.14 g (30.0 mmol) of K$_2$CO$_3$ were dissolved in 40 mL of a THF/H$_2$O (2/1) solution, and the mixture was stirred at 80° C. for 5 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 1.33 g of Intermediate I-20 (Yield: 48%) The produced compound was identified using LC-MS. C$_{12}$H$_8$BrNO$_2$ Calc.: 277.0; Measured [M+1] 278.0

Synthesis of Intermediate I-21

Intermediate I-21 was synthesized in the same manner as in the synthesis of Intermediate I-16 using Intermediate I-20. The produced compound was identified using LC-MS. C$_{28}$H$_{17}$NO2 Calc.: 399.1; Measured [M+1] 400.1

Synthesis of Intermediate I-22

Intermediate I-22 was synthesized in the same manner as in the synthesis of Intermediate I-17 using Intermediate I-21. The produced compound was identified using LC-MS. C$_{28}$H$_{16}$BrNO$_2$ Calc.: 477.0; Measured [M+1] 478.0

Synthesis of Intermediate I-23

Intermediate I-23 was synthesized in the same manner as in the synthesis of Intermediate I-18 using Intermediate I-22. The produced compound was identified using LC-MS. C$_{28}$H$_{16}$BrN Calc.: 445.0; Measured [M+1] 446.0

Synthesis of Intermediate I-24

Intermediate I-24 was synthesized in the same manner as in the synthesis of Intermediate I-19 using Intermediate I-23 and 4-bromobiphenyl. The produced compound was identified using LC-MS. C$_{40}$H$_{24}$BrN Calc.: 597.1; Measured 598.1

Synthesis of Compound 82

Compound 82 was synthesized in the same manner as in the synthesis of Compound 73 using Intermediate I-5 and Intermediate I-24. The produced compound was identified using HR-MS. C$_{58}$H$_{35}$F$_3$N Calc.: 816.2752; Measured [M+1] 817.2746

$^1$H NMR (CDCl$_3$, 400 MHz) δ (ppm) 8.80-8.76 (d, 1H), 8.46-8.43 (d, 1H), 8.32-8.29 (dd, 1H), 8.6-8.06 (m, 2H), 8.02-7.89 (m, 4H), 7.76-7.52 (m, 4H), 7.50-7.46 (m, 2H), 7.43-7.28 (m, 12H), 6.84-6.63 (m, 3H), 6.55-6.52 (m, 2H), 6.45-6.43 (d, 1H), 6.12-6.09 (m, 2H)

Synthesis Example 11

Synthesis of Compound 87

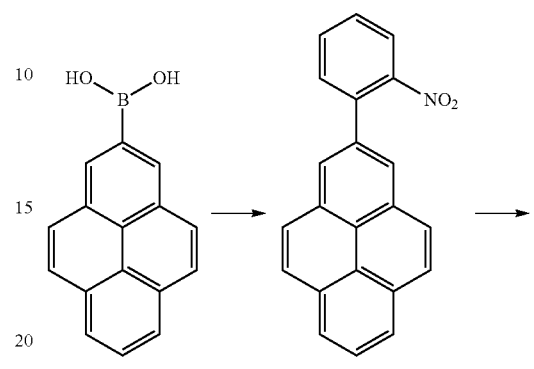

I-1

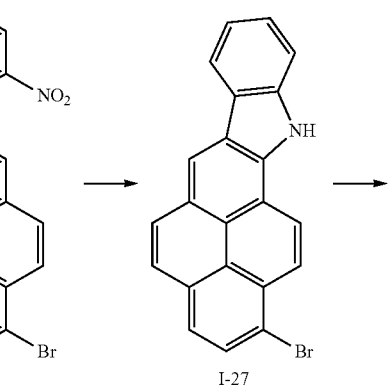

I-26          I-27

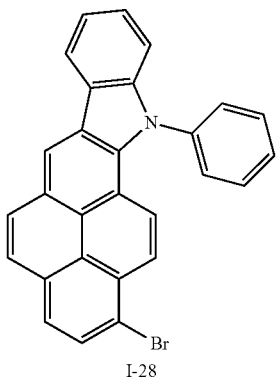

I-28

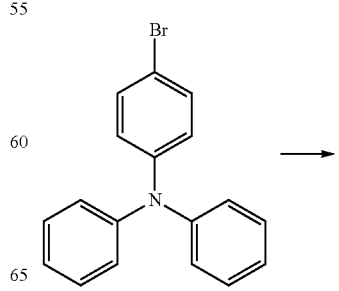

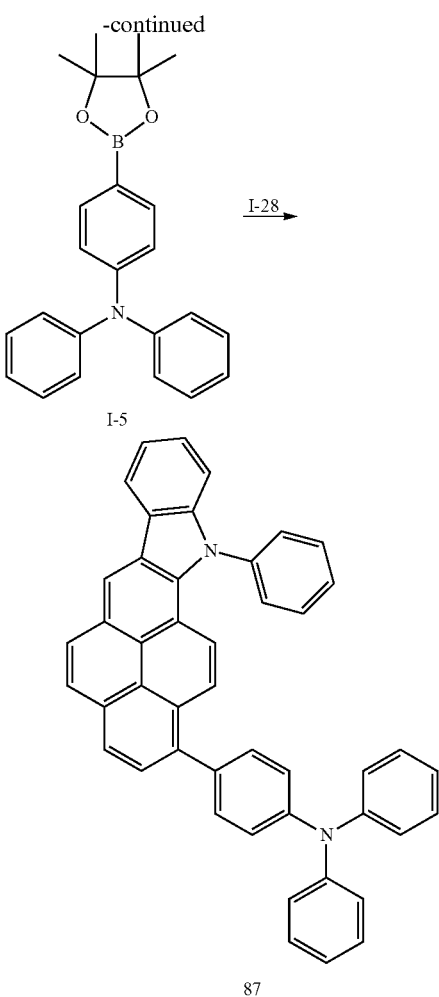

Synthesis of Intermediate I-1

4.93 g (20.0 mmol) of 2-pyrene boronic acid, 4.04 g (20.0 mmol) of 2-bromonitrobenzene, 1.15 g (1.0 mmol) of Pd(PPh$_3$)$_4$, and 8.29 g (60.0 mmol) of K$_2$CO$_3$ were dissolved in 60 mL of a THF/H$_2$O (2/1) solution, and the mixture was stirred at 70° C. for 5 hours. The mixture was cooled to room temperature, 40 mL of water was added thereto, and the mixture was subjected to extraction three times with 50 mL of ethyl ether. An organic layer was collected and dried using magnesium sulfate to evaporate the solvent. The residue was separately purified using silica gel column chromatography to obtain 5.95 g of Intermediate I-1 μl (Yield: 92%) The produced compound was identified using LC-MS. C$_{22}$H$_{13}$NO$_2$ Calc.: 323.1; Measured [M+1] 324.1

Synthesis of Intermediate I-26

4.85 g (15.0 mmol) of Intermediate I-1 was dissolved in 100 mL of dichloromethane, and 1.75 ml (15.0 mmol) of bromine (Br$_2$) was gradually added thereto at 0° C. C. The mixture was stirred at room temperature for 12 hours. 60 mL of water and 30 mL of a 20% sodium thiosulfate solution were added thereto. Then, the mixture was subjected to extraction three times with 80 mL of dichloromethane. An organic layer was collected and dried using magnesium sulfate to evaporate the solvent. The residue was separately purified using silica gel column chromatography and recrystallized using a dichloromethane/hexane solution to obtain 3.38 g of Intermediate I-26 (Yield: 56%) The produced compound was identified using LC-MS. C$_{22}$H$_{12}$BrNO$_2$ Calc.: 401.0; Measured [M+1] 402.0

Synthesis of Intermediate I-27

4.02 g (10.0 mmol) of Intermediate I-26 and 5.77 g (22 mmol) of triphenylphosphine (PPh$_3$) were dissolved in 30 mL of 1,2-dichlorobenzene, and the mixture was stirred at 170° C. for 12 hours. The mixture was cooled to room temperature, the solvent was removed in a vacuum, and the mixture was subjected to extraction three times with 50 mL of water and 50 mL of dichloromethane. An organic layer was collected and dried using magnesium sulfate to evaporate the solvent. The residue was separately purified using silica gel column chromatography to obtain 2.66 g of Intermediate I-27 (Yield: 72%) The produced compound was identified using LC-MS. C$_{72}$H$_{12}$BrN Calc.: 369.0; Measured [M+1] 370.1

Synthesis of Intermediate I-28

3.70 g (10.0 mmol) of Intermediate I-27, 3.06 g (15.0 mmol) of iodobenzene, 0.19 g (1.0 mmol) of CuI, 0.05 g (0.2 mmol) of 18-Crown-6, and 4.15 g (30.0 mmol) of K$_2$CO$_3$ were dissolved in 30 mL of 1,3-dimethyl-3,4,5,6-tetrahydro-3(1H)-pyrimidinone (DMPU), and the mixture was stirred at 170° C. for 12 hours. The mixture was cooled to room temperature and subjected to extraction three times with 50 mL of water and 50 mL of dichloromethane. An organic layer was collected and dried using magnesium sulfate to evaporate the solvent. The residue was separately purified using silica gel column chromatography to obtain 4.15 g of Intermediate I-28 (Yield: 93%) The produced compound was identified using LC-MS. C$_{28}$H$_{16}$BrN Calc.: 445.0; Measured [M+1] 446.0

Synthesis of Compound 87

2.23 g (5.0 mmol) of Intermediate I-28, 1.86 g (5.0 mmol) of Intermediate I-5, 0.29 g (0.25 mmol) of Pd(PPh$_3$)$_4$, and 2.07 g (15.0 mmol) of K$_2$CO$_3$ were dissolved in 30 mL of a THF/H$_2$O (2/1) solution, and the mixture was stirred at 70° C. for 5 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 2.11 g of Compound 87 (Yield: 69%). The produced compound was identified using HR-MS. C$_{46}$H$_{30}$N$_2$ Calc.: 610.2409; Measured [M+1] 611.2401

$^1$H NMR (CDCl$_3$, 400 MHz) δ (ppm) 9.25-9.21 (d, 1H), 8.92-8.85 (m, 1H), 8.66-8.62 (d, 1H), 8.26-8.24 (d, 1H), 8.17 (s, 1H), 8.07 (s, 2H), 8.01-7.98 (d, 1H), 7.76-7.74 (d, 4H), 7.62-7.56 (m, 6H), 7.39-7.23 (m, 10H), 7.12-7.00 (dt, 2H)

Synthesis Example 12

Synthesis of Compound 89

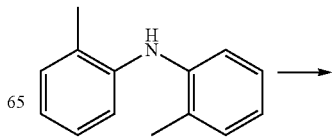

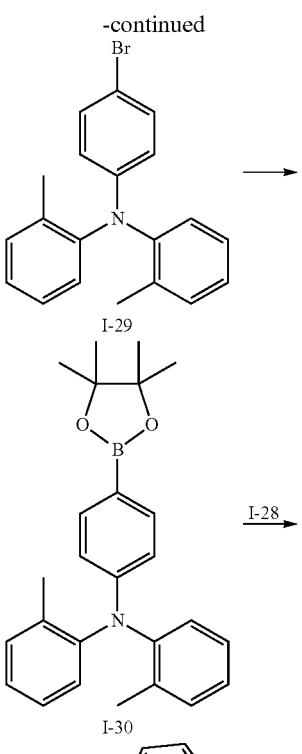

Synthesis of Intermediate I-29

1.97 g (10.0 mmol) of di-o-tolylamine, 4.24 g (15.0 mmol) of 4-bromoiodobenzene, 0.18 g (0.2 mmol) of Pd$_2$(dba)$_3$, 0.04 g (0.4 mmol) of PtBu$_3$, and 1.44 g (15.0 mmol) of KOtBu were dissolved in 40 mL of toluene, and the mixture was stirred at 85° C. for 4 hours. The mixture was cooled to room temperature and subjected to extraction three times with 30 mL of water and 30 mL of diethyl ether. An organic layer was collected and dried using magnesium sulfate to evaporate the solvent. The residue was separately purified using silica gel column chromatography to obtain 2.18 g of Intermediate I-29 (Yield: 62%) The produced compound was identified using LC-MS. C$_{20}$H$_{18}$BrN Calc.: 351.1; Measured [M+1] 352.1

Synthesis of Intermediate I-30

3.52 g (10.0 mmol) of Intermediate I-29, 2.54 g (10.0 mmol) of bis(pinacolato)diborone, 0.36 g (0.5 mmol) of PdCl$_2$(dppf)$_2$, and 2.94 g (30.0 mmol) of KOAc were dissolved in 40 mL of DMSO, and the mixture was stirred at 80° C. for 6 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 3.03 g of Intermediate I-30 (Yield: 76%) The produced compound was identified using LC-MS. C$_{26}$H$_{30}$BNO, Calc.: 399.2; Measured [M+1] 400.2

Synthesis of Compound 89

2.42 g of Compound 89 was synthesized with a yield of 76% in the same manner as in the synthesis of Compound 87 using Intermediate I-28 and Intermediate I-30. The produced compound was identified using LC-MS and NMR. C$_{48}$H$_{34}$N$_2$ Calc.: 638.3; Measured [M+1] 639.3

$^1$H NMR (CDCl$_3$, 400 MHz) δ (ppm) 8.96-8.94 (d, 1H), 8.23-8.17 (m, 2H), 8.09-8.07 (d, 1H), 8.04 (s, 1H), 7.94-7.88 (m, 3H), 7.51-7.47 (m, 4H), 7.37-7.31 (m, 4H), 7.28-7.22 (m, 4H), 7.17-7.13 (dt, 2H), 6.90-6.86 (dt, 2H), 6.78-6.73 (m, 4H), 2.02 (s, 6H)

Synthesis Example 13

Synthesis of Compound 95

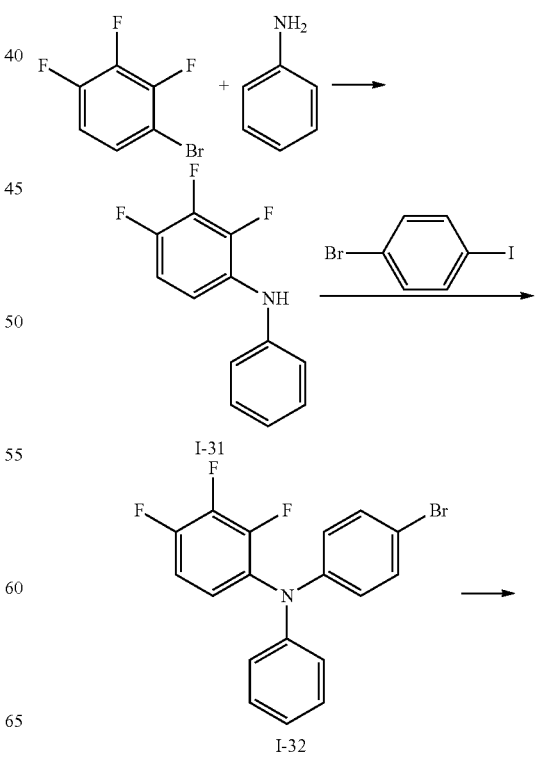

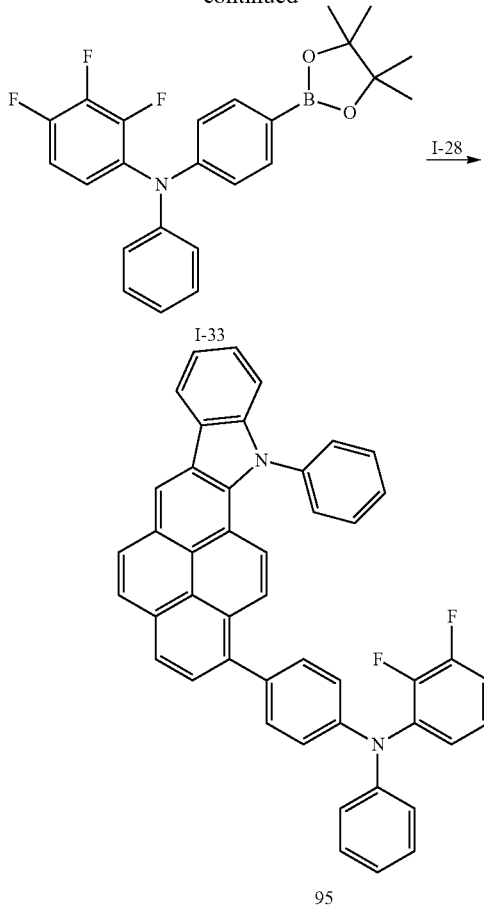

Synthesis of Intermediate I-33

3.78 g (10.0 mmol) of Intermediate I-32, 2.54 g (10.0 mmol) of bis(pinacolato)diborone, 0.36 g (0.5 mmol) of $PdCl_2(dppf)_2$, and 2.94 g (30.0 mmol) of KOAc were dissolved in 40 mL of DMSO, and the mixture was stirred at 80° C. for 6 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 3.40 g of Intermediate I-33 (Yield: 80%) The produced compound was identified using LC-MS. $C_{24}H_{23}BF_3NO_2$ Calc.: 425.2; Measured [M+1] 426.2

Synthesis of Compound 95

2.39 g of Compound 95 was synthesized with a yield of 72% in the same manner as in the synthesis of Compound 87 using Intermediate I-28 and Intermediate I-33. The produced compound was identified using LC-MS and NMR. $C_{46}H_{27}F_3N_2$ Calc.: 664.2; Measured [M+1] 665.2

$^1$H NMR (CDCl$_3$, 400 MHz) δ (ppm) 9.25-9.22 (d, 1H), 8.92-8.89 (d, 1H), 8.43-8.40 (d, 1H), 8.33-8.30 (d, 1H), 8.23-8.20 (d, 1H), 8.10 (s, 1H), 7.99 (t, 2H), 7.74-7.72 (m, 4H), 7.62-7.53 (m, 6H), 7.34 (dt, 2H), 7.18-7.15 (d, 4H), 7.12-6.91 (m, 31-1)

Synthesis Example 14

Synthesis of Compound 105

Synthesis of Intermediate I-31

4.22 g (20.0 mmol) of 1-bromo-2,3,4-trifluorobenzene, 2.79 g (30.0 mmol) of aniline, 0.37 g (0.4 mmol) of Pd$_2$(dba)$_3$, 0.08 g (0.4 mmol) of PtBu$_3$, and 2.88 g (30.0 mmol) of KOtBu were dissolved in 60 mL of toluene, and the mixture was stirred at 85° C. for 4 hours. The mixture was cooled to room temperature and subjected to extraction three times with 50 mL of water and 50 mL of diethyl ether. An organic layer was collected and dried using magnesium sulfate to evaporate the solvent. The residue was separately purified using silica gel column chromatography to obtain 3.93 g of Intermediate I-31 (Yield: 88%) The produced compound was identified using LC-MS. $C_{12}H_8F_3N$ Calc.: 223.1; Measured [M+1] 224.1

Synthesis of Intermediate I-32

2.23 g (15.0 mmol) of Intermediate I-31, 4.23 g (15.0 mmol) of 4-bromoiodobenzene, 0.18 g (0.2 mmol) of Pd$_2$(dba)$_3$, 0.04 g (0.4 mmol) of PtBu$_3$, and 1.44 g (15.0 mmol) of KOtBu were dissolved in 40 mL of toluene, and the mixture was stirred at 85° C. for 4 hours. The mixture was cooled to room temperature and subjected to extraction three times with 30 mL of water and 30 mL of diethyl ether. An organic layer was collected and dried using magnesium sulfate to evaporate the solvent. The residue was separately purified using silica gel column chromatography to obtain 2.38 g of Intermediate I-32 (Yield: 63%) The produced compound was identified using LC-MS. $C_{18}H_{11}BrF_3N$ Calc.: 377.0; Measured [M+1] 378.0

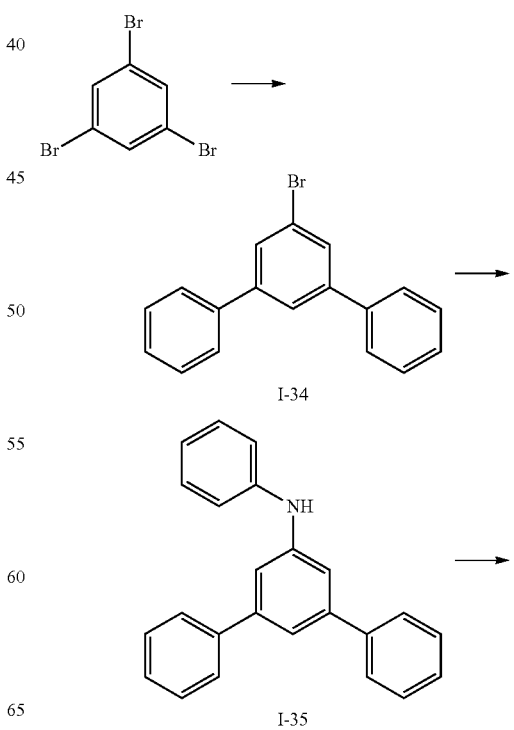

-continued

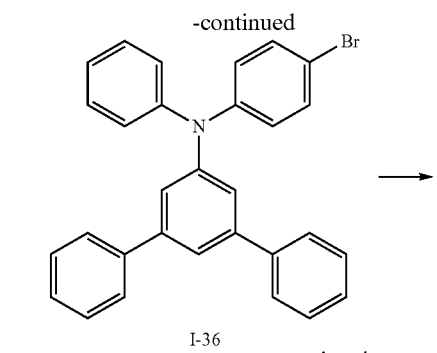

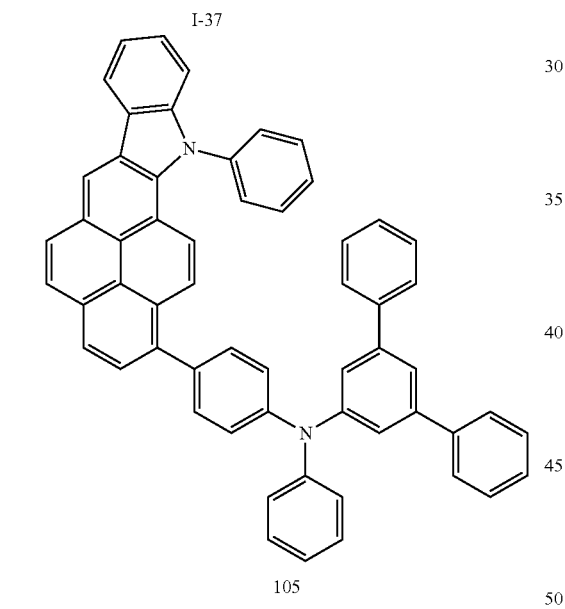

Synthesis of Intermediate I-34

6.3 g (20.0 mmol) of 1,3,5-tribromobenzene, 4.88 g (40.0 mmol) of 1-phenyl boronic acid, 2.31 g (2.0 mmol) of Pd(PPh$_3$)$_4$, and 16.6 g (120.0 mmol) of K$_2$CO$_3$ were dissolved in 120 mL of a THF/H$_2$O (2/1) solution, and the mixture was stirred at 70° C. for 5 hours. The mixture was cooled to room temperature and subjected to extraction three times with 120 mL of water and 100 mL of diethyl ether. An organic layer was collected and dried using magnesium sulfate to evaporate the solvent. The residue was separately purified using silica gel column chromatography to obtain 3.83 g of Intermediate I-34 (Yield: 62%) The produced compound was identified using LC-MS. C$_{18}$H$_{13}$Br Calc.: 308.0; Measured [M+1] 309.0

Synthesis of Intermediate I-35

2.73 g of Intermediate I-35 was synthesized with a yield of 85% in the same manner as in the synthesis of Intermediate I-31, using Intermediate 1-34 and aniline. The produced compound was identified using LC-MS. C$_{24}$H$_{19}$N Calc.: 321.2; Measured [M+1] 322.2

Synthesis of Intermediate I-36

3.14 g of Intermediate I-36 was synthesized with a yield of 66% in the same manner as in the synthesis of Intermediate I-32, using Intermediate 1-35. The produced compound was identified using LC-MS. C$_{30}$H$_{22}$BrN Calc.: 475.1; Measured [M+1] 476.1

Synthesis of Intermediate I-37

4.08 g of Intermediate I-37 was synthesized with a yield of 78% in the same manner as in the synthesis of Intermediate I-33, using Intermediate 1-36. The produced compound was identified using LC-MS. C$_{36}$H$_{34}$BNO$_2$ Calc.: 523.3; Measured [M+1] 524.3

Synthesis of Compound 105

2.86 g of Compound 21 was synthesized with a yield of 75% in the same manner as in the synthesis of Compound 87 using Intermediate I-28 and Intermediate I-37. The produced compound was identified using LC-MS and NMR. C$_{58}$H$_{38}$N$_2$ Calc.: 762.3035; Measured [M+1] 763.3035

$^1$H NMR (CDCl$_3$, 400 MHz) δ (ppm) 9.16-9.14 (d, 1H), 8.73-8.67 (m, 2H), 8.46-8.44 (d, 1H), 8.24 (s, 1H), 7.94-7.90 (m, 4H), 7.62-7.58 (m, 6H), 7.54-7.53 (d, 8H), 7.45-7.39 (m, 10H), 7.24-7.20 (m, 1H), 7.15-7.12 (m, 2H), 7.01-6.99 (d, 2H)

Synthesis Example 15

Synthesis of Compound 108

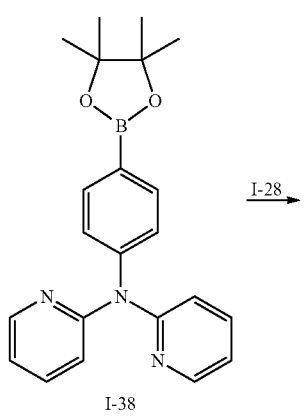

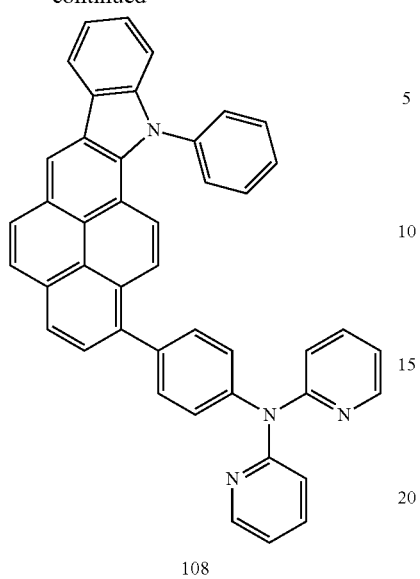

108

2.18 g of Compound 108 was synthesized with a yield of 71% in the same manner as in the synthesis of Compound 87 using Intermediate I-28 and Intermediate I-38. The produced compound was identified using LC-MS. $C_{44}H_{28}N_4$ Calc.: 612.2314; Measured [M+1] 613.2405

$^1$H NMR (CDCl$_3$, 400 MHz) δ (ppm) 9.23-9.21 (d, 1H), 8.63-8.49 (m, 4H), 8.29-8.27 (d, 1H), 8.14 (s, 1H), 7.94-7.88 (m, 3H), 7.78-7.68 (m, 8H), 7.47-7.40 (m, 6H), 7.11-7.08 (m, 2H), 7.02-6.99 (m, 2H)

Synthesis Example 16

Synthesis of Compound 124

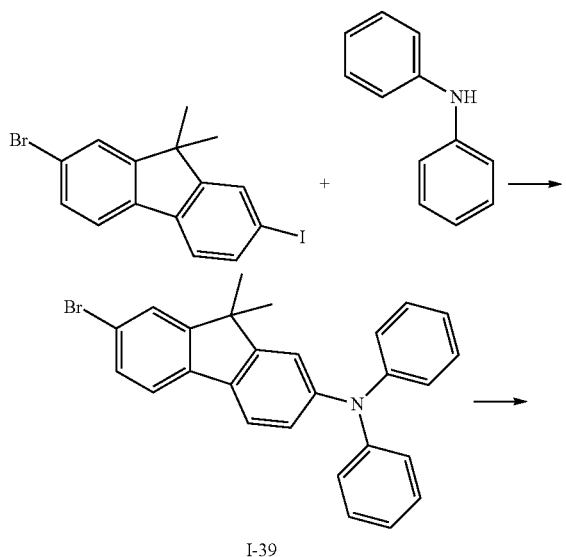

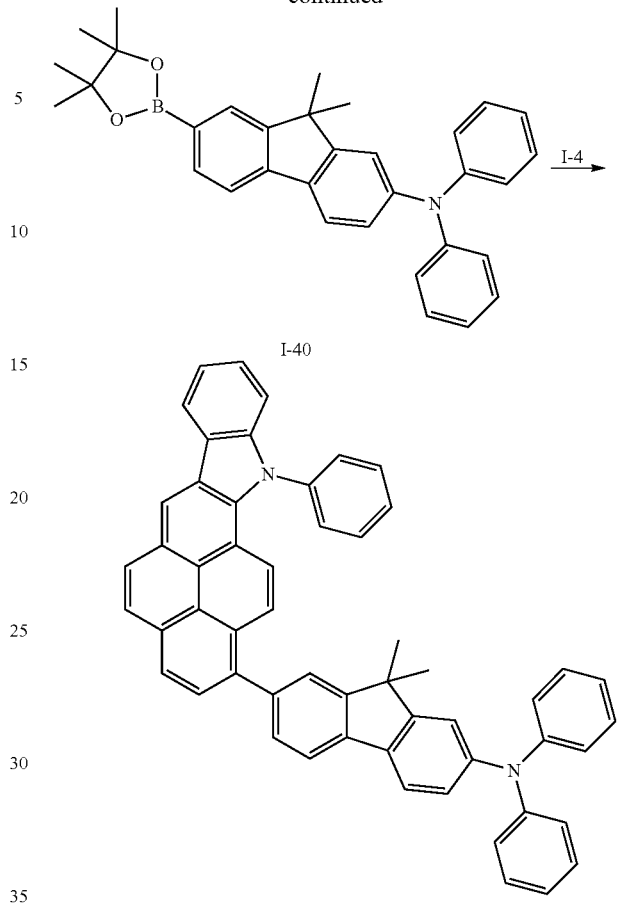

Synthesis of Intermediate I-39

3.04 g of Intermediate I-39 was synthesized with a yield of 69% in the same manner as in the synthesis of Intermediate I-36 using 2-bromo-7-iodo-9,9-dimethyl fluorene and diphenylamine. The produced compound was identified using LC-MS. $C_{27}H_{22}BrN$ Calc.: 439.1; Measured [M+1] 440.1

Synthesis of Intermediate I-40

3.99 g of Intermediate I-40 was synthesized with a yield of 82% in the same manner as in the synthesis of Intermediate I-37, using Intermediate I-39. The produced compound was identified using LC-MS and NMR. $C_{33}H_{34}BNO_2$ Calc.: 487.3; Measured [M+1] 488.3

Synthesis of Compound 124

2.65 g of Compound 124 was synthesized with a yield of 73% in the same manner as in the synthesis of Compound 87 using Intermediate I-28 and Intermediate I-40. The produced compound was identified using LC-MS. $C_{55}H_{38}N_2$ Calc.: 726.3035; Measured [M+1] 727.3035

1H NMR (CDCl$_3$, 400 MHz) δ (ppm) 9.17-9.15 (d, 1H), 8.73-8.67 (m, 2H), 8.57-8.54 (m, 2H), 8.34-8.32 (d, 1H), 8.28-8.26 (d, 1H), 8.03-8.01 (d, 1H), 7.85-7.83 (d, 1H), 7.69-7.67 (m, 4H), 7.55-7.49 (m, 8H), 7.35-7.33 (d, 1H), 7.30-7.29

(d, 1H), 7.24 (d, 1H), 7.13-7.11 (dd, 1H), 7.04-7.00 (dt, 2H), 6.94-6.92 (dd, 1H), 6.88-6.86 (dd, 4H), 1.85 (s, 6H)

Synthesis Example 17

Synthesis of Compound 141

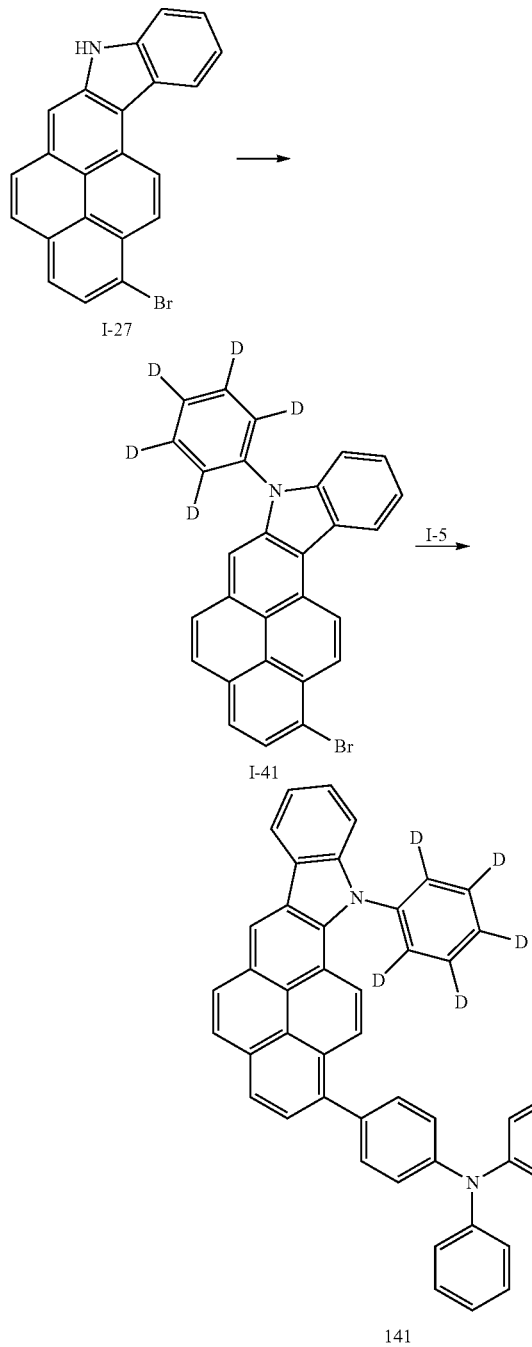

Synthesis of Intermediate I-41

3.48 g of Intermediate I-41 was synthesized with a yield of 77% in the same manner as in the synthesis of Intermediate I-37, using Intermediate I-27 and chlorobenzene-d₅. The pro-duced compound was identified using LC-MS and NMR. $C_{28}H_{11}D_5BrN$ Calc.: 450.1; Measured: [M+1] 451.1

Synthesis of Compound 141

2.52 g of Compound 141 was synthesized with a yield of 82% in the same manner as in the synthesis of Compound 87 using Intermediate I-5 and Intermediate I-41. The produced compound was identified using LC-MS and NMR. $C_{46}H_{25}D_5N_2$ Calc.: 615.2723; Measured [M+1] 616.2723

$^1$H NMR (CDCl₃, 400 MHz) δ (ppm) 9.26-9.24 (d, 1H), 8.63-8.57 (m, 2H), 8.49-8.47 (d, 1H), 8.44 (s, 1H), 8.14-8.10 (t, 3H), 7.65-7.59 (m, 9H), 7.34-7.32 (m, 2H), 7.25-7.21 (m, 2H), 7.10-7.08 (dd, 4H)

Synthesis Example 18

Synthesis of Compound 146

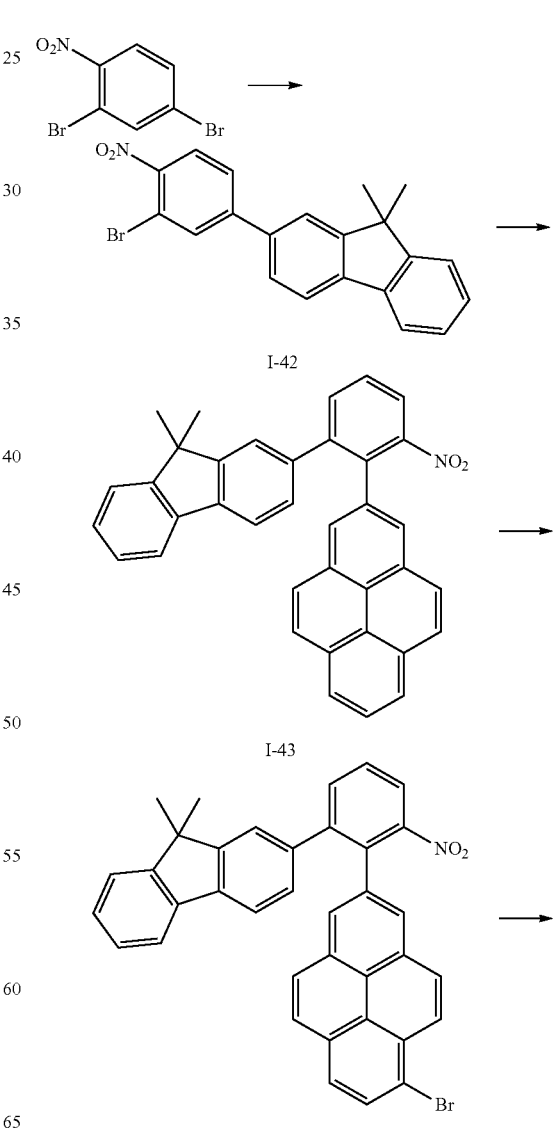

149

-continued

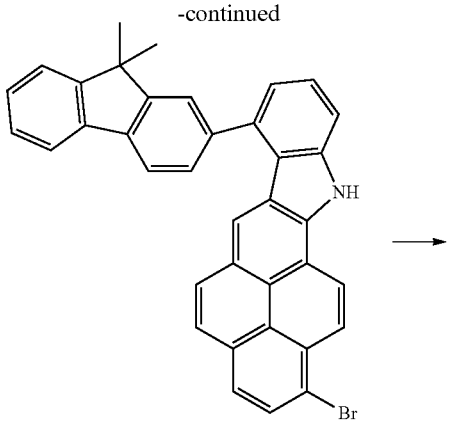

I-45

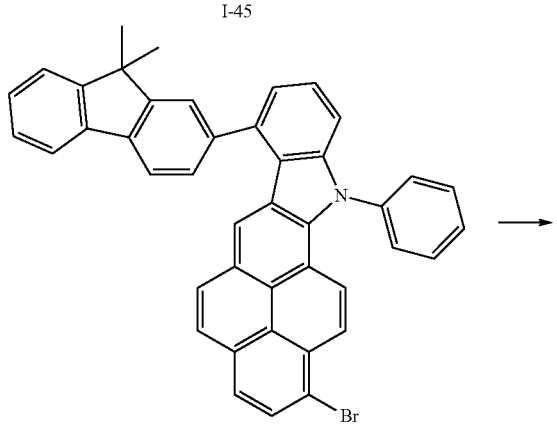

I-46

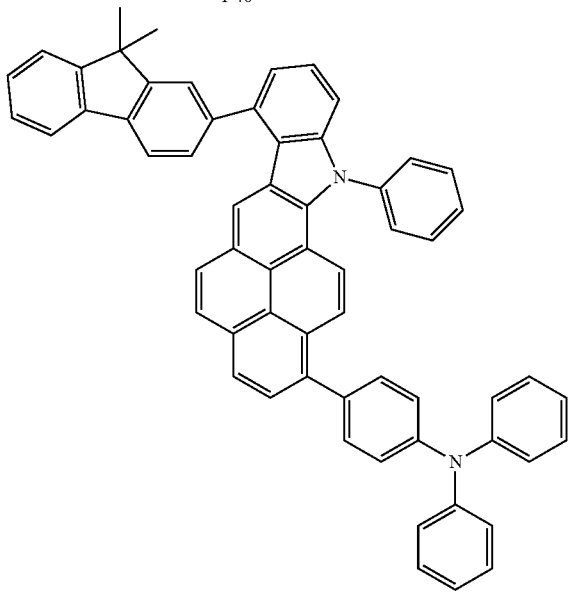

146

Synthesis of Intermediate I-42

5.62 g (20.0 mmol) of 2,4-dibromo-1-nitrobenzene, 4.52 g (19.0 mmol) of 9,9-dimethylfluorene-2-boronic acid, 1.15 g (1.0 mmol) of Pd(PPh$_3$)$_4$, and 8.29 g (60.0 mmol) of K$_2$CO$_3$ were dissolved in 80 mL of a THF/H$_2$O (2/1) solution, and the mixture was stirred at 70° C. for 5 hours. The mixture was cooled to room temperature and subjected to extraction three times with 60 mL of water and 60 mL of diethyl ether. An organic layer was collected and dried using magnesium sulfate to evaporate the solvent. The residue was separately purified using silica gel column chromatography to obtain 4.57 g of Intermediate I-42 (Yield: 58%) The produced compound was identified using LC-MS. C$_{21}$H$_{16}$BrNO$_2$ Calc.: 393.0; Measured [M+1] 394.0

Synthesis of Intermediate I-43

4.28 g of Intermediate I-43 as synthesized with a yield of 83% in the same manner as in the synthesis of Intermediate I-1, using Intermediate I-42 and pyrene boronic acid. The produced compound was identified using LC-MS. C$_{37}$H$_{25}$NO$_2$ Calc.: 515.2; Measured [M+1] 516.2

Synthesis of Intermediate I-44

2.79 g of Intermediate I-44 was synthesized with a yield of 47% in the same manner as in the synthesis of Intermediate I-26, using Intermediate 1-43. The produced compound was identified using LC-MS. C$_{37}$H$_{24}$BrNO$_2$ Calc.: 593.1; Measured [M+1] 1594.1

Synthesis of Intermediate I-45

3.21 g of Intermediate I-45 was synthesized with a yield of 57% in the same manner as in the synthesis of Intermediate I-27, using Intermediate I-44. The produced compound was identified using LC-MS. C$_{37}$H$_{74}$BrN Calc.: 561.1; Measured [M+1] 562.1

Synthesis of Intermediate I-46

4.98 g of Intermediate I-46 was synthesized with a yield of 78% in the same manner as in the synthesis of Intermediate I-28, using Intermediate 1-45. The produced compound was identified using LC-MS. C$_{43}$H$_{28}$BrN Calc.: 637.1; Measured [M+1] 628.1

Synthesis of Compound 146

2.93 g of Compound 146 was synthesized with a yield of 73% in the same manner as in the synthesis of Compound 87 using Intermediate I-5 and Intermediate I-46. The produced compound was identified using LC-MS and NMR. C$_{61}$H$_{42}$N$_2$ Calc.: 802.3348; Measured [M−1] 803.3348

$^1$H NMR (CDCl$_1$, 400 MHz) δ (ppm) 9.11-9.09 (d, 1H), 8.60-8.57 (d, 1H), 8.49-8.48 (d, 1H), 8.29 (s, 1H), 8.23-8.18 (m, 4H), 7.99-7.97 (dd, 1H), 7.77 (dd, 1H), 7.61-7.58 (m, 5H), 7.46-7.39 (m, 7H), 7.34-7.31 (dt, 1H), 7.22-7.13 (m, 5H), 7.04-7.00 (m, 2H), 6.95-6.91 (m, 2H), 6.80-6.78 (m, 4H), 1.86 (s, 6H)

Synthesis Example 19

Synthesis of Compound 158

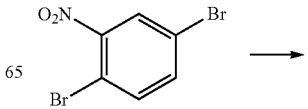

-continued

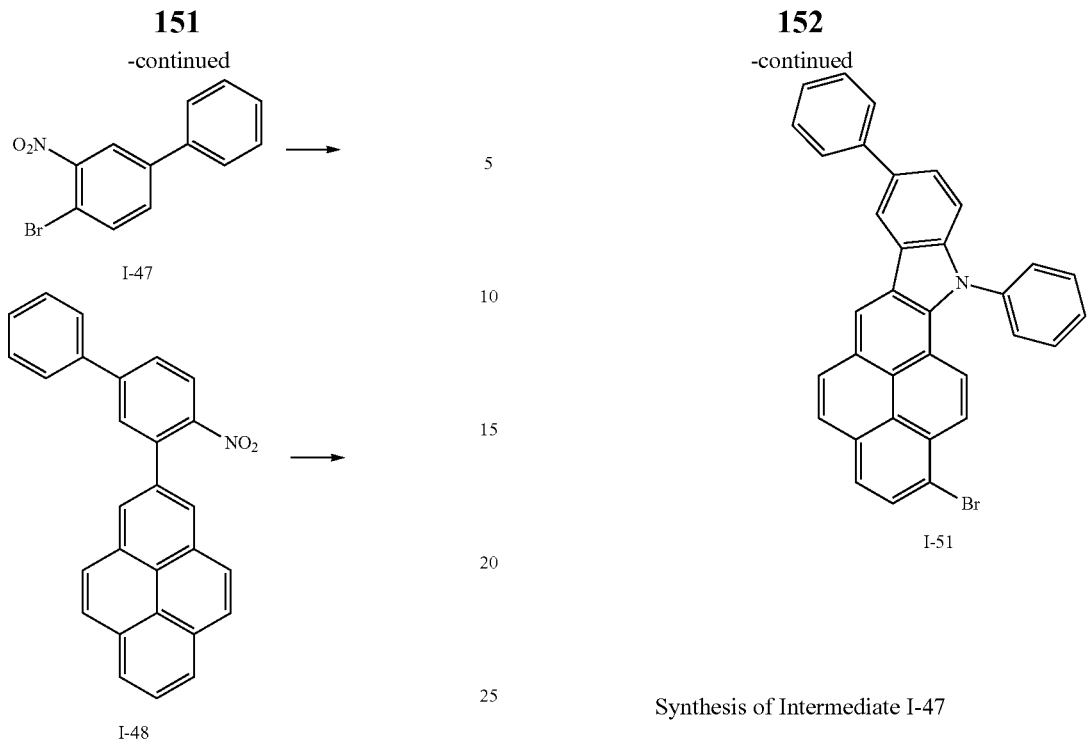

-continued

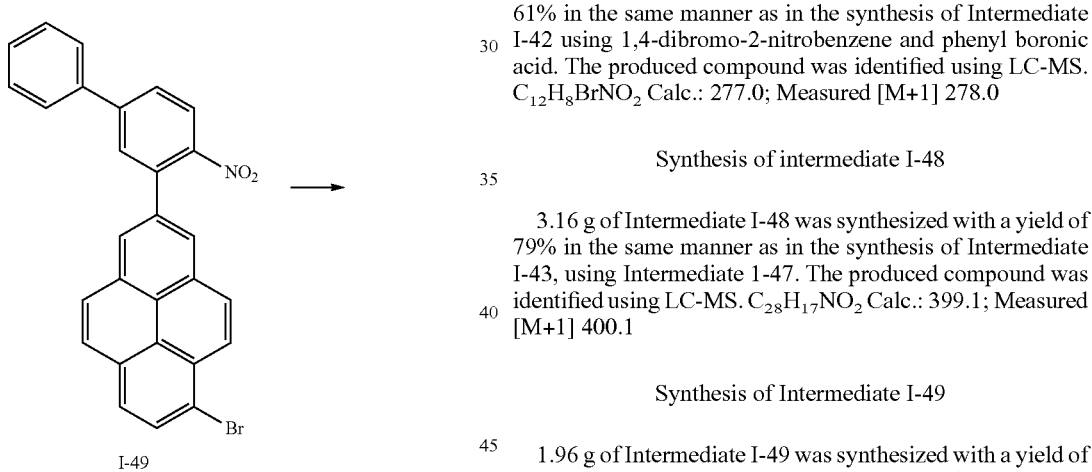

I-51

Synthesis of Intermediate I-47

3.39 g of Intermediate I-47 was synthesized with a yield of 61% in the same manner as in the synthesis of Intermediate I-42 using 1,4-dibromo-2-nitrobenzene and phenyl boronic acid. The produced compound was identified using LC-MS. $C_{12}H_8BrNO_2$ Calc.: 277.0; Measured [M+1] 278.0

Synthesis of intermediate I-48

3.16 g of Intermediate I-48 was synthesized with a yield of 79% in the same manner as in the synthesis of Intermediate I-43, using Intermediate I-47. The produced compound was identified using LC-MS. $C_{28}H_{17}NO_2$ Calc.: 399.1; Measured [M+1] 400.1

Synthesis of Intermediate I-49

1.96 g of Intermediate I-49 was synthesized with a yield of 41% in the same manner as in the synthesis of Intermediate I-44, using Intermediate I-48. The produced compound was identified using LC-MS. $C_{28}H_{16}BrNO_2$ Calc.: 477.0; Measured [M+1] 478.0

Synthesis of Intermediate I-50

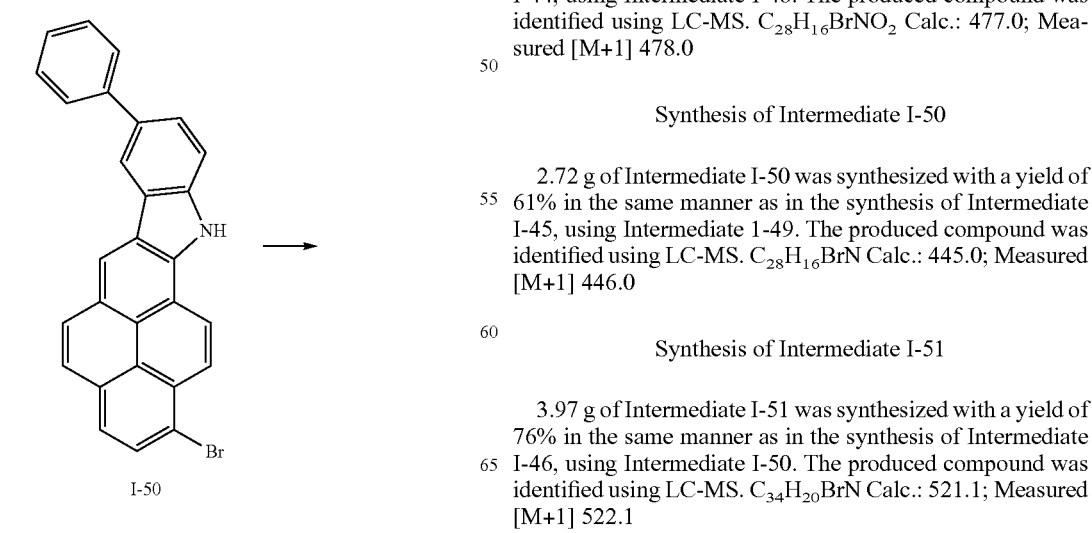

2.72 g of Intermediate I-50 was synthesized with a yield of 61% in the same manner as in the synthesis of Intermediate I-45, using Intermediate I-49. The produced compound was identified using LC-MS. $C_{28}H_{16}BrN$ Calc.: 445.0; Measured [M+1] 446.0

Synthesis of Intermediate I-51

3.97 g of Intermediate I-51 was synthesized with a yield of 76% in the same manner as in the synthesis of Intermediate I-46, using Intermediate I-50. The produced compound was identified using LC-MS. $C_{34}H_{20}BrN$ Calc.: 521.1; Measured [M+1] 522.1

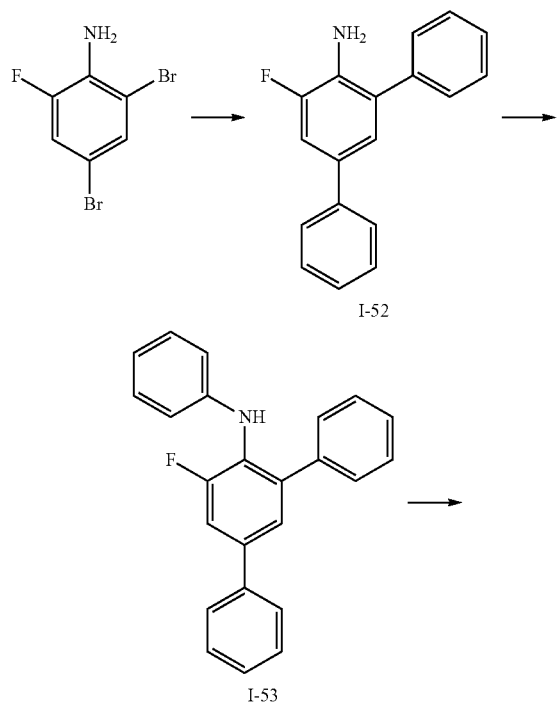

I-52

I-53

I-54

I-55

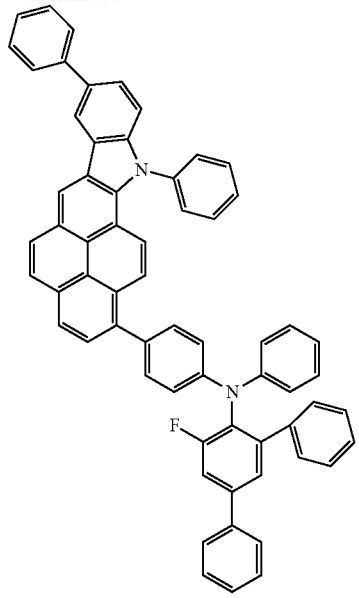

158

Synthesis of Intermediate I-52

5.38 g (20.0 mmol) of 2,4-dibromo-6-fluoro-phenylamine, 5.36 g (44.0 mmol) of phenyl boronic acid, 1.15 g (1.0 mmol) of Pd(PPh$_3$)$_4$, and 8.29 g (60.0 mmol) of K$_2$CO$_3$ were dissolved in 80 mL of a THF/H$_2$O (2/1) solution, and the mixture was stirred at 70° C. for 5 hours. The mixture was cooled to room temperature and subjected to extraction three times with 60 mL of water and 60 mL of diethyl ether. An organic layer was collected and dried using magnesium sulfate to evaporate the solvent. The residue was separately purified using silica gel column chromatography to obtain 4.11 g of Intermediate I-52 (Yield: 78%) The produced compound was identified using LC-MS. C$_{18}$H$_{14}$FN Calc.: 263.1; Measured [M+1] 264.1

Synthesis of Intermediate I-53

2.44 g of Intermediate I-53 was synthesized with a yield of 72% in the same manner as in the synthesis of Intermediate I-31, using Intermediate I-52. The produced compound was identified using LC-MS. C$_{24}$H$_{18}$FN Calc.: 339.1; Measured [M+1] 340.1

Synthesis of Intermediate I-54

3.31 g of Intermediate I-54 was synthesized with a yield of 67% in the same manner as in the synthesis of Intermediate I-32, using Intermediate I-53. The produced compound was identified using LC-MS. C$_{30}$H$_{21}$BrFN Calc.: 493.1; Measured [M+1] 494.1

Synthesis of Intermediate I-55

4.28 g of Intermediate I-55 was synthesized with a yield of 79% in the same manner as in the synthesis of Intermediate I-32, using Intermediate I-54. The produced compound was identified using LC-MS. C$_{36}$H$_{33}$BFNO$_2$ Calc.: 541.3; Measured [M+1] 542.3

Synthesis of Compound 158

3.26 g of Compound 158 was synthesized with a yield of 76% in the same manner as in the synthesis of Compound 87 using Intermediate I-51 and Intermediate I-55. The produced compound was identified using LC-MS and NMR. $C_{64}H_{41}FN_2$ Calc.: 856.3254; Measured [M+1] 847.3254

$^1$H NMR (CDCl$_3$, 400 MHz) δ (ppm) 9.06-9.04 (d, 1H), 8.50-8.48 (m, 2H), 8.39-8.37 (d, 1H), 8.33-8.27 (dd, 2H), 8.19-8.10 (m, 6H), 7.92-7.85 (m, 4H), 7.71-7.70 (dd, 2H), 7.61-7.50 (m, 9H), 7.46-7.36 (m, 9H), 7.14-7.10 (dt, 1H), 7.09-7.05 (m, 2H), 6.95-6.93 (dd, 2H)

Example 1

An anode was prepared by cutting a Corning 15 Ω/cm² (1200 Å) ITO glass substrate to a size of 50 mm×50 mm×0.7 mm, ultrasonically cleaning the glass substrate using isopropyl alcohol and pure water for five minutes each, and then irradiating UV light for 30 minutes and exposing to ozone to clean. Then, the glass substrate was disposed in a vacuum deposition apparatus.

Then, 2-TNATA, which is a known material for forming a HIL, was vacuum deposited on the glass substrate to form a HIL having a thickness of 600 Å, and then 4,4'-bis[N-(1-naphthyl)-N-phenylamino]biphenyl (NPB), as a hole transporting compound, was vacuum deposited on the HIL to form a HTL having a thickness of 300 Å.

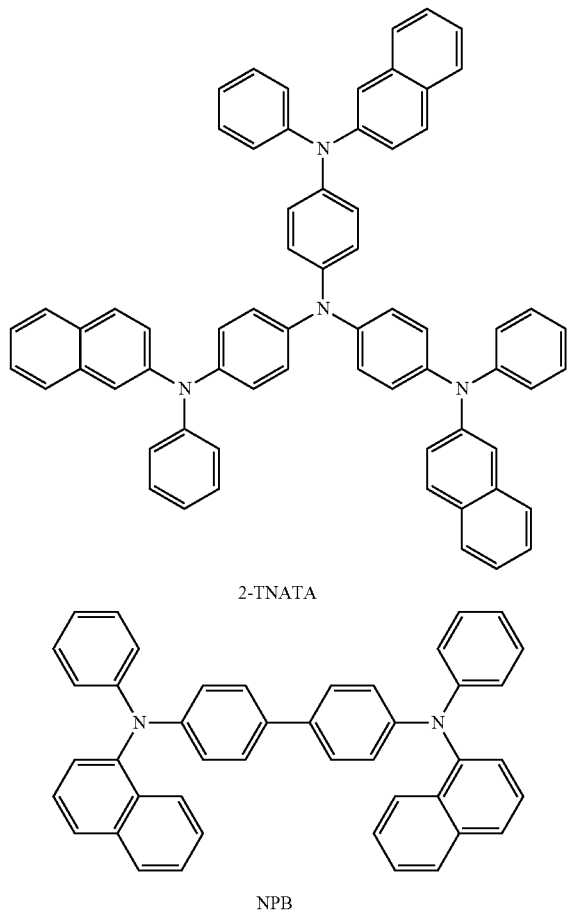

2-TNATA

NPB

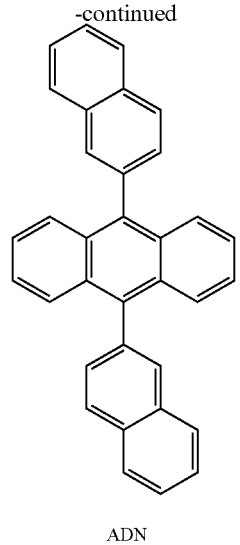

ADN

Then, 9,10-di-naphthalene-2-yl-anthracene (ADN), as a known blue fluorescent host, and Compound 2, as a known blue fluorescent dopant, were deposited simultaneously with a weight ratio of 98:2 on the HTL to form an EML having a thickness of 300 Å.

Then, Alq3 was deposited on the EML to form an ETL having a thickness of 300 Å, and then LiF, which is a halogenated alkali metal, was deposited on the ETL to form an EIL having a thickness of 10 Å. Then, Al was vacuum deposited on the EIL to form a cathode having a thickness of 3000 Å, thereby forming an LiF/Al electrode. As a result, an organic light-emitting device was manufactured.

The organic light-emitting device had a driving voltage of 6.37 V at a current density of 50 mA/cm², a high luminosity of 2739 cd/m², a luminescent efficiency of 5.47 cd/A, and a half-lifespan of 270 hours at 100 mA/cm².

Example 2

An organic light-emitting device was manufactured in the same manner as in Example 1, except that Compound 11 was used instead of Compound 2 to form the EML.

The organic light-emitting device had a driving voltage of 6.49 V at a current density of 50 mA/cm², a high luminosity of 2981 cd/m², a luminescent efficiency of 5.96 cd/A, and a 18 half-lifespan of 235 hours at 100 mA/cm².

Example 3

An organic light-emitting device was manufactured in the same manner as in Example 1, except that Compound 24 was used instead of Compound 2 to form the EML.

The organic light-emitting device had a driving voltage of 6.23 V at a current density of 50 mA/cm², a high luminosity of 2280 cd/m², a luminescent efficiency of 4.56 cd/A, and a half-lifespan of 208 hours at 100 mA/cm².

Example 4

An organic light-emitting device was manufactured in the same manner as in Example 1, except that Compound 34 was used instead of Compound 2 to form the EML.

The organic light-emitting device had a driving voltage of 6.42 V at a current density of 50 mA/cm², a high luminosity of 2695 cd/m², a luminescent efficiency of 5.39 cd/A, and a half-lifespan of 212 hours at 100 mA/cm².

Example 5

An organic light-emitting device was manufactured in the same manner as in Example 1, except that Compound 45 was used instead of Compound 2 to form the EML.

The organic light-emitting device had a driving voltage of 6.38 V at a current density of 50 mA/cm$^2$, a high luminosity of 2577 cd/m$^2$, a luminescent efficiency of 5.15 cd/A, and a half-lifespan of 225 hours at 100 mA/cm$^2$.

Example 6

An organic light-emitting device was manufactured in the same manner as in Example 1, except that Compound 48 was used instead of Compound 2 to form the EML.

The organic light-emitting device had a driving voltage of 6.39 V at a current density of 50 mA/cm$^2$, a high luminosity of 2453 cd/m$^2$, a luminescent efficiency of 4.90 cd/A, and a half-lifespan of 186 hours at 100 mA/cm$^2$.

Example 7

An organic light-emitting device was manufactured in the same manner as in Example 1, except that Compound 55 was used instead of Compound 2 to form the EML.

The organic light-emitting device had a driving voltage of 6.20 V at a current density of 50 mA/cm$^2$, a high luminosity of 2667 cd/cm$^2$, a luminescent efficiency of 5.33 cd/A, and a half-lifespan of 184 hours at 100 mA/cm$^2$.

Example 8

An organic light-emitting device was manufactured in the same manner as in Example 1, except that Compound 57 was used instead of Compound 2 to form the EML.

The organic light-emitting device had a driving voltage of 6.61 V at a current density of 50 mA/cm$^2$, a high luminosity of 2791 cd/m$^2$, a luminescent efficiency of 5.58 cd/A, and a half-lifespan of 245 hours at 100 mA/cm$^2$.

Example 9

An organic light-emitting device was manufactured in the same manner as in Example 1, except that Compound 73 was used instead of Compound 2 to form the EML.

The organic light-emitting device had a driving voltage of 6.30 V at a current density of 50 mA/cm$^2$, a high luminosity of 2533 cd/m$^2$, a luminescent efficiency of 5.06 cd/A, and a half-lifespan of 208 hours at 100 mA/cm$^2$.

Example 10

An organic light-emitting device was manufactured in the same manner as in Example 1, except that Compound 82 was used instead of Compound 2 to form the EML.

The organic light-emitting device had a driving voltage of 6.48 V at a current density of 50 mA/cm$^2$, a high luminosity of 2945 cd/m$^2$, a luminescent efficiency of 5.89 cd/A, and a half-lifespan of 211 hours at 100 mA/cm$^2$.

Example 11

An organic light-emitting device was manufactured in the same manner as in Example 1, except that Compound 87 was used instead of Compound 2 to form the EML.

The organic light-emitting device had a driving voltage of 6.45 V at a current density of 50 mA/cm$^2$, a high luminosity of 2950 cd/m$^2$, a luminescent efficiency of 5.90 cd/A, and a half-lifespan of 265 hours at 100 mA/cm$^2$.

Example 12

An organic light-emitting device was manufactured in the same manner as in Example 1, except that Compound 89 was used instead of Compound 2 to form the EML.

The organic light-emitting device had a driving voltage of 6.46 V at a current density of 50 mA/cm$^2$, a high luminosity of 2925 cd/m$^2$, a luminescent efficiency of 5.85 cd/A, and a half-lifespan of 243 hours at 100 mA/cm$^2$.

Example 13

An organic light-emitting device was manufactured in the same manner as in Example 1, except that Compound 95 was used instead of Compound 2 to form the EML.

The organic light-emitting device had a driving voltage of 6.32 V at a current density of 50 mA/cm$^2$, a high luminosity of 2970 cd/m$^2$, a luminescent efficiency of 5.94 cd/A, and a half-lifespan of 160 hours at 100 mA/cm$^2$.

Example 14

An organic light-emitting device was manufactured in the same manner as in Example 1, except that Compound 105 was used instead of Compound 2 to form the EML.

The organic light-emitting device had a driving voltage of 6.45 V at a current density of 50 mA/cm$^2$, a high luminosity of 2875 cd/m$^2$, a luminescent efficiency of 5.75 cd/A, and a half-lifespan of 249 hours at 100 mA/cm$^2$.

Example 15

An organic light-emitting device was manufactured in the same manner as in Example 1, except that Compound 108 was used instead of Compound 2 to form the EML.

The organic light-emitting device had a driving voltage of 6.21 V at a current density of 50 mA/cm$^2$, a high luminosity of 2545 cd/m$^2$, a luminescent efficiency of 5.09 cd/A, and a half-lifespan of 201 hours at 100 mA/cm$^2$.

Example 16

An organic light-emitting device was manufactured in the same manner as in Example 1, except that Compound 124 was used instead of Compound 2 to form the EML.

The organic light-emitting device had a driving voltage of 6.41 V at a current density of 50 mA/cm$^2$, a high luminosity of 2820 cd/m$^2$, a luminescent efficiency of 5.64 cd/A, and a half-lifespan of 225 hours at 100 mA/cm$^2$.

Example 17

An organic light-emitting device was manufactured in the same manner as in Example 1, except that Compound 141 was used instead of Compound 2 to form the EML.

The organic light-emitting device had a driving voltage of 6.46 V at a current density of 50 mA/cm$^2$, a high luminosity of 2730 cd/m$^2$, a luminescent efficiency of 5.46 cd/A, and a half-lifespan of 208 hours at 100 mA/cm$^2$.

Example 18

An organic light-emitting device was manufactured in the same manner as in Example 1, except that Compound 146 was used instead of Compound 2 to form the EML.

The organic light-emitting device had a driving voltage of 6.42 V at a current density of 50 mA/cm$^2$, a high luminosity of 2840 cd/m$^2$, a luminescent efficiency of 5.68 cd/A, and a half-lifespan of 211 hours at 100 mA/cm$^2$.

Example 19

An organic light-emitting device was manufactured in the same manner as in Example 1, except that Compound 158 was used instead of Compound 2 to form the EML.

The organic light-emitting device had a driving voltage of 6.47 V at a current density of 50 mA/cm$^2$, a high luminosity of 2930 cd/m$^2$, a luminescent efficiency of 5.86 cd/A, and a half-lifespan of 194 hours at 100 mA/cm$^2$.

Comparative Example 1

An organic light-emitting device was manufactured in the same manner as in Example 1, except that a known blue fluorescent dopant 4,4'-bis[2-(4-(N,N-diphenylamino)phenyl)vinyl]biphenyl (DPAVBi) was used instead of Compound 2 to form the EML.

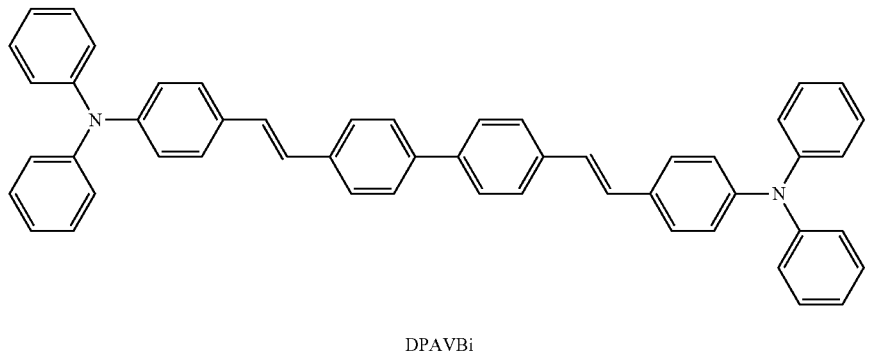 [SMILES: C(=C\c1ccc(N(c2ccccc2)c2ccccc2)cc1)/c1ccc(-c2ccc(/C=C/c3ccc(N(c4ccccc4)c4ccccc4)cc3)cc2)cc1]

DPAVBi

The organic light-emitting device had a driving voltage of 7.35 V at a current density of 50 mA/cm², a high luminosity of 2065 cd/m², a luminescent efficiency of 4.13 cd/A, and a half-lifespan of 145 hours at 100 mA/cm².

The organic light-emitting devices including the heterocyclic compounds as a host material or dopant material of the EML according to the present invention had lower driving voltage, better I-V-L characteristics with higher efficiency, and longer lifespan than the organic light-emitting device manufactured using known materials according to Comparative Example 1. In particular, the lifespan of the organic light-emitting devices manufactured according to Examples 1 to 19 was far longer than that of the organic light-emitting device manufactured according to Comparative Example 1. The results are shown in Table 1 below:

The heterocyclic compounds according to embodiments of the present invention have excellent light-emitting characteristics and excellent electron transporting characteristics, and thus may be used as electron injecting materials or electron transporting materials suitable for all-color fluorescent and phosphorescent devices, such as red, green, blue, and white fluorescent and phosphorescent devices. In particular, the heterocyclic compounds are efficiently used as light-emitting materials of green, blue, and white fluorescent devices. By using the heterocyclic compounds, organic light-emitting devices having high efficiency, low driving voltage, high brightness, and long lifespan may be prepared.

While the present invention has been particularly shown and described with reference to exemplary embodiments thereof, it will be understood by those of ordinary skill in the art that various changes in form and details may be made therein without departing from the spirit and scope of the present invention as defined by the following claims.

TABLE 1

|  | Host or dopant material | Driving voltage (V) | Current density (mA/cm²) | Brightness (cd/m²) | Efficiency (cd/A) | Color | Half-life span (hr @100 mA/cm²) |
|---|---|---|---|---|---|---|---|
| Example 1 | Compound 2 | 6.37 | 50 | 2,739 | 5.47 | blue | 270 hr |
| Example 2 | Compound 11 | 6.49 | 50 | 2,981 | 5.96 | blue | 235 hr |
| Example 3 | Compound 24 | 6.23 | 50 | 2,280 | 4.56 | blue | 208 hr |
| Example 4 | Compound 34 | 6.42 | 50 | 2,695 | 5.39 | blue | 212 hr |
| Example 5 | Compound 45 | 6.38 | 50 | 2,577 | 5.15 | blue | 225 hr |
| Example 6 | Compound 48 | 6.39 | 50 | 2,453 | 4.90 | blue | 186 hr |
| Example 7 | Compound 55 | 6.20 | 50 | 2,667 | 5.33 | blue | 184 hr |
| Example 8 | Compound 57 | 6.61 | 50 | 2,791 | 5.58 | blue | 245 hr |
| Example 9 | Compound 73 | 6.30 | 50 | 2,533 | 5.06 | blue | 208 hr |
| Example 10 | Compound 82 | 6.48 | 50 | 2,945 | 5.89 | blue | 211 hr |
| Example 11 | Compound 87 | 6.45 | 50 | 2,950 | 5.90 | blue | 265 hr |
| Example 12 | Compound 89 | 6.46 | 50 | 2,925 | 5.85 | blue | 243 hr |
| Example 13 | Compound 95 | 6.32 | 50 | 2,970 | 5.94 | blue | 160 hr |
| Example 14 | Compound 105 | 6.45 | 50 | 2,875 | 5.75 | blue | 249 hr |
| Example 15 | Compound 108 | 6.21 | 50 | 2,545 | 5.09 | bluish green | 201 hr |
| Example 16 | Compound 124 | 6.41 | 50 | 2,820 | 5.64 | blue | 225 hr |
| Example 17 | Compound 141 | 6.46 | 50 | 2,730 | 5.46 | blue | 208 hr |
| Example 18 | Compound 146 | 6.42 | 50 | 2,840 | 5.68 | blue | 211 hr |
| Example 19 | Compound 158 | 6.47 | 50 | 2,930 | 5.86 | blue | 194 hr |
| Comparative Example 1 | DPAVBi | 7.35 | 50 | 2,065 | 4.13 | blue | 145 hr |

What is claimed is:

1. A heterocyclic compound represented by Formula 1 below:

<Formula 1>

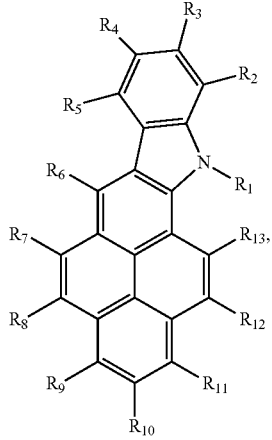

wherein $R_1$ to $R_{13}$ are each independently a hydrogen atom, a heavy hydrogen atom, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C1-C60 alkoxy group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, a substituted or unsubstituted C6-C60 condensed polycyclic group, a halogen atom, a cyano group, a nitro group, a hydroxy group, or a carboxy group.

2. The heterocyclic compound of claim 1, wherein $R_1$ to $R_5$ are each independently a hydrogen atom, a heavy hydrogen atom, a halogen atom, a cyano group, a substituted or unsubstituted C1-C20 alkyl group, or one of Formulae 2a to 2i below:

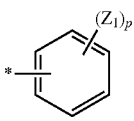

2a

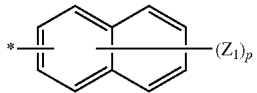

2b

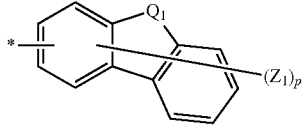

2c

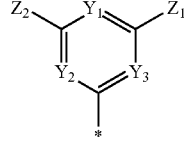

2d

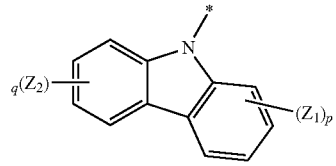

2e

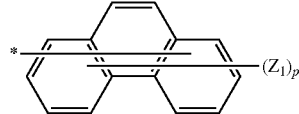

2f

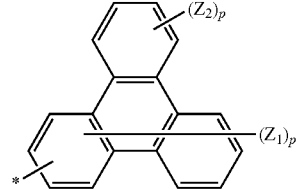

2g

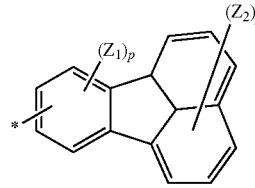

2h

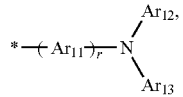

2i wherein $Q_1$ is a linking group represented by —$C(R_{14})(R_{15})$—, —$N(R_{16})$—, —S—, or —O—;

$Y_1$, $Y_2$ and $Y_3$ are each independently a linking group represented by —N= or —$C(R_{17})$=;

$Z_1$, $Z_2$, $Ar_{12}$, $Ar_{13}$, $R_{14}$, $R_{15}$, $R_{16}$, and $R_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

$Ar_{11}$ is a substituted or unsubstituted C1-C20 alkylene group, a substituted or unsubstituted C5-C20 arylene group, or a substituted or unsubstituted C3-C20 heteroarylene group;

p is an integer from 1 to 12;

q is an integer from 1 to 12;

r is an integer from 0 to 5; and

* is a binding site.

3. The heterocyclic compound of claim 1, wherein $R_1$ to $R_5$ are each independently a hydrogen atom, a heavy hydrogen atom, a halogen atom, a cyano group, a methyl group, an ethyl group, a propyl group, a butyl group, a t-butyl group, a pentyl group, or one of Formulae 3a to 3m below:

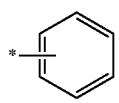

3a

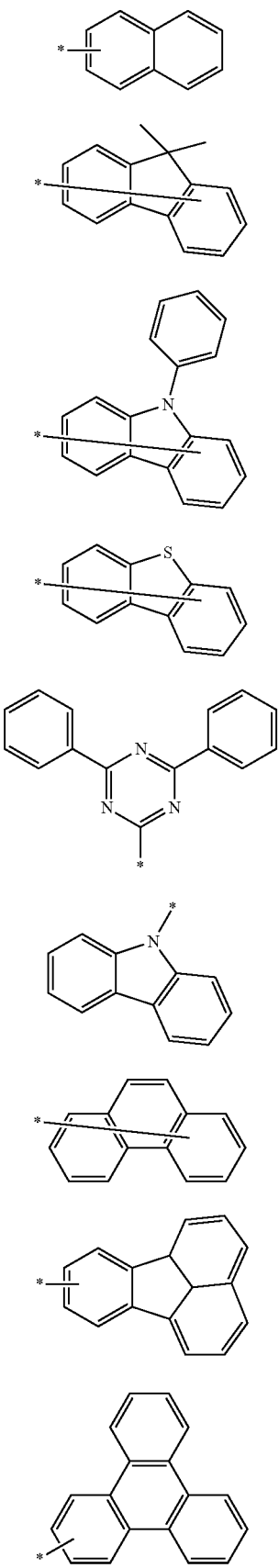
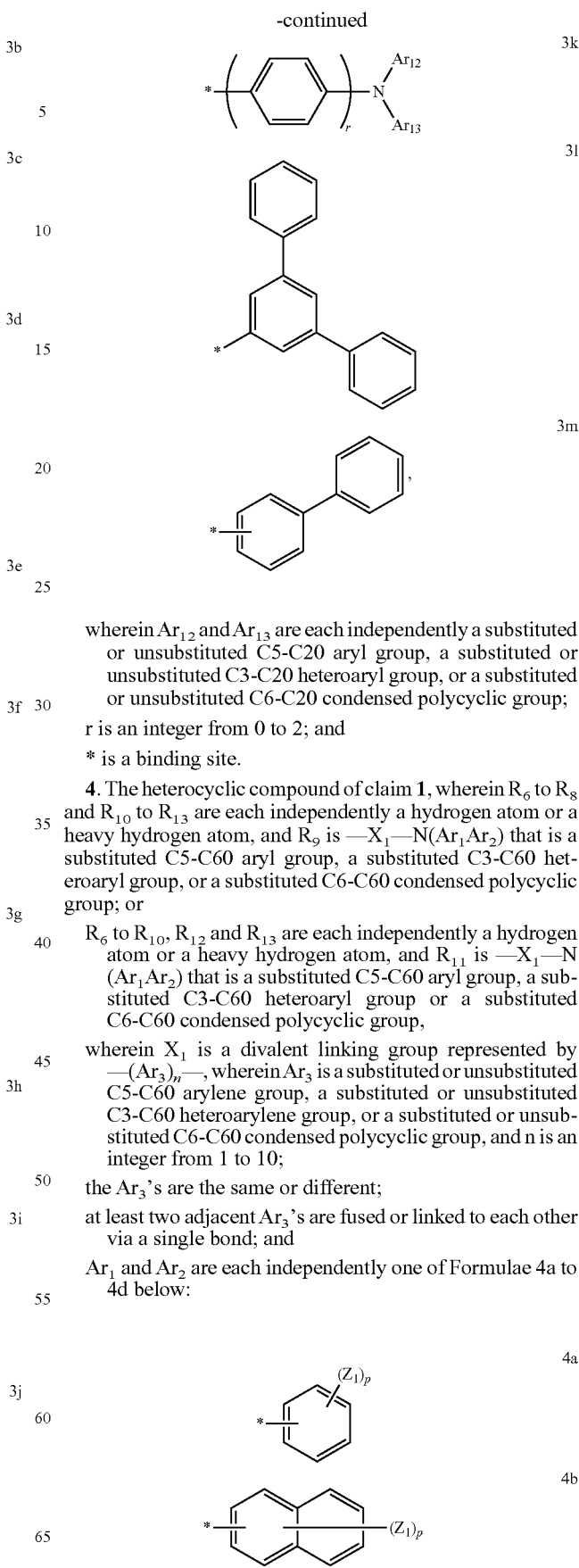

wherein Ar$_{12}$ and Ar$_{13}$ are each independently a substituted or unsubstituted C5-C20 aryl group, a substituted or unsubstituted C3-C20 heteroaryl group, or a substituted or unsubstituted C6-C20 condensed polycyclic group;

r is an integer from 0 to 2; and

* is a binding site.

4. The heterocyclic compound of claim 1, wherein R$_6$ to R$_8$ and R$_{10}$ to R$_{13}$ are each independently a hydrogen atom or a heavy hydrogen atom, and R$_9$ is —X$_1$—N(Ar$_1$Ar$_2$) that is a substituted C5-C60 aryl group, a substituted C3-C60 heteroaryl group, or a substituted C6-C60 condensed polycyclic group; or R$_6$ to R$_{10}$, R$_{12}$ and R$_{13}$ are each independently a hydrogen atom or a heavy hydrogen atom, and R$_{11}$ is —X$_1$—N(Ar$_1$Ar$_2$) that is a substituted C5-C60 aryl group, a substituted C3-C60 heteroaryl group or a substituted C6-C60 condensed polycyclic group, wherein X$_1$ is a divalent linking group represented by —(Ar$_3$)$_n$—, wherein Ar$_3$ is a substituted or unsubstituted C5-C60 arylene group, a substituted or unsubstituted C3-C60 heteroarylene group, or a substituted or unsubstituted C6-C60 condensed polycyclic group, and n is an integer from 1 to 10;

the Ar$_3$'s are the same or different;

at least two adjacent Ar$_3$'s are fused or linked to each other via a single bond; and Ar$_1$ and Ar$_2$ are each independently one of Formulae 4a to 4d below:

-continued

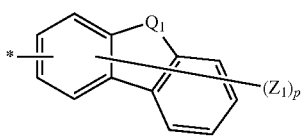
4c

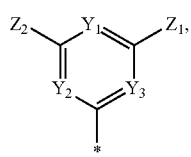
4d wherein $Q_1$ is a linking group represented by —$C(R_{14})(R_{15})$—, —$N(R_{16})$—, —S—, or —O—;

$Y_1$, $Y_2$ and $Y_3$ are each independently a linking group represented by —N= or —$C(R_{17})$=;

$Z_1$, $Z_2$, $R_{14}$, $R_{15}$, $R_{16}$, and $R_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

p is an integer from 1 to 8; and

* is a binding site.

5. The heterocyclic compound of claim 1, wherein $R_6$ to $R_8$ and $R_{10}$ to $R_{13}$ are each independently a hydrogen atom or a heavy hydrogen atom, and $R_9$ is —$X_1$—$N(Ar_1Ar_2)$ that is a substituted C5-C60 aryl group, a substituted C3-C60 heteroaryl group, or a substituted C6-C60 condensed polycyclic group; or $R_6$ to $R_{10}$, $R_{12}$ and $R_{13}$ are each independently a hydrogen atom or a heavy hydrogen atom, and $R_{11}$ is —$X_1$—N($Ar_1Ar_2$) that is a substituted C5-C60 aryl group, a substituted C3-C60 heteroaryl group or a substituted C6-C60 condensed polycyclic group, wherein $X_1$ is a divalent linking group represented by —$(Ar_3)_n$—, wherein $Ar_3$ is a substituted or unsubstituted C5-C60 arylene group, a substituted or unsubstituted C3-C60 heteroarylene group, or a substituted or unsubstituted C6-C60 condensed polycyclic group, and n is an integer from 1 to 10;

the $Ar_3$'s are the same or different;

at least two adjacent $Ar_3$'s are fused or linked to each other via a single bond; and $Ar_1$ and $Ar_2$ are each independently represented by one of Formulae 5a to 5i below:

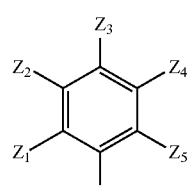
5a

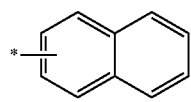
5b

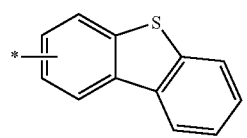
5c

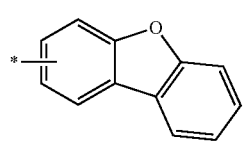
5d

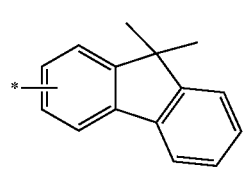
5e

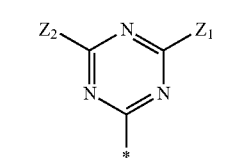
5f

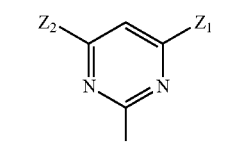
5g

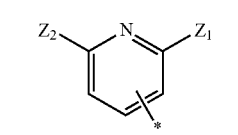
5h

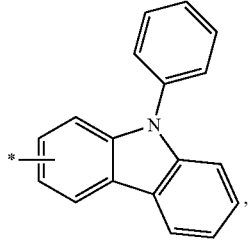
5i wherein $Z_1$ to $Z_5$ are each independently a hydrogen atom, a heavy hydrogen atom, a halogen atom, a cyano group, a substituted or unsubstituted C1-C20 alkyl group, a substituted or unsubstituted C1-C20 alkoxy group, a substituted or unsubstituted C5-C20 aryl group, a substituted or unsubstituted C3-C20 heteroaryl group, or a substituted or unsubstituted C6-C20 condensed polycyclic group; and

* is a binding site.

6. The heterocyclic compound of claim 1, wherein $R_9$ or $R_{11}$ are each independently $X_1$—$N(Ar_1Ar_2)$ that is a substituted C5-C60 aryl group, a substituted C3-C60 heteroaryl group, or a substituted C6-C60 condensed polycyclic group, wherein $Ar_1$ and $Ar_2$ are each independently a substituted or unsubstituted C3-C50 cycloalkyl group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, or a substituted or unsubstituted C6-C60 condensed polycyclic group; and $X_1$ is a divalent linking group represented by —$(Ar_3)_n$—, wherein $Ar_3$ is one of Formulae 6a to 6e, and the $Ar_3$'s are the same or different; and at least two adjacent $Ar_3$'s are fused or linked to each other via a single bond:

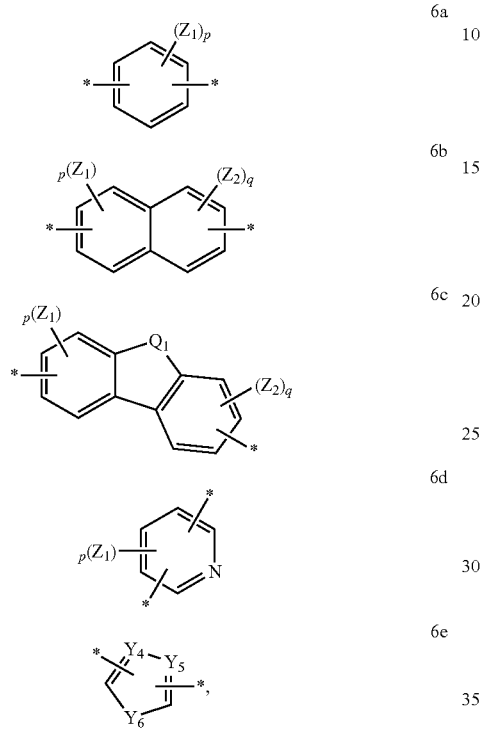

wherein $Q_1$ is a linking group represented by —C($R_{14}$)($R_{15}$)—, —S—, or —O—;

$Y_4$, $Y_5$ and $Y_6$ are each independently a linking group represented by —O—, —S—, —N= or —C($R_{17}$)=;

$Z_1$, $Z_2$, $R_{14}$, $R_{15}$, $R_{16}$, and $R_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

p is an integer from 1 to 4;

q is an integer from 1 to 4; and

* is a binding site.

7. The heterocyclic compound of claim 1, wherein $R_9$ or $R_{11}$ are each independently $X_1$—N($Ar_1Ar_2$) that is a substituted C5-C60 aryl group, a substituted C3-C60 heteroaryl group, or a substituted C6-C60 condensed polycyclic group, wherein $Ar_1$ and $Ar_2$ are each independently a substituted or unsubstituted C3-C50 cycloalkyl group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, or a substituted or unsubstituted C6-C60 condensed polycyclic group; and $X_1$ is one of Formulae 7a to 7k below:

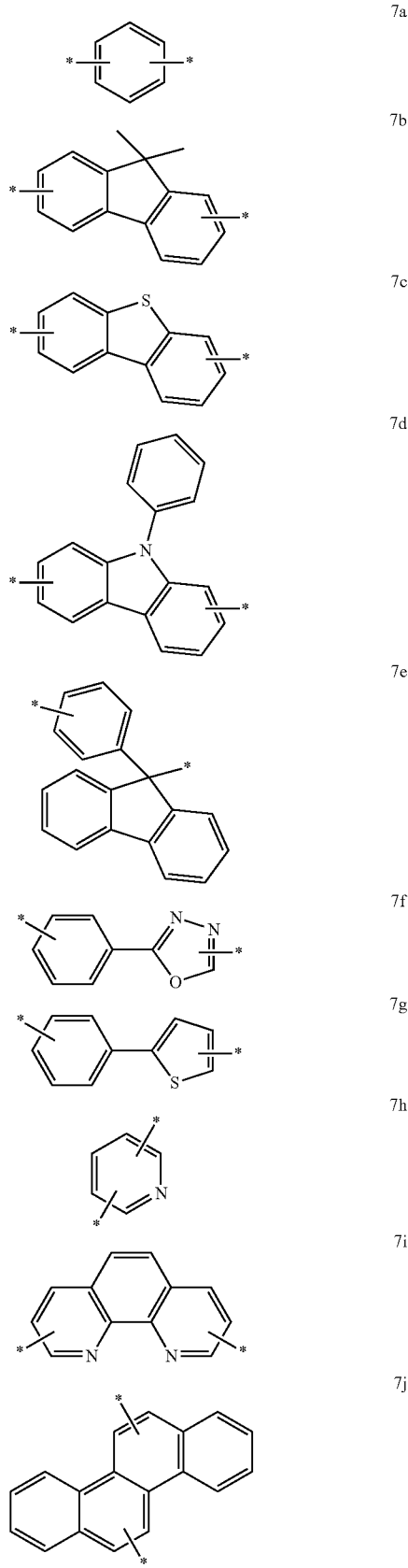

-continued

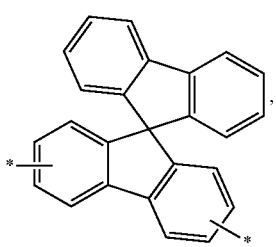

7k wherein * is a binding site.

8. The heterocyclic compound of claim 1, wherein the heterocyclic compound of Formula 1 is represented by Formula 2 or Formula 3 below:

<Formula 2>

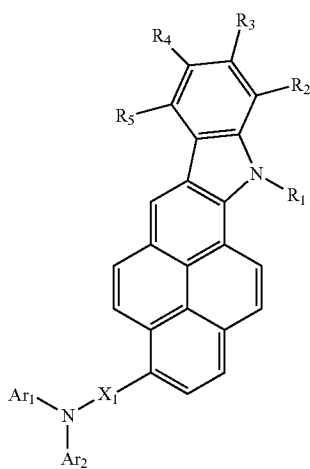

<Formula 3>

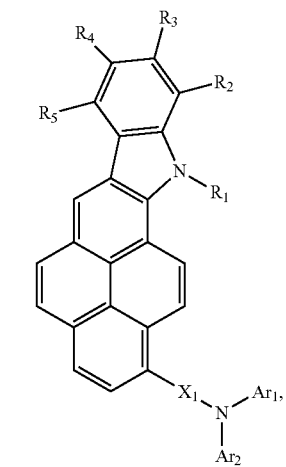

wherein $R_1$ to $R_5$ are each independently a hydrogen atom, a heavy hydrogen atom, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C1-C60 alkoxy group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, a substituted or unsubstituted C6-C60 condensed polycyclic group, a halogen atom, a cyano group, a nitro group, a hydroxy group, or a carboxy group;

$Ar_1$ and $Ar_2$ are each independently a substituted or unsubstituted C3-C50 cycloalkyl group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, or a substituted or unsubstituted C6-C60 condensed polycyclic group;

$X_1$ is a divalent linking group represented by $—(Ar_3)_n—$, wherein $Ar_3$ may be a substituted or unsubstituted C5-C60 arylene group, a substituted or unsubstituted C3-C60 heteroarylene group, or a substituted or unsubstituted C6-C60 condensed polycyclic group, and n is an integer from 1 to 10;

the $Ar_3$'s are the same or different; and at least two adjacent $Ar_3$'s are fused or linked to each other via a single bond.

9. The heterocyclic compound of claim 8, wherein $R_1$ to $R_5$ are each independently a hydrogen atom, a heavy hydrogen atom, a halogen atom, a cyano group, a substituted or unsubstituted C1-C20 alkyl group, or one of Formulae 2a to 2i below:

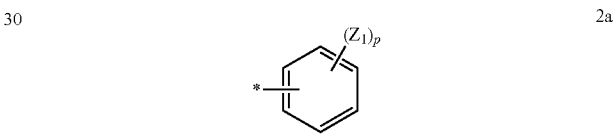

-continued

2g

2h

2i wherein Q₁ is a linking group represented by —C(R₁₄)(R₁₅)—, —N(R₁₆)—, —S—, or —O—;

Y₁, Y₂ and Y₃ are each independently a linking group represented by —N= or —C(R₁₇)=;

Z₁, Z₂, Ar₁₂, Ar₁₃, R₁₄, R₁₅, R₁₆, and R₁₇ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

Ar₁₁ is a substituted or unsubstituted C1-C20 alkylene group, a substituted or unsubstituted C5-C20 arylene group, or a substituted or unsubstituted C3-C20 heteroarylene group;

p is an integer from 1 to 12;

q is an integer from 1 to 12;

r is an integer from 0 to 5; and

* is a binding site.

10. The heterocyclic compound of claim 8, wherein R₁ to R₅ are each independently a hydrogen atom, a heavy hydrogen atom, a halogen atom, a cyano group, a methyl group, an ethyl group, a propyl group, a butyl group, a t-butyl group, a pentyl group, or one of Formulae 3a to 3m below:

3a

3b

3c

-continued

3d

3e

3f

3g

3h

3i

3j

3k

173
-continued

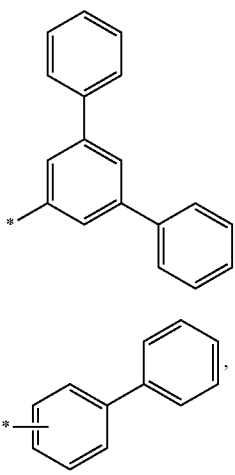

31

3m wherein Ar$_{12}$ and Ar$_{13}$ are each independently a substituted or unsubstituted C5-C20 aryl group, a substituted or unsubstituted C3-C20 heteroaryl group, or a substituted or unsubstituted C6-C20 condensed polycyclic group;
r is an integer from 0 to 2; and
* is a binding site.

11. The heterocyclic compound of claim 8, wherein Ar$_1$ and Ar$_2$ are each independently one of Formulae 4a to 4d below:

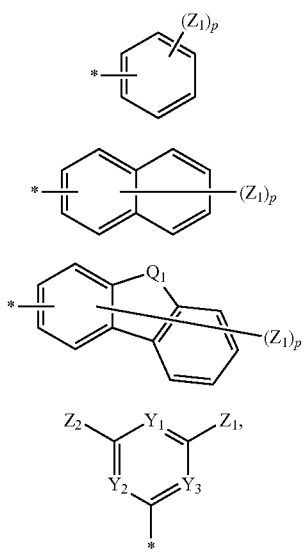

4a

4b

4c

4d wherein Q$_1$ is a linking group represented by —C(R$_{14}$)(R$_{15}$)—, —N(R$_{16}$)—, —S—, or —O—;
Y$_1$, Y$_2$ and Y$_3$ are each independently a linking group represented by —N= or —C(R$_{17}$)=;
Z$_1$, Z$_2$, R$_{14}$, R$_{15}$, R$_{16}$, and R$_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;
p is an integer from 1 to 8; and
* is a binding site.

174

12. The heterocyclic compound of claim 8, wherein Ar$_1$ and Ar$_2$ are each independently one of Formulae 5a to 5i below:

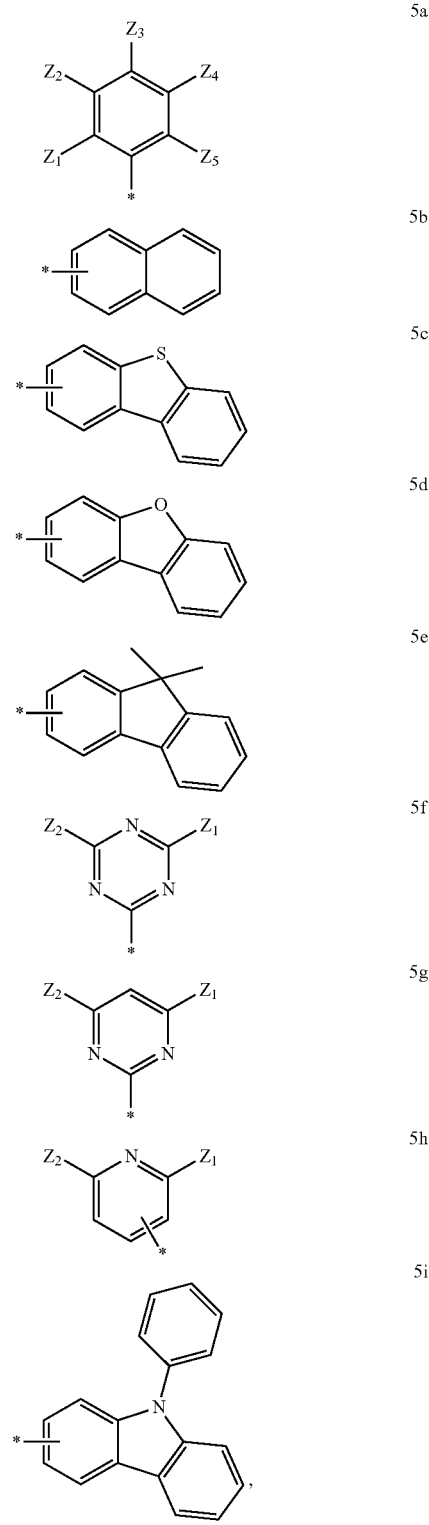

5a

5b

5c

5d

5e

5f

5g

5h

5i wherein Z$_1$ to Z$_5$ are each independently a hydrogen atom, a heavy hydrogen atom, a halogen atom, a cyano group, a substituted or unsubstituted C1-C20 alkyl group, a substituted or unsubstituted C1-C20 alkoxy group, a substituted or unsubstituted C5-C20 aryl group, a substituted or unsubstituted C3-C20 heteroaryl group, or a substituted or unsubstituted C6-C20 condensed polycyclic group; and

* is a binding site.

13. The heterocyclic compound of claim 8, wherein $Ar_3$ is one of Formulae 6a to 6e below:

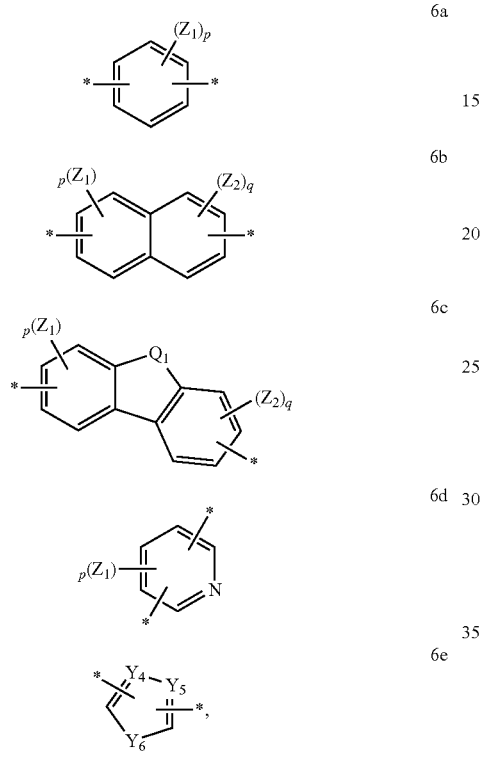

wherein $Q_1$ is a linking group represented by —C($R_{14}$)($R_{15}$)—, —N($R_{16}$)—, —S—, or —O—;

$Y_4$, $Y_5$ and $Y_6$ are each independently a linking group represented by —O—, —S—, —N= or —C($R_{17}$)=;

$Z_1$, $Z_2$, $R_{14}$, $R_{15}$, $R_{16}$, and $R_{17}$ are each independently a hydrogen atom, a heavy hydrogen atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, a halogen atom, a cyano group, a nitro group, a hydroxy group, or a carboxy group;

p is an integer from 1 to 4;

q is an integer from 1 to 4; and

* is a binding site.

14. The heterocyclic compound of claim 8, wherein $X_1$ is one of Formulae 7a to 7k below:

7a

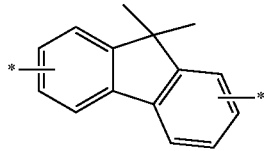

7b

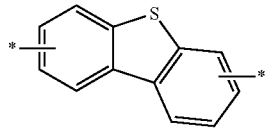

7c

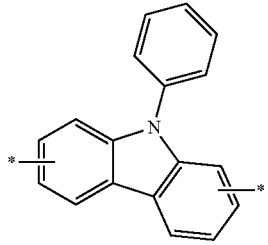

7d

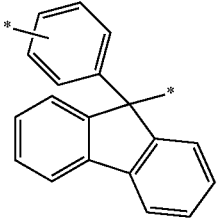

7e

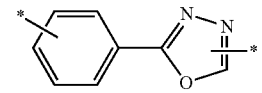

7f

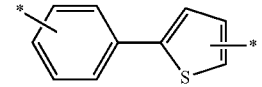

7g

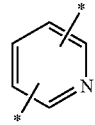

7h

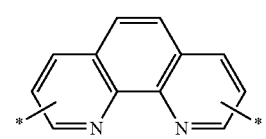

7i

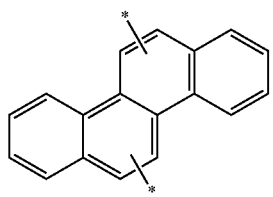

7j

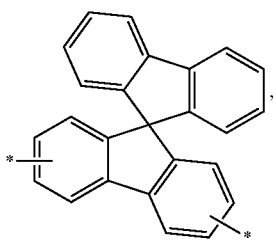
7k
wherein * is a binding site.
15. The heterocyclic compound of claim 1, wherein the heterocyclic compound of Formula 1 is one of the compounds below:
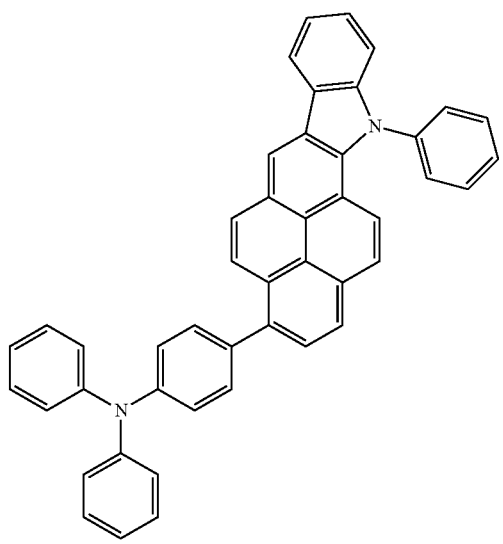
2
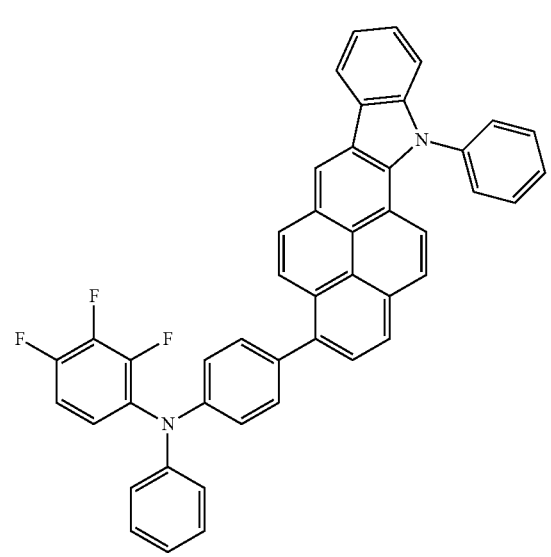
11
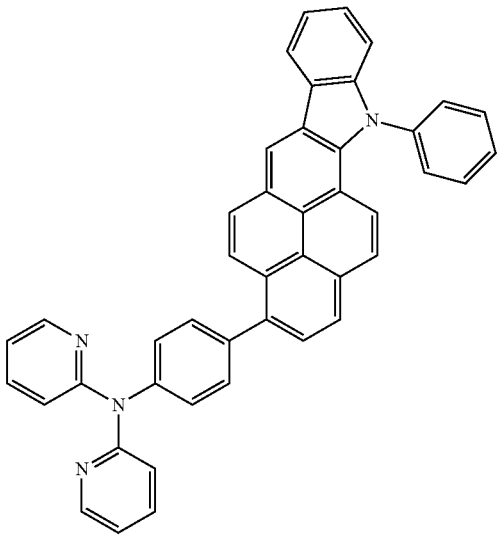
24
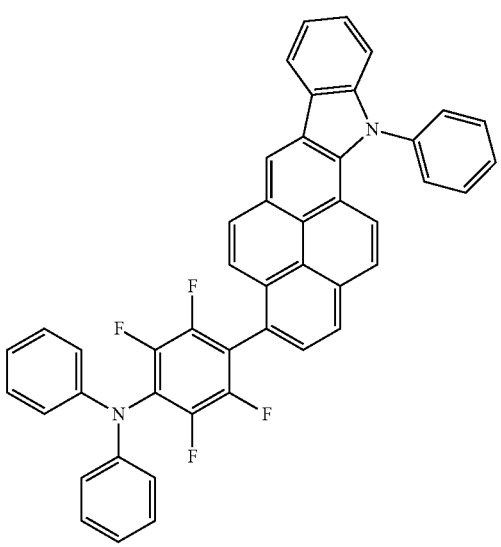
34
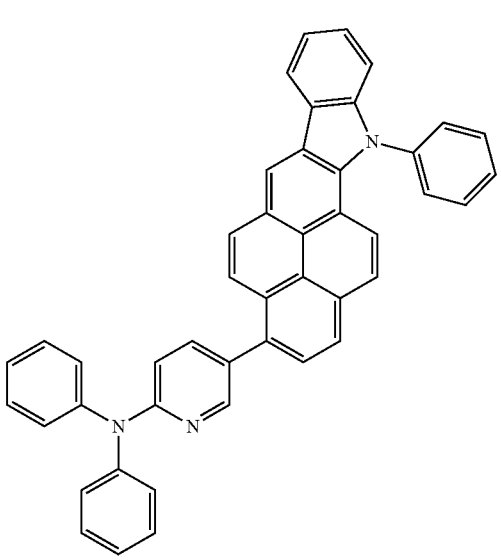
45

179
-continued
180
-continued
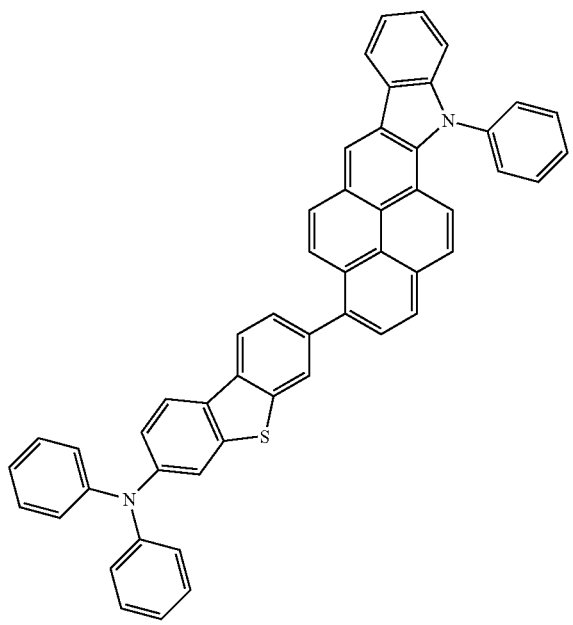
48
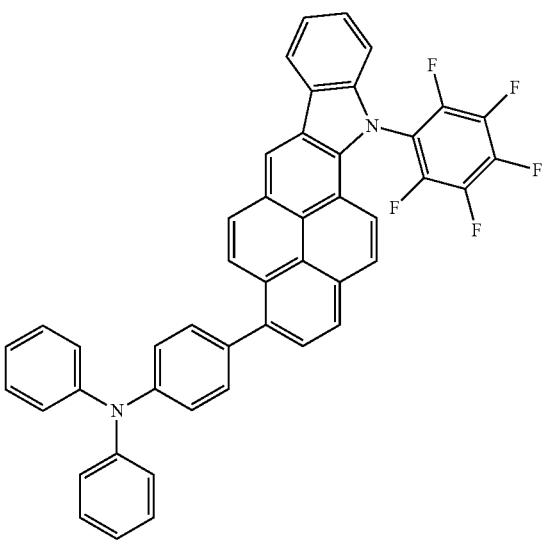
57
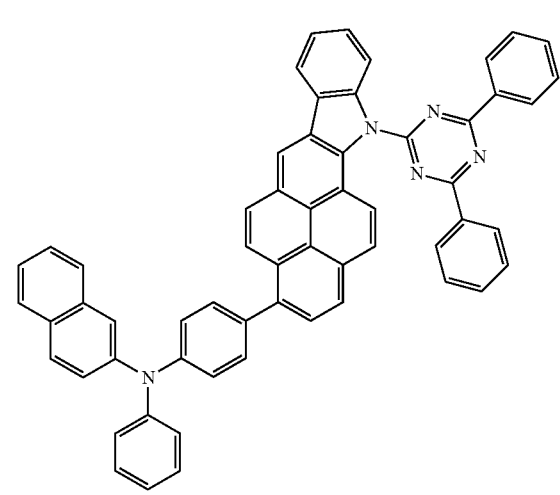
55
73

82
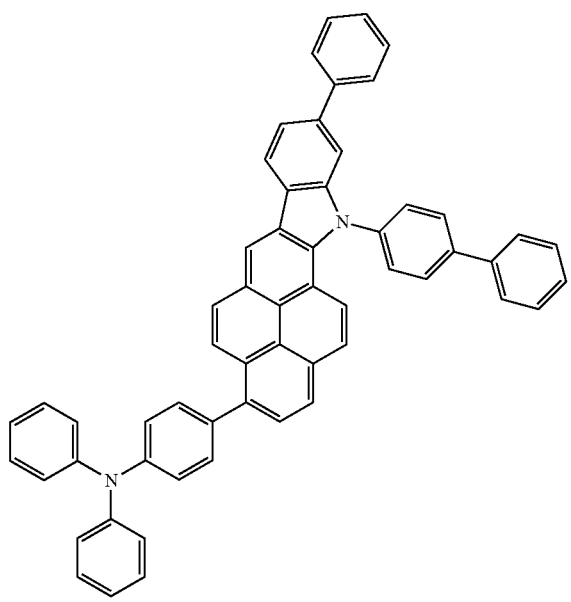
87
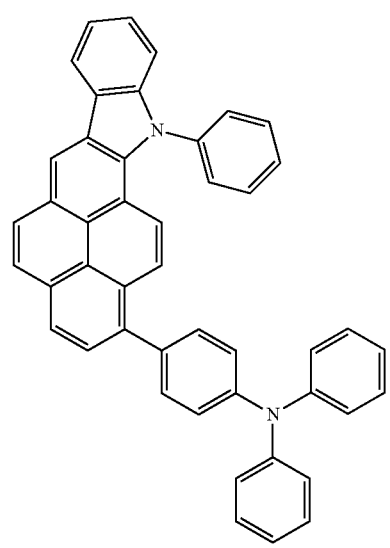
89
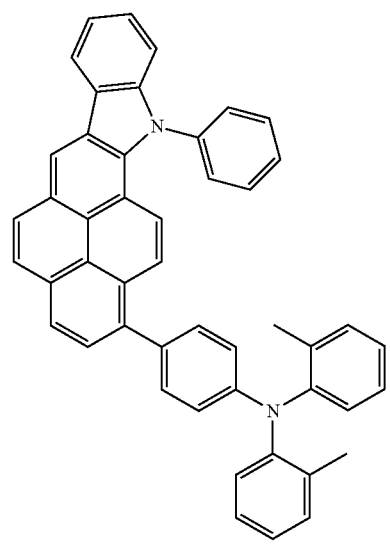
95
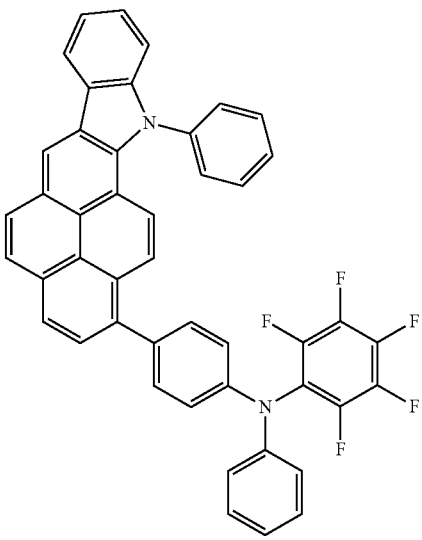
105
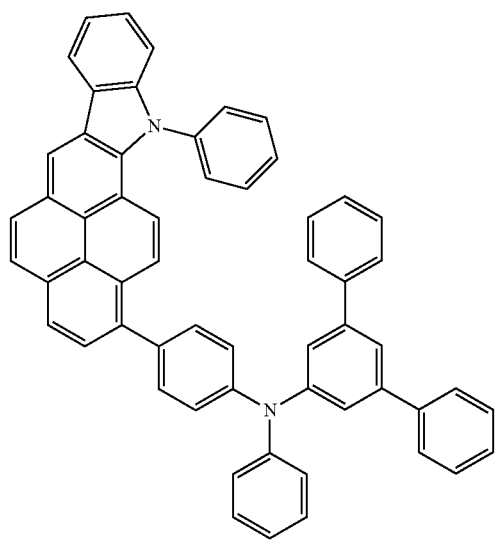
108
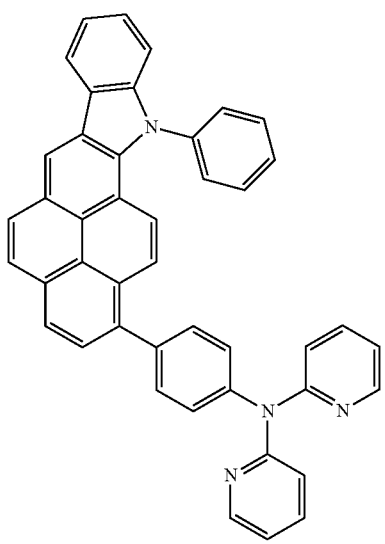

183
-continued

124

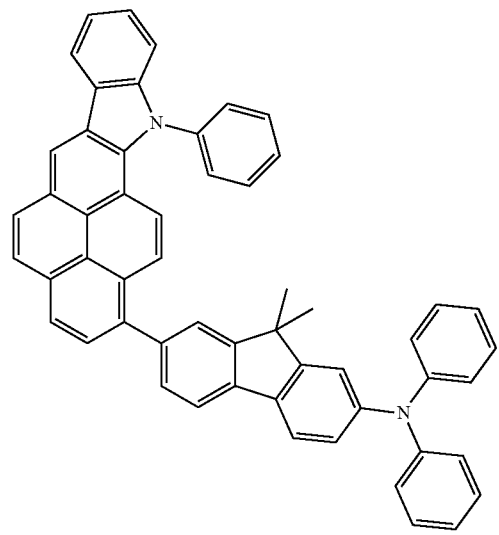

141

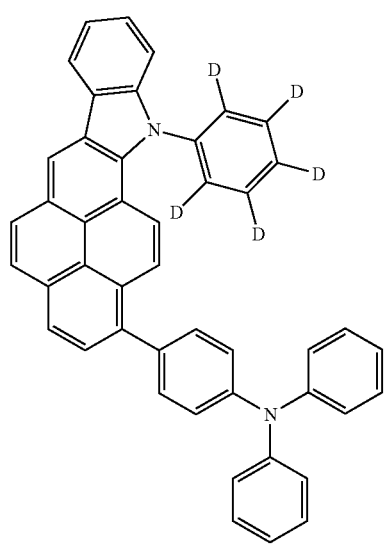

146

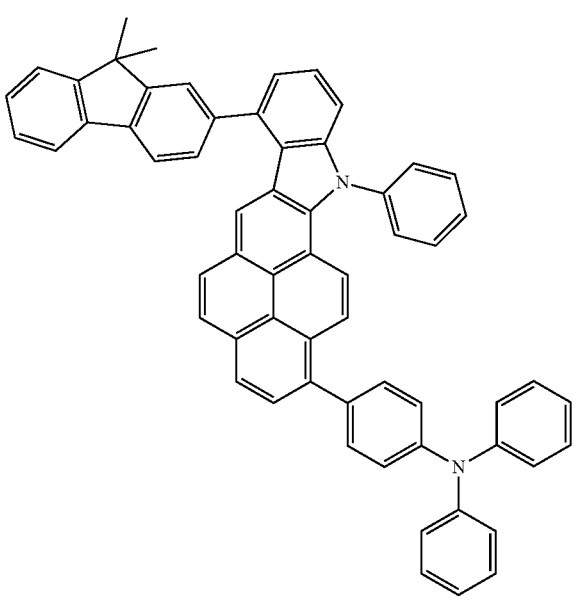

184
-continued

158

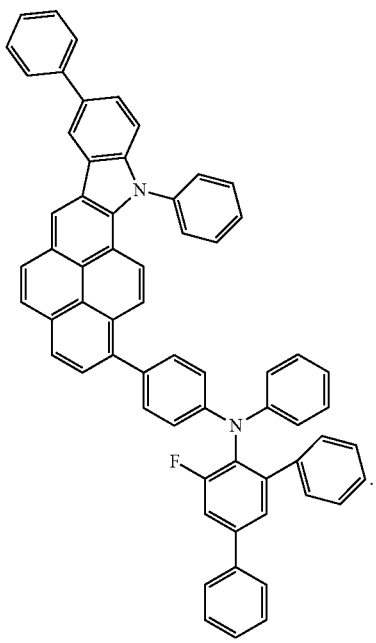

16. An organic light-emitting device comprising:
a first electrode;
a second electrode; and
an organic layer interposed between the first electrode and the second electrode,
the organic layer comprised of a first layer comprising a heterocyclic compound according to claim 1.

17. The organic light-emitting device of claim 16, wherein the first layer comprises a hole injection layer, a hole transport layer, a layer having both hole injecting and hole transporting capabilities, an emission layer, an electron injection layer, an electron transport layer, or a layer having both electron injecting and electron transporting capabilities.

18. The organic light-emitting device of claim 16, wherein the first layer comprises a hole injection layer, a hole transport layer, a layer having both hole injecting and hole transporting capabilities, an emission layer, an electron injection layer, an electron transport layer, or a layer having both electron injecting and electron transporting capabilities, wherein the first layer further comprises a charge-generating material.

19. The organic light-emitting device of claim 16, wherein the first layer is formed of a heterocyclic compound represented by Formula 1 by using a wet process;

<Formula 1>

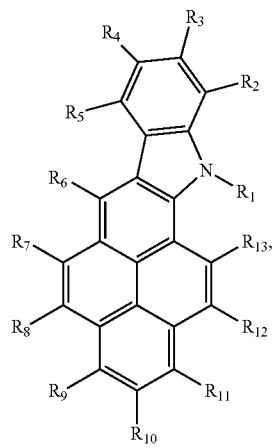

wherein $R_1$ to $R_{13}$ are each independently a hydrogen atom, a heavy hydrogen atom, a substituted or unsubstituted C1-C60 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C1-C60 alkoxy group, a substituted or unsubstituted C5-C60 aryloxy group, a substituted or unsubstituted C5-C60 arylthio group, a substituted or unsubstituted C5-C60 aryl group, an amino group substituted with a C5-C60 aryl group or a C3-C60 heteroaryl group, a substituted or unsubstituted C3-C60 heteroaryl group, a substituted or unsubstituted C6-C60 condensed polycyclic group, a halogen atom, a cyano group, a nitro group, a hydroxy group, or a carboxy group.

20. A flat panel display device comprising the organic light-emitting device of claim 16, wherein a first electrode of the organic light-emitting device is electrically connected to a source electrode or a drain electrode of a thin film transistor.

* * * * *